United States Patent [19]

Kaji

[11] Patent Number: 5,583,040
[45] Date of Patent: Dec. 10, 1996

[54] MUTATION OF REPA PROTEIN

[76] Inventor: Akira Kaji, 334 Fillmore St., Jenkintown, Pa. 19046

[21] Appl. No.: 246,403

[22] Filed: May 20, 1994

[51] Int. Cl.⁶ ............................. C12N 1/21; C12N 15/31; C12N 15/70

[52] U.S. Cl. .................. 435/252.33; 435/252.3; 435/320.1; 536/23.7

[58] Field of Search ................... 435/252.3, 252.33, 435/320.1; 536/23.7

[56] References Cited

PUBLICATIONS

DiJoseph et al., J. Bacteriology 115(1), pp. 399–410 (1973).
Yamamoto et al., J. Bacteriology 146(1), pp. 85–92 (1981).
Kaji et al., "Drug Resistance in Bacteria", Mitsuhashi, Ed., Japan Scientific Press, pp. 59–70 (1982).
Kamio et al., J. Bacteriology 158(1), pp. 307–312 (1984).
Mochida et al., J. Bacteriology 173(8), pp. 2600–2607 (1991).
Kaji et al., Reprint from: The Roots of Modern Biochemistry, Eds., Kleinkauf et al. (1988).
Okawa et al., Biochemical and Biophysical Research Comm., vol. 142, No. 3, pp. 1084–1088 (1987).
Abeles et al., J. Mol. Biol., vol. 173, pp. 307–324 (1984).
Chattoraj et al., Plasmids in Bacteria, Plenum Pub. Co. New York, NY, pp. 355–381 (1985).

*Primary Examiner*—Mindy Fleisher
*Assistant Examiner*—Philip W. Carter
*Attorney, Agent, or Firm*—Birch, Stewart, Kolasch & Birch, LLP

[57] ABSTRACT

Mutant plasmids of Rts1 and P1 are provided which permit for high copy numbers of the plasmid in host bacteria. The mutant plasmids also possess other improved characteristics, including the ability to coexist with other vectors in host bacteria, such as *E. coli*, the ability to control copy numbers, within the range of about 20 to 120, by the use of different host bacteria growth medium, and the ability to remove the plasmids from host bacteria by a simple shift in the bacteria growth temperature. These plasmids may also contain an additional nucleotide sequence, $GH_3$, which confers increased temperature stability.

13 Claims, 27 Drawing Sheets

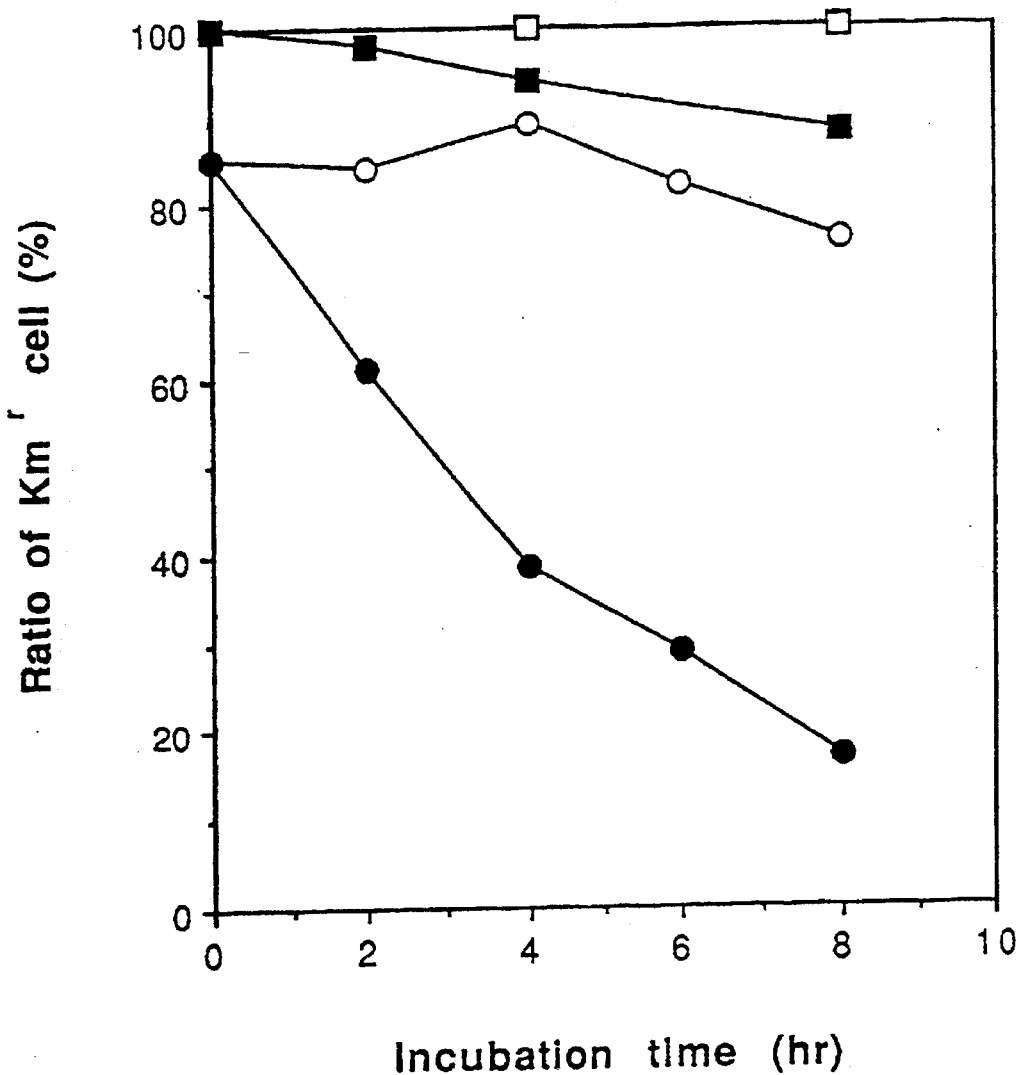
F I G. 3

```
From:
             10         20         30         40         50         60
             --         --         --         --         --         --
   1 GATCCCGAGC TTATCAGATG TATTCTGATA CGGTTCGATA AACCTGTCTT ACCAGAAAGG
  61 GAACAAACTC AGATGAAAAT CATCAAAATC TATACACCTC ATGAACTGGC TCTGTTGAGA
 121 GATCCTGCTT TCAGATTGAT AGTGATAGAG CAGATGGATT CGTTGAGCAA
 181 TATAATCTAC TAAATAATGT CTCACTTAAT CAGCCTAAGA ACGGTCTGGA GGTATTAATC
 241 GATCAGGCTA CAGGGCCAGC AGATAAGCAT CAACGCGTAT ACTTCAACGG ACTTCTTAAA
 301 TTTATCTATG AAACTGTATA CTTACGGTTA GAACCGATGG CTTTGGGGTA GTTCCGGGAA
 361 CCGTTGTCGG GTAATGAAATG GGTTTACCTT TCAATGCCCG GCAGCGGTTG GACAAGCGTA
 421 GCGCTCAGA TATTCCTCCA CATTACCATC ATTTAAAGTT ATCCACATAT CCACCGTGTA
 481 GATCCAATAA TAGATCCATA GAGAGATCCA GATAAAAACCA AAAAGATCCC CGTGGTCTGT
 541 AGCCTTACTG CCACAAGGCT TACAACGTTT TTCGGTGTGT GCTGAGGGGA AAAAGGTGTG
 601 TGCTGAGGGG AAGAAAGTGT GTGTTACGGG GATTTGGGTG TGTGCTGAGG GGAAAAAAGC
 661 TGGCGTCAC GGGGAAAATG CCACAATCGT CCACAATCGT AGCATTTACG TGGGGGGAA
 721 TTATTTATT ATGGAAACTC TGATACTTTT ATCGATGTG TTATTTGGTA ACACGGAAGA
 781 AAAACAAAAA CCATTAACAG TTAATGAACT GAATACAATT CAACCAGTGG CCTTTATGCG
 841 CCTTGGCCTG TTTGTGCCTA AACCATCAAG GTCATCTGAC TACAGCCCGA TGATTGATGT
 901 CAGTGAATTA AGTTCTACCT TTGAATTTGC AAGACTTGAG GGGTTTACTG ACATAAAAAT
 961 CACTGGTGAA CGTCTTGATA TGGATACTGA TTTCAAGGTG TGGATCGGCA TAGTCAAAGC
1021 GTTCAGCAAG TACGGGATTT CGTCAAACCG CATCAAACTG CAAGAAACTG AAGTTTTCTG AGTTCGCAAA
1081 AGATTGTGGT TTCCCCGGTA AAAAACTGGA CAAGAAACTG ATTTAAGCGA AGAGCCATA TAGATGAATC
1141 GCTTCGTAAA ATCAGGGGGA AATCGATCTC AGATAGCCTA TTTCAATGCC GGCAAAGATT CACAATCTGC
1201 ATATCATACC GGCCTCATAA AGATAGCCTA GGGAGTTATA CTACTTTGAT GATACAGACG TTGTGAACT
1261 GGAAGCAGAC GAGCGATTAT GGGAGTTATA CACGTCTAGA AGTTGCACAA TATCGTGTTG TTCTTCAACT
1321 ACATGCAATA AAAGCCCTTC CACGTCTAGA CTCCTATCTC TTTTAAACGC CTACGTGAAA GCCCTGTATA CCTTCCTGC
1381 AAGCCTTCCA AGTAACCCGG CTCCTATCTC AGAATCGAAT TTTTAAACGC CTACGTGAAA GGTTGTCTCT
1441 GATCAGTCAG GTTAAAGAAC AGAATCGAAT CTATGGTGAA AATCAAAAAA GCGATTACTA AGCTGATAGA
1501 TATCGGCTAT TTGGACGCTT CTATGGTGAA CTATGGTGAA AAAGGACAA GAGAATTACC TCATCATTCA
1561 CAAGCGAAGT CCAAAGCTAA GTGTAATCAA CGAATAAGTG TGCCTGTGGT TTGGCTGTCA
```

FIGURE 4A

```
1621 ATGAAAAGTG TGTGTCAGGG GGGTTAACAG TCATTGCAAA GGTGTGTGTC AGGGGGAACT
1681 GATCGCCTCT CTGGCAAGGT GTGTGTCAGG GGGGAATGCC ACTGGCAAGG TGTGCGTCAG
1741 GGGGAAAATT GGTGGTTTTC CCTCCGAGTG AGTATCACGG GGCGTAATTA TCACCGGTAA
1801 AGTGTGTGTC AGGGGAAGG AATTGGCTTT CGTTCGGTGT GTGCCAAGGG GTTTGACGGG
1861 AATTCGGGAT CCCGAACGGC CAGATGCAAC TTTCGCCATA TACGACGGCG TTCCTGCCA
1921 TGCTTTTTGA CTTTCCACTC GCCTTCACCG AAGACCTTCA GCCCGGTGAA ATCAATTACC
1981 AGGTGTGCGA TTTCACCCCG GGTGGGCGTT TTGAAACTGA CATTAACCGA CTTTGCCCGC
2041 CTGCTGACAC AGCTGTAATC CGGGCAGCGT AGCGGAACGT TCATCAGAGA AAAAATGAA
2101 TCAATAAAGC CCTGCGCAGC GGGCAGGGTC AGCCTGAATA CGCGTTTAAT GACCAGCACA
2161 GTCGTGATGG CAAGGTCAGA ATAGCGCTGA GGTCTGCCTC GTGAAGAAGG TGTTGCTGAC
2221 TCATACCAGG CCTGAATAGC TTCATCATCC AGCCAGAAAG TTATGGAGCC ACGGTTGATG
2281 AGGGCTTTAT TGTAGGTGGG CCAGTTGGTG ATTTTGAACT TTTGCTTTGC CACGGAACGG
2341 TCTGCGTTGT CGGGAAGATG CGTGATCTGA TCCTTCAACT CAGCAAAAGT TCGATTTATT
2401 CAACAAAGCC CGTTGTGTCT CAAAATCTCT GATGTTACAT TGAACAAGAT AAAAGTATAT
2461 CATCATGAAC AATAAAACTG TCTGCTTACA TAAACAGTAA TACAAGGAGC GTTATGAGCC
2521 ATATTCAACG GGAGACGTCT TGCTCGAGGC CGCGATTAAA TTCCAACCTG GATGCTGATT
2581 TATATGGGTA TAGATGGGCT CGCGATAATG TCGGGCAATC AGTGCGACA ATCTATCGAT
2641 TGTATGGGAA GCCCGATGCG CCAGAGTTGT TTCTGAAACA TGGCAAAGGT AGCGTTGCCA
2701 ATGATGTTAC AGATGAGATG GTCAGACTAA ACTGGCTGAC GGCATTATG CCTCTTCCGA
2761 CCATCAAGCA TTTTATCCGT ACTCCTGATG ATGCATGGTT ACTCACCACT GCGATCCCCG
2821 GGAAAACAGC ATTCCAGGTA TTAGAAGAAT ATCCTGATTC AGGTGAAAAT ATTGTTGATG
2881 CGCTGGCAGC GTTCCTGCGC CGGTTGCATT CGATTCCTGT TTGTAATTGT CCTTTTAACA
2941 GCGATCGCGT ATTTCGTCTC ACTCAGGCGC AATCACGAAT GAATAACGGT TTGGTTGATG
3001 CGAGTGATTT TGATGACGAG CGTAATGGCT GGCCTGTTGA ACAAGTCTGG AAAGAAATGC
3061 ATAAGCTTTT GCCATTCTCA CCGGATTCAG TCGTCACTCA TGGTGATTTC TCACTTGATA
3121 ACCTTATTTT TGACGAGGGG AAATTAATAG GTTGTATTGA TGTTGGACGA GTCGGAATCG
3181 CAGACCGATA CCAGGATCTT GCCATCCTAT GGAACTGCCT CGGTGAATTT TCACCTTCAT
3241 TACAGAAACG GTTTTTTAT AAATATGGCA TTGATATGAA TCGGTGAATTT AAATTGCAGT
3301 TTCATTTGAT GCTCGATGAG TTTTTCTGAT AGCTAGTCTT TGGTTTCCCT GTCCGG
```

```
     740       750       760       770       780       790
      |         |         |         |         |         |
ATGGAAACTCAACTAGTTATATCTGATGTGTTATTTGGTAACACGGAAGAAAAACAAAAA
METGluThrGlnLeuValIleSerAspValLeuPheGlyAsnThrGluGluLysGlnLys
```

```
     800       810       820       830       840       850
      |         |         |         |         |         |
CCATTAACAGTTAATGAACTGAATACAATTCAACCAGTGGCCTTTATGCGCCTTGGCCTG
ProLeuThrValAsnGluLeuAsnThrIleGlnProValAlaPheMETArgLeuGlyLeu
```

```
     860       870       880       890       900       910
      |         |         |         |         |         |
TTTGTGCCTAAACCATCAAGGTCATCTGACTACAGCCCGATGATTGATGTCAGTGAATTA
PheValProLysProSerArgSerSerAspTyrSerProMETIleAspValSerGluLeu
```

```
     920       930       940       950       960       970
      |         |         |         |         |         |
AGTTCTACCTTTGAATTTGCAAGACTTGAGGGGTTTACTGACATAAAAATCACTGGTGAA
SerSerThrPheGluPheAlaArgLeuGluGlyPheThrAspIleLysIleThrGlyGlu
```

```
     980       990       1000      1010      1020      1030
      |         |         |         |         |         |
CGTCTTGATATGGATACTGATTTCAAGGTGTGGATCGGCATAGTCAAAGCGTTCAGCAAG
ArgLeuAspMETAspThrAspPheLysValTrpIleGlyIleValLysAlaPheSerLys
```

```
     1040      1050      1060      1070      1080      1090
      |         |         |         |         |         |
TACGGGATTTCGTCAAACCGCATCAAACTAAAGTTTTCTGAGTTCGCAAAAGATTGTGGT
TyrGlyIleSerSerAsnArgIleLysLeuLysPheSerGluPheAlaLysAspCysGly
```

```
     1100      1110      1120      1130      1140      1150
      |         |         |         |         |         |
TTCCCCGGTAAAAAACTGGACAAGAAACTGAGAGCGCATATAGATGAATCGCTTCGTAAA
PheProGlyLysLysLeuAspLysLysLeuArgAlaHisIleAspGluSerLeuArgLys
```

```
     1160      1170      1180      1190      1200      1210
      |         |         |         |         |         |
ATCAGGGGGAAATCGATCTCATTTAAGCGAGGCAAAGATTCACAATCTGCATATCATACC
IleArgGlyLysSerIleSerPheLysArgGlyLysAspSerGlnSerAlaTyrHisThr
```

FIGURE 5B

```
        1220      1230      1240      1250      1260      1270
          |         |         |         |         |         |
    GGCCTCATAAAGATAGCCTATTTCAATGCCGATACAGACGTTGTGGAACTGGAAGCAGAC

GlyLeuIleLysIleAlaTyrPheAsnAlaAspThrAspValValGluLeuGluAlaAsp 1280      1290      1300      1310      1320      1330
          |         |         |         |         |         |
    GAGCGATTATGGGAGTTATACTACTTTGATTATCGTGTTGTTCTTCAACTACATGCAATA

GluArgLeuTrpGluLeuTyrTyrPheAspTyrArgValValLeuGlnLeuHisAlaIle 1340      1350      1360      1370      1380      1390
          |         |         |         |         |         |
    AAAGCCCTTCCACGTCTAGAAGTTGCACAAGCCCTGTATACCTTCCTTGCAAGCCTTCCA

LysAlaLeuProArgLeuGluValAlaGlnAlaLeuTyrThrPheLeuAlaSerLeuPro 1400      1410      1420      1430      1440      1450
          |         |         |         |         |         |
    AGTAACCCGGCTCCTATCTCTTTTAAACGCCTACGTGAAAGGTTGTCTCTGATCAGTCAG

SerAsnProAlaProIleSerPheLysArgLeuArgGluArgLeuSerLeuIleSerGln 1460      1470      1480      1490      1500      1510
          |         |         |         |         |         |
    GTTAAAGAACAGAATCGAATAATCAAAAAGCGATTACTAAGCTGATAGATATCGGCTAT

ValLysGluGlnAsnArgIleIleLysLysAlaIleThrLysLeuIleAspIleGlyTyr 1520      1530      1540      1550      1560      1570
          |         |         |         |         |         |
    TTGGACGCTTCTATGGTGAAAAAAGGACAAGAGAATTACCTCATCATTCACAAGCGAAGT

LeuAspAlaSerMETValLysLysGlyGlnGluAsnTyrLeuIleIleHisLysArgSer 1580      1590      1600
          |         |         |
    CCAAAGCTAAGTGTAATCAACGAATAA

ProLysLeuSerValIleAsnGlu---
```

```
From:
              10         20         30         40         50         60
              --         --         --         --         --         --
   1  GATCCCGAGC TTATCAGATG TATTCTGATG CGGTTCGATA AACCTGTCTT ACCAGAAAGG
  61  GAACAAACTC AGATGAAAAT CATCAAAATC TATACACCTC ATGAACTGGC TCTGTTGAGA
 121  GATCCTGCTT TCAGATTGAT AGTGATAGAG GCTATTGGTA CAGATGGATT CGTTGAGCAA
 181  TATAATCTAC TAAATAATGT CTCACTTAAT CAGCCTAAGA ACGGTCTGGA GGTATTAATC
 241  GATCAGGCTA CAGGGCAGC  AGATAAGCAT CAACGCGTAT ACTTCAACGG ACTTCTTAAA
 301  TTTATCTATG AAACTGTAGA CTTACGGTTA GAACCGATGG CTTTGGGGTA GTTCCGGGAA
 361  CCGTTGTCGG GTAATGAATG GGTTTACCTT TCATTGCCCG GCAGCGGTTG GACAAGCGTA
 421  GCGCGTCAGA TATTCCTCCA CATTACCATC ATTTAAAGTT ATCCACATAT CCACCGTGTA
 481  GATCCAATAA TAGATCCATA GAGAGATCCA GATAAAACCA AAAAGATCCC CGTGGTCTGT
 541  AGCCTTACTG CCAAGGCT   TACAACGTTT TTCGGTGTGT GCTGAGGGGA AAAAGGTGTG
 601  TGCTGAGGGG AAGAAAGTGT GTGTTACGGG GATTTGGGTG TGTGCTGAGG GGAAAAAAGG
 661  TGGGCGTCAC GGGAAAATG  TGATACTTTT CCACAATCGT AGCATTTACG TGGGGGGAA
 721  TTATTTATT  ATGGAAACTC AACTAGTTAT ATCTGATGTG TTATTTGGTA ACACGGAAGA
 781  AAAACAAAAA CCATTAACAG TTAATGAACT GAATACAATT CAACCAGTGG CCTTTATGCG
 841  CCTTGGCCTG TTTGTGCCTA AACCATCAAG GTCATCTGAC TACAGCCCGA TGATTGATGT
 901  CAGTGAATTA AGTTCTACCT TTGAATTTGC AAGACTTGAG GGGTTTACTG ACATAAAAAT
 961  CACTGGTGAA CGTCTTGATA TGGATACTGA TTTCAAGGTG TGGATCGGCA TAGTCAAAGC
1021  GTTCAGCAAG CGTCCGGATT TGTCAAACCG CATCAAACTA AAGTTTTCTG AGTTCGCAAA
1081  AGATTGTGGT TTCCCCGGTA AAAAACTGGA CAAGAAACTG AGAGCGCATA TAGATGAATC
1141  GCTTCGTAAA ATCAGGGGGA AATCGATCTC ATTTAAGCGA GGCAAAGATT CACAATCTGC
1201  ATATAATACC GGCCTCATAA AGATAGCCTA TTTCAATGCC GATACAGACG TTGTGGAACT
1261  GGAAGCAGAC GAGCGATTAT GGGAGTTATA CTACTTTGAT TATCGTGTTG TTCTTCAACT
1321  ACATGCAATA AAAGCCCTTC CACGTCTAGA AGTTGCACAA GCCCTGTATA CCTTCCTTGC
1381  AAGCCTTCCA AGTAACCCGG CTCCTATCTC TTTTAAACGC CTACGTGAAA GGTTGTCTCT
1441  GATCAGTCAG GTTAAAGAAC AGAATCGAAT AATCAAAAAA GCGATTACTA AGCTGATAGA
1501  TATCGGCTAT TTGGACGCTT CTATGGTGAA AAAAGGACAA GAGAATTACC TCATCATTCA
1561  CAAGCGAAGT CCAAAGCTAA GTGTAATCAA CGAATAAGTG TGCCTGTGGT TTGGCTGTCA
1621  ATGAAAAGTG TGTGTCAGGG GGGTTAACAG TCATTGCAAA GGTGTGTGTC AGGGGAACT
1681  GATCGCCTCT CTGGCAAGGT GTGTGTCAGG GGGAATGCC  ACTGGCAAGG TGTGCGTCAG
```

```
1741 GGGGAAAATT GGTGGTTTTC CCTCCGAGTG AGTATCACGG GGCGTAATTA TCACCGGTAA
1801 AGTGTGTGTC AGGGGAAGG AATTGGCTTT CGTTCGGTGT GTGCCAAGGG GTTTGACGGG
1861 AATTCGGGAT CCCGAACGC CAGATGCAAC TTTCGCCATA TACGACGGCG TTCCTGGCCA
1921 TGCTTTTTGA CTTTCCACTC GCCTTCACCG AAGACCTTCA GCCCGGTGA ATCAATTACC
1981 AGGTGTGCGA TTTCACCCCG GGTGGGCGTT TTGAAACTGA CATTAACCGA CTTTGCCCGC
2041 CTGCTGACAC AGCTGTAATC CGGGCAGCGT AGCGGAACGT TCATCAGAGA AAAAATGGAA
2101 TCAATAAAGC CCTGCGCAGC GCGCAGGGTC AGCCTGAATA CGGGTTTAAT GACCAGCACA
2161 GTCGTGATGG CAAGGTCAGA ATAGCGCTGA GGTCTGCCTC GTGAAGAAGG TGTTGCTGAC
2221 TCATACCAGG CCTGAATAGC TTCATCATCC AGCCAGAAAG TTATGGAGCC ACGGTTGATG
2281 AGGGCTTTAT TGTAGGTGGG CCAGTTGGTG ATTTTGAACT TTTGCTTTGC CACGGAACGG
2341 TCTGCGTTGT CGGGAAGATG CGTGATCTGA TCCTTCAACT CAGCAAAAGT TCGATTTATT
2401 CAACAAAGCC CGTTGTGTCT CAAAATCTCT GATGTTACAT TGAACAAGAT AAAAGTATAT
2461 CATCATGAAC AATAAAACTG TCTGCTTACA TAAACAGTAA TACAAGGAGC GTTATGAGCC
2521 ATATTCAACG GGAGACGTCT TGCTCGAGGC CGCGATTAAA TTCCAACCTG GATGCTGATT
2581 TATATGGTA TAGATGGGCT CGCGATAATG TCGGGCAATC AGGTGCGACA ATCTATCGAT
2641 TGTATGGGAA GCCCGATGCG CCAGAGTTGT TTCTGAAACA TGGCAAAGGT AGCGTTGCCA
2701 ATGATGTTAC AGATGAGATG GTCAGACTAA ACTGGCTGAC GGCATTTATG CCTCTTCCGA
2761 CCATCAAGCA TTTTATCCGT ACTCCCTGATG ATGCATGGTT ACTCACCACT GCGATCCCCG
2821 GGAAAACAGC ATTCCAGTA TTAGAAGAAT ATCCTGATTC AGGTGAAAAT ATTGTTGATG
2881 CGCTGGCAGC GTTCCTGCGC CGGTTGCATT CGATTCCTGT TTGTAATTGT CCTTTTAACA
2941 GCGATCGCGT ATTTCGTCTC ACTCAGGCGC AATCACGAAT GAATAACGGT TTGGTTGATG
3001 CGAGTGATTT TGATGACGAG CGTAATGGCT GGCCTGTTGA ACAAGTCTGG AAAGAAATGC
3061 ATAAGCTTTT GCCATTCTCA CCGGATTCAG TCGTCACTCA TGGTGATTTC TCACTTGATA
3121 ACCTTATTTT TGACGAGGGG AAATTAATAG GTTGTATTGA TGTTGGACGA GTCGGAATCG
3181 CAGACCGATA CCAGGATCTT GCCATCCTAT GGAACTGCCT CGGTGAATTT TCACCTTCAT
3241 TACAGAAACG GCTTTTTTAT AAATATGGCA TTGATAATCC TGATATGAAT AAATTGCAGT
3301 TTCATTTGAT GCTCGATGAG TTTTTCTGAT AGCTAGTCTT TGGTTTCCCT GTCCGG
```

FIGURE 7A

```
         740       750       760       770       780       790
          |         |         |         |         |         |
ATGGAAACTCAACTAGTTATATCTGATGTGTTATTTGGTAACACGGAAGAAAAACAAAAA
METGluThrGlnLeuValIleSerAspValLeuPheGlyAsnThrGluGluLysGlnLys 800       810       820       830       840       850
          |         |         |         |         |         |
CCATTAACAGTTAATGAACTGAATACAATTCAACCAGTGGCCTTTATGCGCCTTGGCCTG
ProLeuThrValAsnGluLeuAsnThrIleGlnProValAlaPheMETArgLeuGlyLeu 860       870       880       890       900       910
          |         |         |         |         |         |
TTTGTGCCTAAACCATCAAGGTCATCTGACTACAGCCCGATGATTGATGTCAGTGAATTA
PheValProLysProSerArgSerSerAspTyrSerProMETIleAspValSerGluLeu 920       930       940       950       960       970
          |         |         |         |         |         |
AGTTCTACCTTTGAATTTGCAAGACTTGAGGGGTTTACTGACATAAAAATCACTGGTGAA
SerSerThrPheGluPheAlaArgLeuGluGlyPheThrAspIleLysIleThrGlyGlu 980       990      1000      1010      1020      1030
          |         |         |         |         |         |
CGTCTTGATATGGATACTGATTTCAAGGTGTGGATCGGCATAGTCAAAGCGTTCAGCAAG
ArgLeuAspMETAspThrAspPheLysValTrpIleGlyIleValLysAlaPheSerLys 1040      1050      1060      1070      1080      1090
          |         |         |         |         |         |
TACGGGATTTCGTCAAACCGCATCAAACTAAAGTTTTCTGAGTTCGCAAAAGATTGTGGT
TyrGlyIleSerSerAsnArgIleLysLeuLysPheSerGluPheAlaLysAspCysGly 1100      1110      1120      1130      1140      1150
          |         |         |         |         |         |
TTCCCCGGTAAAAAACTGGACAAGAAACTGAGAGCGCATATAGATGAATCGCTTCGTAAA
PheProGlyLysLysLeuAspLysLysLeuArgAlaHisIleAspGluSerLeuArgLys 1160      1170      1180      1190      1200      1210
          |         |         |         |         |         |
ATCAGGGGGAAATCGATCTCATTTAAGCGAGGCAAAGATTCACAATCTGCATATAATACC
IleArgGlyLysSerIleSerPheLysArgGlyLysAspSerGlnSerAlaTyrAsnThr
```

FIGURE 7B

```
       1220        1230        1240        1250        1260        1270
         |           |           |           |           |           |
GGCCTCATAAAGATAGCCTATTTCAATGCCGATACAGACGTTGTGGAACTGGAAGCAGAC
GlyLeuIleLysIleAlaTyrPheAsnAlaAspThrAspValValGluLeuGluAlaAsp 1280        1290        1300        1310        1320        1330
         |           |           |           |           |           |
GAGCGATTATGGGAGTTATACTACTTTGATTATCGTGTTGTTCTTCAACTACATGCAATA
GluArgLeuTrpGluLeuTyrTyrPheAspTyrArgValValLeuGlnLeuHisAlaIle 1340        1350        1360        1370        1380        1390
         |           |           |           |           |           |
AAAGCCCTTCCACGTCTAGAAGTTGCACAAGCCCTGTATACCTTCCTTGCAAGCCTTCCA
LysAlaLeuProArgLeuGluValAlaGlnAlaLeuTyrThrPheLeuAlaSerLeuPro 1400        1410        1420        1430        1440        1450
         |           |           |           |           |           |
AGTAACCCGGCTCCTATCTCTTTTAAACGCCTACGTGAAAGGTTGTCTCTGATCAGTCAG
SerAsnProAlaProIleSerPheLysArgLeuArgGluArgLeuSerLeuIleSerGln 1460        1470        1480        1490        1500        1510
         |           |           |           |           |           |
GTTAAAGAACAGAATCGAATAATCAAAAAGCGATTACTAAGCTGATAGATATCGGCTAT
ValLysGluGlnAsnArgIleIleLysLysAlaIleThrLysLeuIleAspIleGlyTyr 1520        1530        1540        1550        1560        1570
         |           |           |           |           |           |
TTGGACGCTTCTATGGTGAAAAAAGGACAAGAGAATTACCTCATCATTCACAAGCGAAGT
LeuAspAlaSerMETValLysLysGlyGlnGluAsnTyrLeuIleIleHisLysArgSer 1580        1590        1600
         |           |           |
CCAAAGCTAAGTGTAATCAACGAATAA
ProLysLeuSerValIleAsnGlu---
```

```
                900                        920                        940                        960
ATT AAA ATC ACC GGT CCT CGA CTC GAT ATG GAT ACT GAT TTC AAA ACG TGG ATC GGT GTC ATC TAC GCG TTC AGC AAA TAC GGC TTG TCC
ile lys ile thr gly pro arg leu asp met asp thr asp phe lys thr trp ile gly val ile tyr ala phe ser lys tyr gly leu ser
                                          ⓓ⋯⋯⋯⋯>                                                                    ⓒ⋯⋯>
           980                        1000                       1020                       1040                       1060
TCA AAC ACC ATC CAG TTA TCG TTT CAG GAA TTC GCT AAA GCC TGT GGT TTC CCC TCA AAA CGT CGT GAT GCG AAA CTG CGT TTA ACC ATT
ser asn thr ile gln leu ser phe gln glu phe ala lys ala cys gly phe pro ser lys arg arg asp ala lys leu arg leu thr ile
                       ⓑ⋯⋯⋯⋯>
                   ⓒ⋯⋯⋯⋯⋯⋯>
                         1100                       1120                       1140
CAT GAA TCA CTT GGA CGC TTG CGT AAC AAG GGT ATC GCT TTT AAG CGC GGA AAA GAT GCT AAA GGC GGT TAT CAG ACT GGT CTG CTG AAG
his glu ser leu gly arg leu arg asn lys gly ile ala phe lys arg gly lys asp ala lys gly gly tyr gln thr gly leu leu lys
         1160                       1180                       1200                       1220                       1240
GTC GGG CGT TTT GAT GCT GAC CTT GAT CTG ATA GAG GCT CTG GAG CTG TTC AAG TTG TGG GAG CTG TTC ATC GAA AGC CTT GAT TAT CGC GTT CTG
val gly arg phe asp ala asp leu asp leu ile glu ala leu glu leu phe lys leu trp glu leu phe ile glu ser leu asp tyr arg val leu
                        1260                       1280                       1300                       1320
TTG CAA CAC CAC GCC TTG CGT GCC CTT CCG AAG AAA GAA GCT GCA CAA GCA ATT TAC ACT TTC ATT CCG CAA AAC CTT CCG AAC CCG TTG
leu gln his his ala leu arg ala leu pro lys lys glu ala ala gln ala ile tyr thr phe ile glu ser leu pro gln asn pro leu
                                                                                                             ⓔ⋯⋯⋯⋯>
          1340                       1360                       1380                       1400                       1420
CCG CTA TCG TTC GCG CGA ATC CGT GAG CGC CTG GCT TTG CAG TCA CAG CTT GGC GAG CAA AAC CGT ATC ATT AAG AAA GCG ATA GAA CAG
pro leu ser phe ala arg ile arg glu arg leu ala leu gln ser gln leu gly glu gln asn arg ile ile lys lys ala ile glu gln
                    1440                       1460                       1480                       1500
CTT AAA ACA ATC GGC TAT CTC GAC TGT CTC ATT GAG AAG AAA GGC CGG GAA AGT TTT GTA ATC GTC CAT TCT CGC AAT CCA AAG CTG AAA
leu lys thr ile gly tyr leu asp cys ser ile glu lys lys gly arg glu ser phe val ile val his ser arg asn pro lys leu lys
```

FIG. 10A

FIGURE 12A

```
         10         20         30         40         50         60         70         80         90
AAGCTTATCAGATGTATTCTGATGCGGTTCGATAAACCTGTCTTACCAGAAAGGGAACAAACTCAGATGAAAATCATCAAAATCTATACACCTCATGAAC    100

TGGCTCTGTTGAGAGATCCTGCTTTCAGATTGATAGAGGCTATTGGTACAGATGATTCGTTGAGCAATATAATCTACTAAATAATGTCTCACT           200

TAATCAGCCTAAGAACGGTCTGGAGGTATTAATCGATCAGCCTACAGGGGCAGCAGATAAGCATCAACGCGTATACTTCAACGGACTTCTTAAATTTATC    300

TATGAAACTGTATACTTACGGTTAGAACCGATGGCTTTGGGGTAGTTCCGGGAACCGTTGTGCGGTAATGAATGGGTTTACCTTTCATTGCCCGGCAGCG    400
                                                        ───────────────────────────────→

GTTGGACAAGCGTAGCGCGGTCAGATATTCCTCCACATTACCATCATTTAAAG TATCCACA TATCCACCGTGTA GATC CATAGAGA GA             500
                                                    ←───────────────────
                                                         DnaA box T CAGATAAACCAAAA GATC CCCGTGGTCTCTGTAGCCTTACTGCCACAAGCTTACACGTTTTTCGGTGTGTGCTGAGGGGAAAAAGTGTGTGCTGA      600
                                                                                    <- - - -

GGGGAAGAAAGTGTGTTACGGGGATTTGGGTGTGTGCTGAGGGGAAAAAGGTGGGCGTCACC GGAA AATGTGATACTTTC CACAAT CGTAGCATT       700
                                                              - - - ->                -10

TACGTGGGGGAATTATTTTAT ATG GAAACTCAACTAGTTATATCTGATGTGTTATTGGTAACACGGAAGAAAACAGCATTAACAGTTAATG             800
                      -35

AACTGAATACAATTCAACCAGTGGCCTTGCCTGTTTGTGCCTAAACCATCAAGTCATCTGACTACAGCCCGATGATTGATGTCAGTGA                 900

ATTAAGTTCTACCTTTGAATTGCAAGACTTGAGGGGTTTACTGACATAAAATCACTGGTGAACGTCTTGATATGGATACTGATTTCAAGGTGTGGATC     1000

GGCATAGTCAAAGCGTTCAGCACAAGTACGGGGATTTGTCAAACCGATCAAACTAAAGTTTTCTGAGTTCGCAAAAGATTGTGTTTCCCCGTAAAAAAC    1100

TGGACAAGAAACTGAGAGCGCATATAGAGAATCGCTTCGTAAAATCAGGGGAAATCGATCTCATTTAAGCGAGGCAAAGATTCACAATCTGCATATCA    1200
```

FIGURE 12B

```
TACCCGGCCTCATAAAGATAGCCTATTTCAATGCCGATACAGACGAGCGATTATGGAGTTATACTTTGATTATCGT      1300
GTTGTTCTTCAACTACATGAATAAAGCCCTTGCACGTCTAGAAGTTGCACAGCCCTGTATACCTTCCTTGCAAGT      1400
TCTCTTTTAAACGCCTACGTGAAAGGTTGTCTCTGATCAGGTTAAAGAACAGAATAATCAAAAAAGCGATTACTAAGCTGATAGATATCGG      1500
CTATTTGGACGCTTCTATGGTGAAAAAGGACAAGAGAATTACCTCATCATTCACAAGCCAAGTCCAAAGCTAATCAACGAATAAGTGTGCCTG      1600
        *
(A)
TGGTTTGGCTGTCAATGAAATGAAAAGTGTGTCAGGGGGGTTAACAGTCATTGCAAAGTGTGTCAGGGGAACTGATCGCCCTCTCGGCAAGGTGTGT      1700
                                          *
                                        (G) (−)
CAGGGGGAATGCCACTGGCAAGGTGCGTCAGGGGAAAATTGGTGGTTTCCCTCCGAGTGAGTATCACGGGGGCGTAATTATCACCGGTAAAGTGTG     1800
  (−)                                    *
                                        (G)
TGTCAGGGGAAGGAATTGGCTTTCGTTCGGTGTGTGCCAAGGGGTTTGACGGGAATTC       1859
                                       *  *
                                      (A) (A)
```

FIGURE 15A

```
1          10         20         30         40         50         60         70         80         90
AAGCTTCAACGAAAAAATAAATGAAAGATGTTCCGAGTTACTGGCCTTAGTGCTGGTTTTTTGTGTAGTGATCGGGGTTACTGCGCCCTCCCAG    100
HindIII CCACCAGCAGCACGGTTGCCTATCTATATCATACCCGCCTTGCGCGCGGGTTTTTTCTTTTCTGAGAACCGGTAGTACCGGTTCGGCTGATGCCC    200

CTATGCAGTTTCGCATTCAGGATCAAGGTACAGGACTGAAAAGGGATTCAGTGTAAGGATCTTGATGGGCTGGCAGGACACCAGTGTAAAACAGTTTTT    300
                                                                                           ORF-1
CGTTTCGGCGGGCTCTTGGTGACCGTTCTTGTTCATGATACCTTATTCATATAGTGTATGAATAAGGTGTTTTAGCCGAACTTAACAGGAGCATGAACAT    400
                 BstEII                                                                  S.D.

CACCACTCATCAGGAAACACTGCCGCTTTGATCGACGCACTGAATGATTGACCCTTCCGACGTTCCGTTGCCATCTATGCCGGGTTTTGAC    500
                                        MaeII

CGTGATAGCGTGAATGAGCTGGTGGAGAGCTCGGCAAGAGATTAAGCAGCTTGTGAAGTGACGTTCTACCTGCCGGAACCTACCAGACATCCTGTG    600
                                                   MaeII

AAGAAGAGTGAGAAATATCTTGCCCTCAAGAGGTTCGGGCAGTAATGTCGGCAGCAATGTGAGCATCTGAGACTGAGAT    700

TTTAGGTGGAAAGTGCCGCTGAGTAAGATCACCATAGAGCCCGGCTAAGCCGGGTTTTTCTTTTTGCAGGCTACGATCTACCCTGACCCCTCAAGTTCTT    800
                                                                                           ORF-2
ATCAACTCCCCCACTATCCATATACCTCTCTGTATTGCACATCGTGTAATATCGCGTATAGTATTACACACCATGTAATACAGAGATGGCCGATGATAAA    900
                                    -35   DraIII                -10                        S.D.

ATCTTTCAAGCACAAAGGATTGAAACTGCTTTTGAAAAGGGTGTTACTTCTGGTGTGCCTGCGCAAGATGTAGACAGAATCAATGACCGTTTGCAGGCC    1000
```

FIGURE 15B

```
ATCGATACAGCGACGAGAGATTGGTGAACTAAACCCGCCAGATTACAAATTACATCCATTAAAGGGGGATCGGGAAGGTTACTGGTCTATCACTGTCCGGG  1100
ClaI                                                    ORF-3
CGAATTGGCGCCATTACTTTTCAGTTCATTAAGCGTGATGCTTACATTTTAAATTATGAGGATTATCACTAATGAGACAATTCAAGTTTCACATCCGGGT  1200
                                                    S.D.
GAGATGATAGCCCCGCGATTTAGAGGATGAGTGAGTGGTCGTCGTTTTGCTCACAATATTGGTGTACACCAGCAACCGTATCCCGTCTACTTGCGG  1300

GGAAAACTGCGTTGACCCCTTCTCTTTCGATTCGTATTGCTGCGGAGTACGCCCTGAGTTTTGGTTACGGCTACAGAGCAATTATGATCTGCCG  1400

CCAGTTAGAAAACCAAATCGATACATCCGGGATGTCTTGTAGGGTGAGTCGAAGCAACAGCAGCAGAACGCGCAAGAGACATTAATTAATTTCTGATGCG  1500
      <---------
AGGCCACCAGCCCTGCATCAGCTACCCTGAGCCCTAATAGCTTTATCCTGCCAACTTTCTCTTACCCTCCGGGTGATTTCTTACAAGCTT  1590
                                                                              HindIII
```

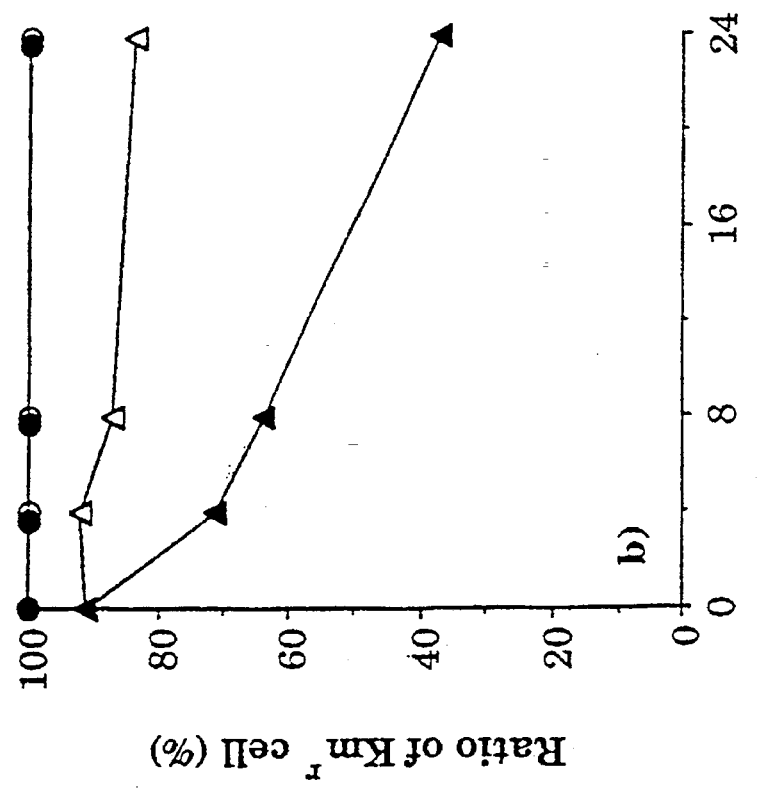
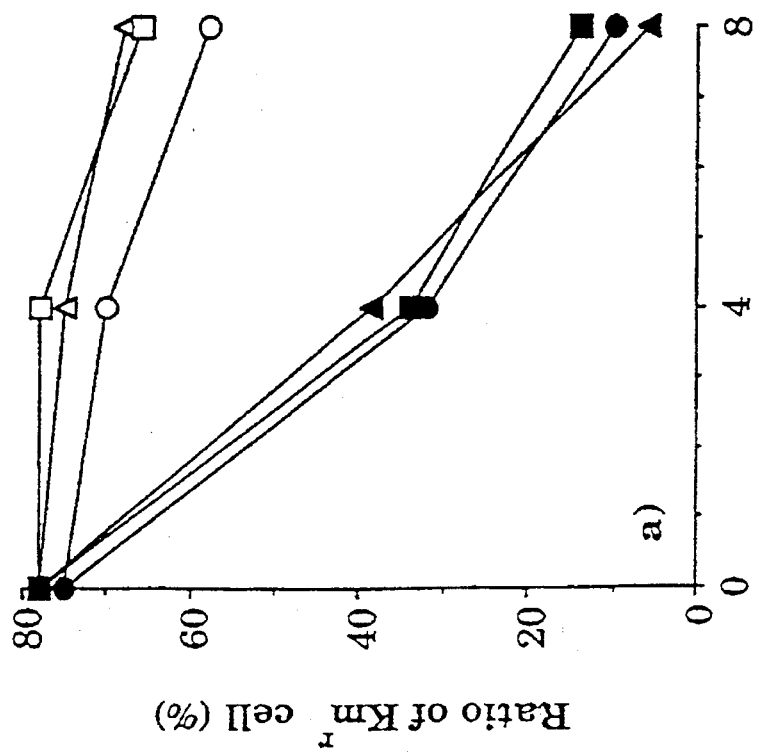
FIG. 16A
FIG. 16B

MUTATION OF REPA PROTEIN

BACKGROUND OF THE INVENTION

Rts1 is a high-molecular weight drug resistance factor which has a molecular weight of $126 \times 10^6$ daltons and confers resistance to kanamycin. In addition to conferring kanamycin resistance ($Km^r$), the plasmid exhibits unusual temperature-sensitive phenotypes, which affect plasmid maintenance and replication, as well as host cell growth. These phenotypes include growth inhibition of gram negative bacteria harboring the plasmid at 42° C., but not at 32° C. (the so-called tsg, temperature sensitive growth). In addition, E. coli cells harboring the plasmid allow T4 phage growth at 42° C., yet phage growth is restricted at 32° C. Furthermore, the replication cycle of this plasmid at 42° C. appears to bypass the typical covalently closed circular (CCC) form and proceeds (the so-called Tsc phenotype, temperature sensitive circular DNA formation). At 42° C., but not at 32° C., conjugative transfer of Rts1 is inhibited. Finally, prolonged incubation of bacteria harboring this plasmid at 42° C. results in plasmid loss from host cells (the so-called Tdi, temperature dependent instability).

The nucleotide sequence of Rts1 has been elucidated, and partial nucleotide sequences have been reported, including those regions involved in DNA replication, incompatibility, kanamycin resistance and temperature-dependent instability of the plasmid. A particular region of the plasmid, known as the "repA" region has been identified and the sequence elucidated. The repA protein has been shown to be important in determining the copy number of the Rts1 plasmid maintained in a host cell. Mutated Rts1 plasmids having mutations in the repA region have been described, but induce only a moderate change in the copy number of the plasmid (i.e. at most 5 to 10-tenfold increases).

A second plasmid, known as P1, has been described in the art and contains a similar repA region.

No mutants of these two plasmids, however, are known in the art which induce significant increased copy numbers or which are easily controllable by changes in growth media.

OBJECTS AND SUMMARY OF THE INVENTION

It is, therefore, one object of the present invention to provide Rts1 and P1 mutants which provide for high copy numbers of the plasmid in a host bacteria.

It is another object of the present invention to provide mutant plasmids of Rts1 and P1 which can coexist with other vectors in a host bacteria, such as E. coli.

It is a still further object of the present invention to provide mutant Rts1 and P1 plasmids wherein the copy numbers of the plasmid are controllable, within the range of about 20 to 120, by the use of different host bacteria growth medium.

It is yet a further object of the present invention to provide P1 and Rts1 plasmid mutants which can be removed from a host bacteria by a simple shift in the bacteria growth temperature.

Finally, yet a further object of the present invention is to provide mutants of P1 and Rts1 plasmids wherein the slight instability at 42° C. is corrected with the addition of a defined DNA fragment.

These and other objects of the present invention are accomplished by providing mutants of the plasmids Rts1 and P1 which are mutated at a single amino acid position in the repA region. The single point mutant plasmids provide significantly and unexpectedly improved advantages as compared to the wild type plasmid.

BRIEF DESCRIPTION OF THE DRAWINGS

FIG. 3 shows the results of stability tests on pOK and pOKcop.

FIG. 4 shows the nucleotide sequence (SEQ. ID NO. 1) of the plasmid pOK.

FIG. 5 shows the nucleotide sequence (SEQ. ID NO. 2) of the repA portion of the plasmid pOK.

FIG. 6 shows the nucleotide sequence (SEQ. ID NO. 4) of the mutant plasmid pOKcop.

FIG. 7 shows the nucleotide sequence (SEQ. ID NO. 5) of the repA portion of pOKcop.

FIG. 10 shows the sequence of the replication region of the mutant P1 (SEQ. ID NO. 10).

FIG. 12 shows the nucleotide sequence of the replication region of Rts1 (SEQ. ID NO. 13).

FIG. 15 shows the nucleotide sequence (SEQ. ID NO. 14) of the $GH_3$ fragment which stabilizes pOK at 42.5° C.

FIG. 16 shows results of studies on the stabilizing $GH_3$ fragment evidencing success only with cis configuration.

DETAILED DESCRIPTION OF THE INVENTION

Figure 1:
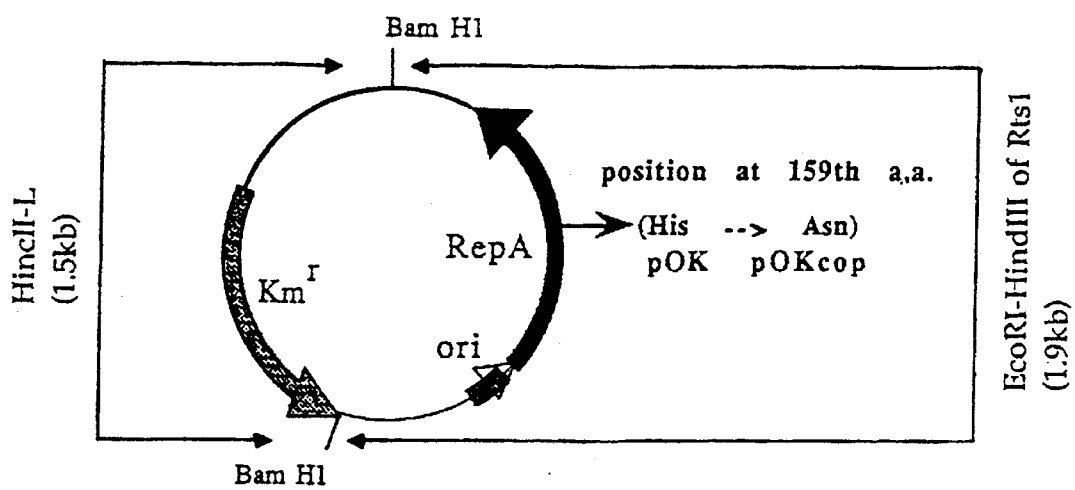
FIG. 1 shows the configuration of the plasmids pOK and pOKcop.

Some of the procedures described below reference publications known to those skilled in the art, each of which is hereby expressly incorporated by reference.

1. The Rts1 Mutant

A copy number mutant of the Rts1 replication unit (copy number 1–2copy/cell) was obtained and the sequencing of the replicon of this plasmid indicated a one-base substitution in the repA region resulting in amino acid change from histidine to asparagine at 159th position. The copy number of a plasmid with this mutant replicon increased 120 fold as compared with that containing the wild type replicon. The copy number of the plasmid with the mutated replicon was very much influenced by the culture conditions while the wild type replicon was not. In addition, the plasmid with the wild type replicon was unstable at 42.5° C., while the plasmid with the mutated replicon was stabilized to a large extent.

Rts1 is a high-molecular-weight drug resistance factor which confers kanamycin resistance (Km$^r$) and expresses various temperature-sensitive phenotypes. The following procedures produce a small derivative plasmid (pOK) of Rts1. Plasmid pOK consists of the replication region (1.9 kb) and the kanamycin resistance gene fragment (1.5 kb) of Rts1. The copy mutant pOKcop can be obtained by screening for pOK mutants which still gives resistance to kanamycin at 42.5° C. This is because the mutant, due to a large copy, can stay in the cell resulting in kanamycin resistant cells. The mutant plasmid was named pOKcop. pOKcop is unusual in that the unit copy plasmid was converted to a multiple "runaway" copy number plasmid whose copy number is 500–700. This mutation with such a drastic change of copy number suggests tight host control of the plasmid replication through the repA protein.

The mutant plasmids of the present invention, pOKcop and the mutant P1 discussed below, are useful by virtue of their ability to coexist, in a high copy number, in a host cell with other available vectors. This characteristic permits the use of these plasmids to produce high yields of proteins expressed by available vectors, particularly in yields higher than possible with current vector systems. The media sensitivity of these plasmids further permits control of copy numbers and, therefore, protein expression by alteration of the growth media.

1.1 Materials and Methods

Bacterial strains and plasmids. The *E. coli* K-12 strain 20SO (F-, thi-1, ara-13, lacZ43, mgl-50, galP63, malA1, xyl-7, mtl-2, rpsL135γ-s, supE44) was used as a host cell for plasmids.

Media and culture conditions. Tryptic soy broth (from Difco Laboratories) was used for cultivation of bacteria to obtain plasmid DNA. Tryptic soy broth is a soybean-casein digest medium containing (per liter) 17 g of Bactotryptone (pancreatic digest of casein), 3 g of Bactosoytona (papain digest of soybean meal), 2.5 g of dextrose, 5 g of sodium chloride and 2.5 g of dipotassium phosphate. Yeast extract and tryptone from Difco Laboratories were used to grow bacteria from which the single stranded DNA of the plasmid was extracted for DNA sequencing. For the plasmid stability test, M9 minimal medium (5.95 g of $Na_2HPO_4$, 3.0 g of $KH_2PO_4$, 0.5 g of NaCl, 1.8 g of $NH_4Cl$, 0.26 g of $MgSO_4 \cdot 7H_2O$, 4.0 g of glucose, 5 mg of thiamine HCl each per liter) was used. Tryptic soy agar (Difco Laboratories) was used for transformation and viable cell counts. Where indicated, kanamycin sulfate was added to 50 μg/ml (Sigma Chemical Co.).

Plasmid construction. A small Rts1 derivative (pOK) consisting of the replication unit of Rts1 and kanamycin resistant gene (pOK) was constructed as follows. The kanamycin resistance gene located in the E fragment of Rts1 BamHI digest was excised by HincII digestion as a 1.5 kb fragment (25). The 1.9 kb replication region of Rts1 located in the D fragment of Rts1 BamHI digest (17) was excised with EcoRI and HindIII. This fragment corresponds to the 1.9 kb region excised with the same restriction enzymes from the mutagenized derivative of Rts1 (19). Both fragment ends were blunted and ligated with BamHI linkers (Boehringer Mannheim Biochemicals). BamHI-ended fragments were ligated and the resulting plasmid was introduced into *E. coli* 20SO host cells by transformation (27). The structures of pOK and pOKcop are illustrated in FIG. 1.

Nucleotide sequence determination. The DNA sequences were determined by the dideoxy chain termination method with [α-$^{35}$S] dATP (1000 Ci/mmol, from Amersham) using single stranded DNA or double stranded DNA as templates according to the manual of the sequencing kit (United States Biochemical Corporation).

Plasmid stability test. An overnight M9 culture medium of 20SO cells carrying pOK or pOKcop grown in the presence of kanamycin was diluted with fresh M9 medium containing the kanamycin and incubated at 32° C. for 3 hr. The exponential-phase culture was diluted with fresh M9 medium without kanamycin, to 0.01 optical density unit at 540 nm, and incubated at 32° or 42.5° C. At appropriate intervals, the culture was diluted and plated onto kanamycin-free agar plates to count the total viable cell number. About 50–100 colonies were picked and plated on kanamycin containing plates to determine the number of kanamycin resistant colonies.

Determination of copy number. *E. coli* K-12 strain 20SO harboring pOK or pOKcop was grown overnight at 32° C. in M9 or TBS (tryptic soy broth) culture medium containing kanamycin. An overnight M9 culture was diluted with fresh M9 medium containing kanamycin and incubated at 32° C. for 3.7 hr. The plasmid DNA was prepared from this exponential phase M9 culture or overnight TSB culture medium. A small known amount of 20SO (pUC19) culture was added to the above culture as an internal standard. The plasmid DNA prepared from the same number of plasmid-containing cells using a commercial kit (Qiagen Inc.) was subjected to digestion with EcoRI to obtain a linear DNA followed by a 0.7% agarose gel electrophoresis.

1.2 Results and Discussion

Figures 2A, 2B:
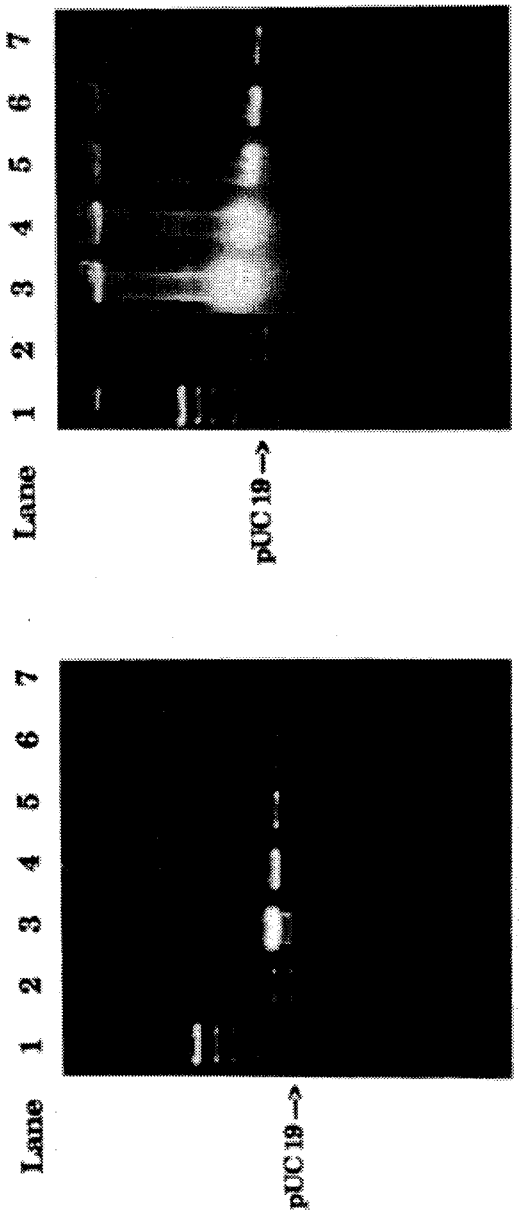
FIG. 2(a and b) shows the results of an estimation of the copy number of pOKcop in E. coli 20S0 cells.

The parent plasmid pOK, a small derivative of naturally occurring plasmid Rts1, like its ancestral plasmid Rts1, replicates as a unit plasmid and exhibits temperature sensitive instability (1–2 copies/cell) in the *E. coli* K-12 strain 20SO. The isolated mutant pOKcop has a very high copy number. The results of the copy number tests are shown in FIG. 2 wherein the exogenously added known amount of pUC19 was used as an internal standard (indicated by the arrow). Lanes: 1, 100ng of γ HindIII as a molecular size marker; 2, pOK; 3–7, pOKcop. Lanes 2 and 3, plasmid DNA isolated from 4×10$^{10}$ (a) or 2×10$^9$ (b) of cells; lanes 4–7, correspond to decreasing amounts of extracted pOKcop DNA as follows: lane 4, ⅓; lane 5, ⅒; lane 6, 1/30; lane 7, 1/100 of lane 3. As shown in FIG. 2 (lanes 3 through 7), the copy number of this mutant was 20 to 120 times (depending on culture conditions) higher than that of pOK. This result indicates that a stringent type of plasmid (pOK) was converted to a relaxed type of plasmid (pOKcop). The copy number of pOKcop per plasmid-containing cell did not significantly change with temperature shift from 32° C. to 42.5° C.

The results of the stability test are shown in FIG. 3, wherein *E. coli* strain 20SO harboring plasmids were examined for the kanamycin resistant cells during the growth in drug-free M9 minimal medium at 32° C. (open symbols) and 42.5° C. (closed symbols). ○, ●:pOK □, ■:pOKcop. Plasmid pOK, like its parent plasmid Rts1 (43), is unstable at 42.5° C. On the other hand, as one would expect from the large number of the plasmid in the cell, the loss of pOKcop at 42.5° C. was very slow as shown in FIG. 3. It is noted in this figure that the rate of loss of pOKcop is faster than one would predict on the basis that 20 copies of plasmids randomly assort during each cell division. This suggests that cells with less pOKcop may have a growth advantage.

The full nucleotide sequence of pOK is shown in FIG. 4 and the sequence of the repA protein portion of pOK is shown in FIG. 5. For the mutant pOKcop, the full nucleotide sequence and repA coding portions are shown in FIGS. 6 and 7, respectively.

Nucleotide sequencing of the replication region of pOK and pOKcop (nucleotides 70 through 1859) revealed that only a one-base substitution occurred at position 1199 in the repA region as compared with pOK. This region of the nucleotide sequence corresponding to repA of pOK is identical (except for the one-base mutation) to what has been reported (45) with mutagenized derivative of Rts1. This mutation changes the 159th amino acid of repA protein from histidine (CAT) to asparagine (AAT).

Figure 8B:
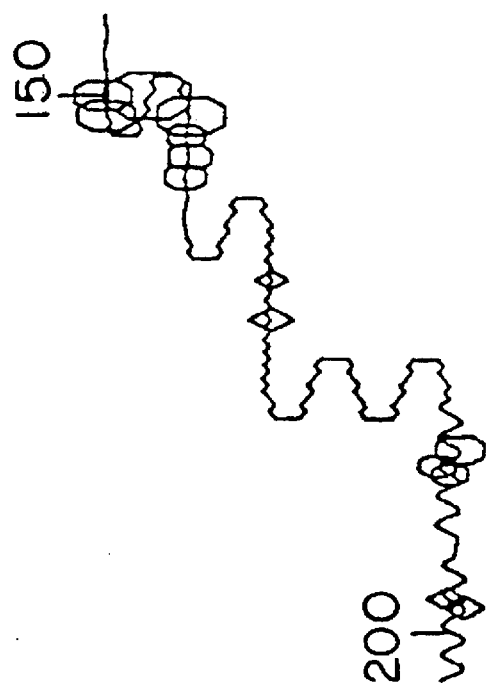
FIG. 8(a and b) shows the secondary structures of repA protein of pOK (a) and pOKcop (b) as created by the Cho-Fasman secondary structure program.
Figure 8A:
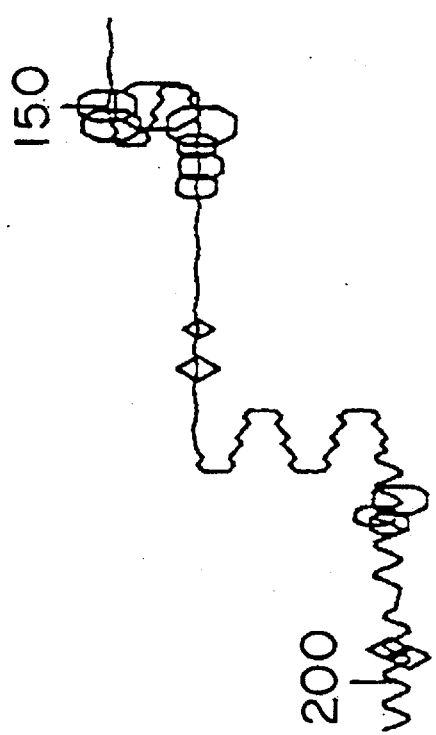

To confirm the inclusion of this mutation in the structure of repA protein, Cho & Fasman analysis (30) was performed. As shown in FIG. 8, this single substitution caused an apparent conformational change of repA protein around this mutation site. A computer search failed to detect a motif such as a zinc finger or helix turn helix, which are often observed with protein having affinity to nucleic acid.

Mutations in the repA protein of plasmids have been reported to increase the copy number moderately. Thus, various mutations of repA protein of Rts1 have resulted in increases of at most 3–5 fold in the copy number of Rts1 derivative. Other similar cases include mutations of replication proteins of P1, pSC101, R6K, and RK2. None of the mutations so far reported change the copy number of the plasmid as dramatically as the mutation described herein. This is considered important because it contributes to a better understanding of the replication control of unit copy plasmids such as Rts1, P1 and F plasmids.

Various mechanisms of replication regulation of plasmids have been described, mostly focusing on the mechanism of self regulation. The essence of this hypothesis is that an indispensable initiator protein, repA for each plasmid, has dual functions, positive as well as negative activity regarding the control of copy number. In all cases, repA protein is known to bind to its own promoter and function as a repressor of its own transcription. In addition, with P1 or Rts1, the binding of repA proteins at the dispensable incI or incA reduces the copy number of the plasmid. The dual functions of the initiator protein E for F plasmid has been shown to be sufficient to keep unit copy number throughout the cell cycle by the simulated model calculation. On the basis of this hypothesis, one can explain the present observation by simply assuming that the single amino acid change in Rts1 repA greatly reduces affinity of this protein as a repressor or negative controller.

The behavior of the mutant pOKcop may alternatively be explained on the basis of a hypothesis that regulation of the unit plasmid is strictly under the host control through the interaction of repA with the host chromosome replication machinery. There are few reasons for this hypothesis. First of all, the widely accepted auto regulation model has an inherently paradoxical element. In order to overcome this paradox, a number of assumptions have to be made. Although computer simulation based on the auto regulation gave results consistent with the actual case, it had to make an assumption that host components necessary for the plasmid replication are always abundant, and sufficient throughout the cell cycle. Secondly, experimentally, abundant supply of repA protein by a compatible plasmid does not eliminate the plasmid immediately as one expects from the vigorous control for unit copy plasmid. Thirdly, recent evidence suggests that replication of F plasmid is cell cycle dependent. It is then relatively easy to imagine that the replication of unit copy plasmid is tightly coupled to replication of host chromosome through the interaction of repA with the host chromosome replication machinery. In fact, repA has to be activated to bind to the plasmid DNA through a series of interactions with host DNA synthesis components. It is interesting to note that consideration of a model for *E. coli* chromosome segregation suggests that the initiation of chromosomal replication is regulated by concentration of factors such as DnaA protein. Possible host control of plasmid replication through other host factors has also been suggested (41). The well documented auto regulation system probably operates for fine tuning of replication which plays an important role for incompatibility of the plasmid.

On the basis of the strict host control hypothesis, we propose that repA of pOKcop must have lost the need of host chromosome replication machinery for its activation. It may be constantly activated and hence the dramatic increase of copy number was observed. With the mutated repA, the plasmid may completely escape the rigid host control of its replication.

2. The P1 Mutant

The bacterial plasmid, P1 prophage, is known to be stably inherited but at a low copy number. The sequence of P1 has been elucidated and shown to include various functions, including an origin of replication (oriR), its associated specific initiator (repA) and control element (inc.A), and other regions.

Figure 9A:
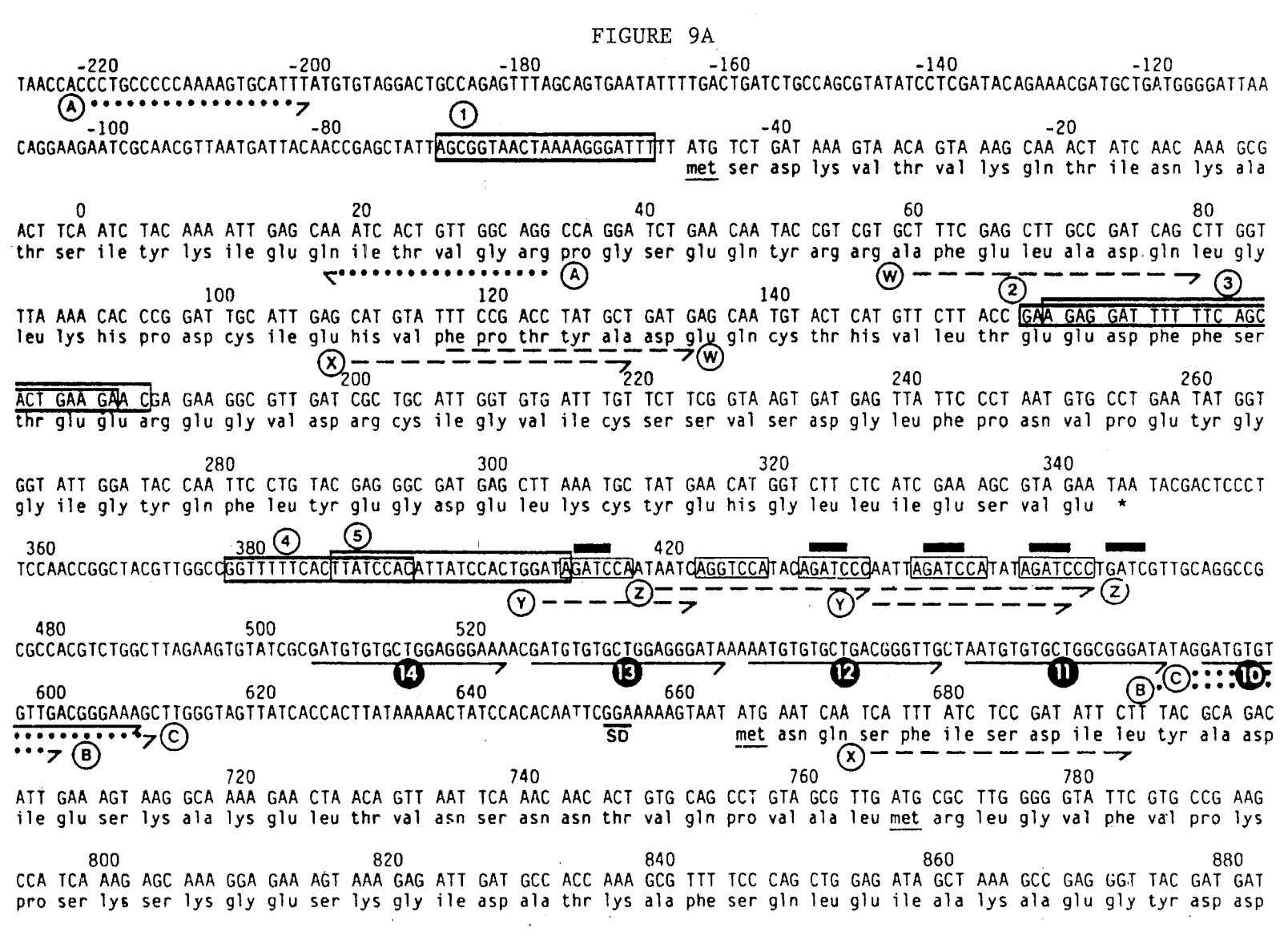
Figure 9C:
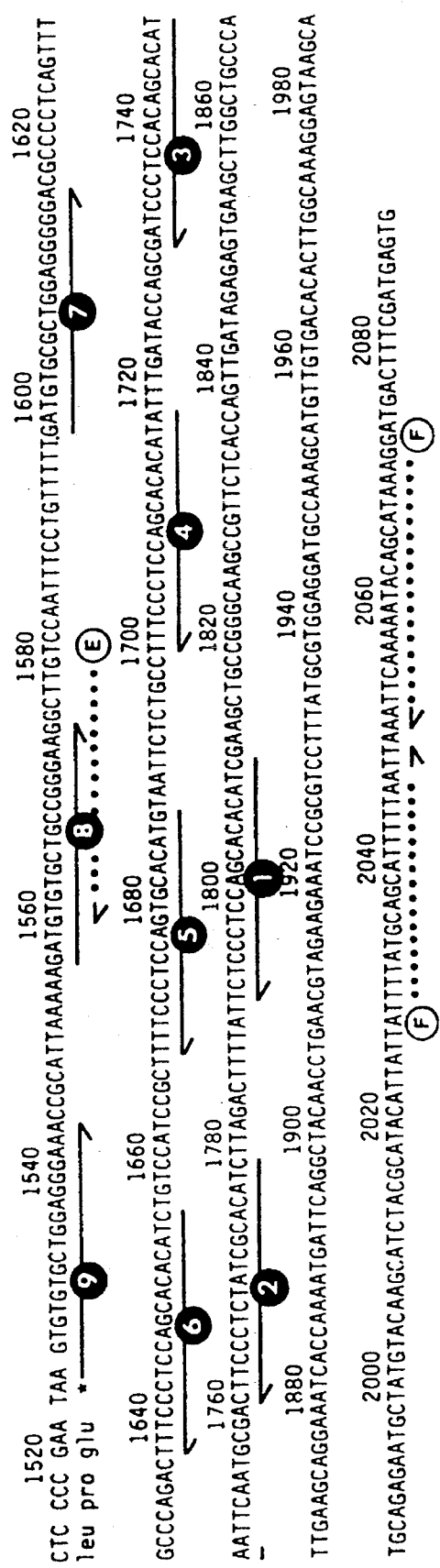
FIG. 9 shows the sequence of the replication region of the plasmid P1 (SEQ. ID NO. 7).

The full nucleotide sequence of the P1 plasmid replication region is shown in FIG. 9. The sequence shown is from the cleavage point of the leftmost HincII site to the 5'G of a HinII site 150 bp to the left of the XhoI site. The 5'G of the unique EcoRI site arbitrarily defines position 1000. Heavy arrows, numbered 1 through 14, underline and indicate the orientation of the 19 bp repeat sequences found in the incC and incA determinants. Other direct repeats are indicated by the broken arrows (w to z). Dotted arrows (A to F) indicate inverted repeats. Direct and inverted repeats shown are those with at least 15 matched bases and a probability of occurrence in a random sequence of less than $10^{-5}$. The Shine & Dalgarno sequence preceding the repA open reading frame is marked SD. The amino acid sequence for the repA open reading frame and for the open reading frame of the preceding incC are shown below the DNA sequence. Small outlined boxes enclose 5 direct 7 bp repeat sequences in a 55 bp region, which also includes 5 G-A-T-C sequences (overlined). Heavily outlined boxes, numbered 1 to 5 enclose sequences homologous to those found in the replication region of mini-F. From this Figure, it can be seen that the repA protein coding region begins at position 664 and terminates at position 1521.

Figure 10A:
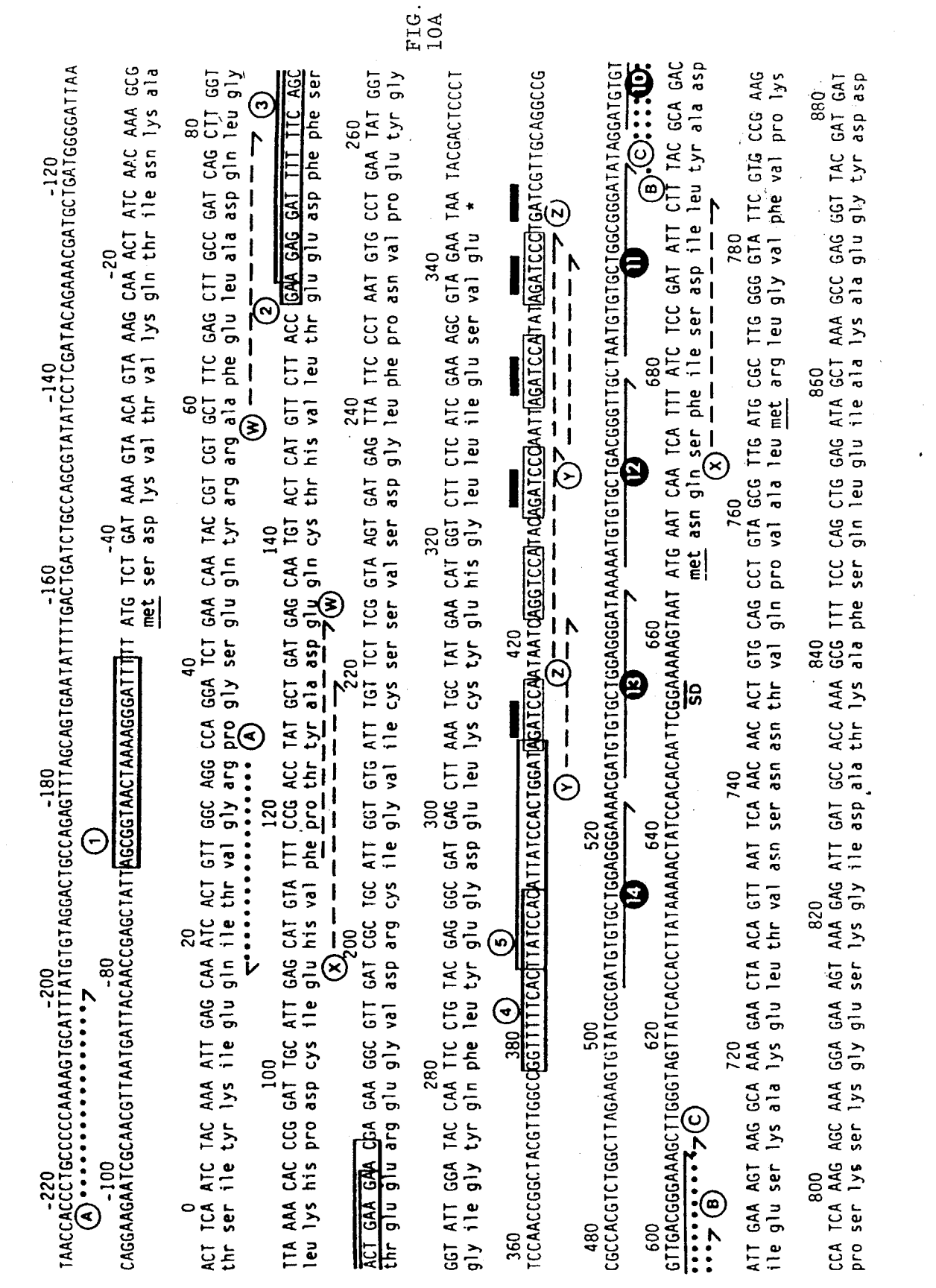

The mutant P1 of the present invention is mutated similar to the mutation for pOKcop, in that, whereas repA of P1 contains glutamine at aa 158, the mutant P1 contains asparginine at that position. FIG. 10 shows the nucleotide sequence of the mutant P1 plasmid replication region.

3. Temperature Stabilization of pOK, pOKcop and the P1 Mutants by $GH_3$ (15906P) DNA.

As discussed above, the plasmid pOK consisting of the replication region and the kanamycin resistance gene fragment of Rts1 was unstable but replicated at the nonpermissive temperature of 42.5° C. The replication region was sequenced and the repA protein sequence was found to be different from that of the mutagenized temperature sensitive Rts1 derivative 19. The instability of pOK at 42.5° C. was due to temperature sensitive partition of the plasmid during cell division. Presence of a short inverted repeat in the presumed par region of this replicon had consecutive A sequences suggesting that this may be responsible for the temperature sensitive partition. This plasmid is stabilized at 42.5° C. by another Rts1 fragment, named $GH_3$, comprised of a 1590 bp fragment derived by HindIII digestion of the 10.5 kb BamHI fragment of the original Rts1 DNA. This stabilizing fragment contains several inverted and direct repeats. It functioned only in the cis configuration with Rts1 replication origin suggesting that the stabilization unit does not function through cytoplasmic soluble agents such as RNA or protein. Presence of this stabilizing fragment in other compatible plasmids made the stable derivative of pOK containing this fragment unstable suggesting that this fragment has an affinity to the cellular components which play important role for plasmid partition. The stabilizing fragment did not influence the copy number of pOK. A smaller fragment derived from $GH_3$ was totally or partially active. All the active fragments contained at least one inverted repeat. None of these inverted repeats contained a consecutive A sequence as found in the par region of the wild type pOK.

As detailed above, Rts1 is a high-molecular weight drug resistance factor (9) which confers kanamycin resistance ($Km^r$) (36). It belongs to the T-incompatibility group (5), and expresses various temperature-sensitive phenotypes. The temperature-sensitive phenotypes include T4 bacteriophage restriction (13), influence on host cell growth (7, 25, 27, 33), instability of plasmid (14, 28, 32, 36), and formation of covalently closed circular plasmid DNA (42). Recently, partial nucleotide sequences of Rts1 have been reported (12, 25, 32). In addition, a smaller derivative of Rts1, pTW20 was obtained by mutagenesis of Rts1 DNA and the regions involved in DNA replication (14, 19), and incompatibility (20) of this plasmid have been sequenced.

Partitioning of plasmids in bacteria during cell division is different from that of eukaryotic cellular DNA in that bacteria do not have kinetocores, centromeres or spindles. Yet, in normal situations, plasmids are properly partitioned during the bacterial cell division so that every daughter cell contains plasmids. As a consequence of sufficient replication and proper partition, the maintenance of plasmids in each bacterium can be accomplished. The mechanism of this proper partition has been studied and various mechanisms have been proposed (40). The present inventor has examined the temperature sensitive instability of pOK, a small derivative of Rts1 with the original Rts1 replication unit. The results suggest that, in confirmation of previous results with Rts1 replication (7), the replicon of Rts1 functions even at the nonpermissive temperature but the partition of the replicated plasmid is not normal at 42.5° C. The replication region of the Rts1 replicon was sequenced and variance from the reported sequence from mutagenized derivative of Rts1, pTW20 was noted in the repA and incI regions (19). This explains the discrepancy with respect to temperature sensitive replication of the Rts1 derivative and Rts1 itself. In addition, a 1590 bp DNA fragment from Rts1 was isolated and this fragment restored the partition of pOK at 42.5° C. The possible role of inverted repeat sequences in the temperature sensitive partition and the mechanism of the action of stabilizing elements was investigated by the present inventor.

3.1 Materials and Methods

Bacterial strains and plasmids. The *E. coli* K-12 strain 20SO (F, thi-1, ara-13, lacZ43, mgl-50, galP63, malA1, xyl-7, mtl-2, rpsL1351-s, supE44?) (10) was used as a host cell for plasmids. Plasmids used in this study are listed in Table 1. Plasmid pMW119 was purchased from Nippon Gene (Tokyo, Japan).

Media and culture conditions. Tryptic soy broth (from Difco Laboratories) was used for cultivation of bacteria to obtain plasmid DNA. Yeast extract and tryptone from Difco Laboratories were also used to grow bacteria. For the plasmid stability test, M9 minimal medium (5.95 g of $Na_2HPO_4$, 3.0 g of $KH_2PO_4$, 0.5 g of NaCl, 1.8 g of $NH_4Cl$, 0.26 g of $MgSO_4.7H_2O$, 4.0 g of glucose, 5 mg of thiamine HCl, each per liter) was used. Tryptic soy agar (Difco Laboratories) was used for detecting transformed cells and counting viable cells. Where indicated, antibiotics were added to 50 mg/ml (kanamycin sulfate) or 100 mg/ml (ampicillin sodium slat, from Sigma Chemical Co.).

DNA technology. DNA isolation, cloning, and agarose gel electrophoresis were performed essentially as described by Maniatis et al. (44). Plasmid DNA was prepared essentially with the method of Birnboim and Doly (3) or a commercial kit (Qiagen Inc.). Restriction endonucleases, T4 DNA ligase, Klenow fragment of *E. coli* DNA polymerase I, and T4 DNA polymerase were obtained from Boehringer Mannheim Biochemicals. Conditions for restriction enzyme reactions were specified by the suppliers.

TABLE 1

Plasmids used.

| Plasmid | Characteristics | Source or reference |
| --- | --- | --- |
| Rts1 | Naturally occurring plasmid carrying $Km^r$ | (36, 42) |
| pFY556 | Mini-Rts1 plasmid containing D, E, G framents[1)] of Rts1 | (17) |
| pFY603 | Mini-Rts1 plasmid containing D, E fragments of Rts1 | (41) |
| pOK | The replication region and $Km^r$ HincII fragment of Rts1 | present application |
| pOK-G | pOK and G frament of Rts1 | present application |
| pOK-1G3 | pOK and the third largest fragment of HindIII digests of G fragment ($GH_3$ fragment) at BamHI site downstream of repA gene of pOK | present application |
| pOK-2G3 | pOK and $GH_3$ fragment at BamHI site downstream of $Km^r$ gene of pOK | present application |
| pOK-3G3 | The same as pOK-1G3 but with the opposite direction of $GH_3$ | present application |
| pMW119[b)] | Reconstructed plasmid carrying $Ap^4$, compatible with Rts1 | present application |
| pMW119-1G3 | $GH_3$ fragment and pMW119 at the HindIII site | present application |
| pMW119-2G3 | The same as pMW119-1G3 but at opposite direction of $GH_3$ | present application |
| pOK-G11 | $GH_3$ D(470–565) fragment and pOK at the BamHI site | present |
| pOK-G12 | The HindIII-MaeII 470-bp (1–470) fragment of GH3 and pOK at the BamHI site | present application |
| pOK-G13 | The MaeII-HindIII 1026-bp (565–1590) fragment of GH3 and pOK at the BamHI site | present application |
| pOK-G14 | The BstEII-DraIII 525-bp (319–843) fragment of GH3 and pOK at the BamHI site | present application |
| pOK-G15 | The MaeII-ClaI 439-bo (565–1003) fragment of GH3 and pOK at the BamHI site | present application |
| pOK-G16 | The ClaI-HindIII 588-bp (1003–1590) fragment of GH3 and pOK at the BamHI site | present application |

TABLE 1-continued

Plasmids used.

| Plasmid | Characteristics | Source or reference |
|---|---|---|
| pOK (ΔE+H) | Derivative of pOK which lacks EcoRI-HincII fragment | present application |
| pOK (ΔB+D) | Derivative of pOK which lacks BpmI-DraI fragment | present application |

[a)]D, the fourth largest fragment (27 kb) of the BamHI digests of Rts1 plasmid containing replication region of Rts1.
E, the fifth largest fragment (21.5 kb) of the BamHI digests of Rts1 plasmid containing Km$^r$ gene.
G, the seventh largest fragment (10.5 kb) of the BamHI digests of Rts1 plasmid containing the plasmid stabilizer.
[b)]It consists of replicon of pSC101 (2), multicloning site of pUC19, and Ap$^r$ of pBR322.

Plasmid construction. The compositions of plasmids used in this study are listed in Table 1. Plasmids pFY556 and pFY603 were obtained from Rts1 by relegation of BamHI digests (named A through P in order of molecular weights) of Rts1 DNA as described (17, 41). A small Rts1 consisting of the replication unit of Rts1 and kanamycin resistant gene (pOK) was constructed as follows. The kanamycin resistance gene located in the E fragment of Rts1 BamHI digest was excised by HincII digestion as 1.49 kb fragment (25). The replication region of Rts1 located in the D fragment of Rts1 BamHI digest (41) was excised with EcoRI and HindIII double digestion as a 1.85 kb fragment (14). Both fragment ends were blunted and ligated with BamHI linkers (Boehringer Mannheim Biochemicals). BamHI-ended fragments were ligated. The resulting plasmid was introduced into E. coli 20SO host cells by transformation (11).

Figure 18:
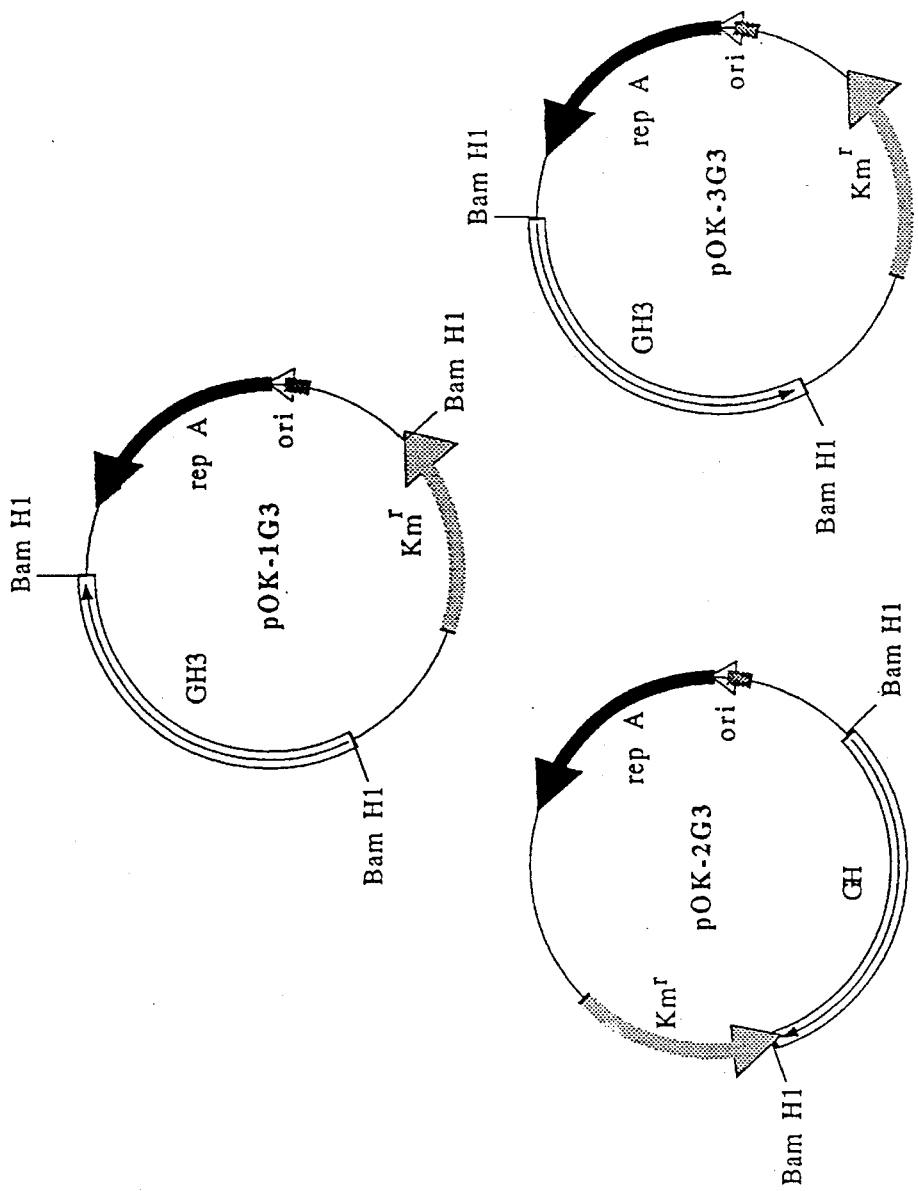
FIG. 18 shows the configuration of pOK derivatives containing $GH_3$ fragment.

The various stabilizing fragments were obtained from the G fragment of Rts1 DNA. The G fragment (10.5 kb), a BamHI digest of Rts1 DNA (17, 41), was obtained by digestion of pFY556 (consisting of fragments D, E, and G, (17)) with BamHI. The G fragment was digested with HindIII and the third largest fragment (1.6 kb) was designated as GH$_3$. The GH$_3$ fragment with BamHI linkers was inserted into one of the BamHI sites of pOK in both directions and they were designated as pOK-1G3, pOK-2G3, and pOK-3G3 as shown in FIG. 18. In that FIG., the arrows indicate the reading direction of genes. The arrow in GH$_3$ is the same direction as indicated in FIG. 15 (5'→3'). All the fragments were derived from original Rts1 and connected with linkers.

To construct plasmids containing stabilizing fragments, GH$_3$ or fragments thereof, each fragment was converted a to BamHI-end fragment and inserted into one or the other BamHI site of pOK. Derivatives of pOK containing smaller fragments of GH$_3$, as listed in FIG. 18, were constructed by random ligation with BamHI-ended fragments. For the preparation of pOK(ΔE+H) and pOK(ΔB+D), pOK was digested with EcoRI plus HincII or BpmI plus DraI, and relegated after blunt end construction with the Klenow fragment or T4 DNA polymerase. To prepare pMW119-1G3 and pMW119-2G3, the GH$_3$ fragment was inserted into the pMW119 at the HindIII site in both directions. pMW119-1G3 and pMW119-2G3 were introduced into 20SO harboring pOK or pOK-1G3, and selected for growth in the presence of both ampicillin and kanamycin to obtain stable double transformants.

Nucleotide sequence determination. The DNA sequences were determined by the dideoxy chain termination method (30) with [a-$^{35}$S]dATP (1000Ci/mmol, from Amersham) using single stranded DNA or double stranded DNA as templates according to the manual of the sequencing kit (United States Biochemical Corporation). For determination of the DNA sequence of the replication unit of intact Rts1 plasmid, the polymerase chain reaction was performed using cells harboring Rts1 according to the method described by Joshi et al. (16).

Plasmid stability test. An overnight M9 culture medium of 20SO cells carrying a plasmid grown in the presence of appropriate antibiotics was diluted with fresh M9 medium containing the antibiotics and incubated at 32° C. for 3 h. The exponential-phase culture was diluted with fresh M9 medium without the antibiotics, to 0.01 optical density unit at 540 nm, and incubated at 32 or 42.5° C. At appropriate intervals, the culture was diluted and plated onto antibiotic-free agar plates to count the total viable cell number. After colonies appeared (overnight incubation) at least 100 colonies were picked with sterile toothpick and inoculated onto a plate containing TSB and appropriate antibiotics (50 mg/ml of kanamycin or 100 mg/ml of ampicillin). The stability was measured by counting the number of drug resistant colonies. It should be noted that the plasmid stability test described in this section measured the stability of plasmid in the liquid culture. Our data suggests that the stability may be different with the solid agar culture. This was supported by the observation that pOK containing cells at time zero of the test may be often not 100% but 80 to 90%.

Determination of plasmid copy number. E. coli strain 20SO harboring pOK or pOK-1G3 was grown overnight at 32° C. in M9 medium containing kanamycin. An overnight M9 culture was diluted with fresh M9 medium containing kanamycin, to 0.2 optical density unit at 540 nm, and incubated at 32° C. for 3.7 h. The plasmid DNA was prepared from this exponential phase M9 culture medium. A small known amount of 20SO(pUC19) culture was added to the above culture as an internal standard for plasmid recovery. The plasmid DNA prepared from the same number of plasmid-containing cells was subjected to digestion with EcoRI to obtain a linear DNA followed by 0.7% agarose gel, electrophoresis. The gel stained with ethidium bromide, was illuminated with UV transillumination and photographed through a filter. The film was scanned and the amount of plasmid DNA was estimated.

3.2 Results

Figure 11B:
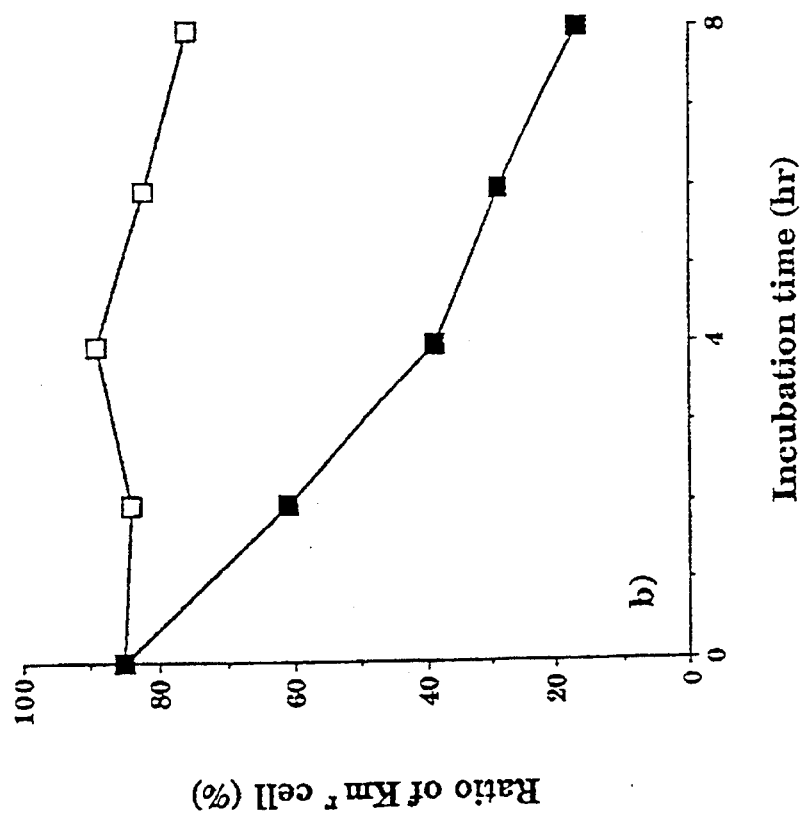
FIG. 11(a) and (b) show the results of studies on the replication of plasmid pOK at 42.5° C. —temperature sensitive instability.
Figure 11A:
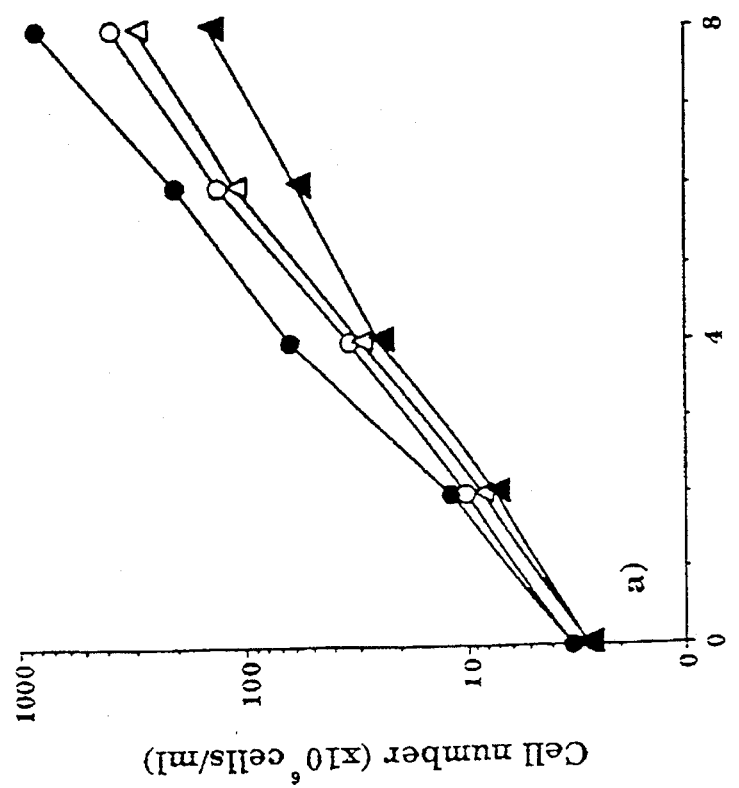

Characteristics of the replication unit of Rts1 (pOK). The replication region of Rts1 was combined with the kanamycin resistant gene of Rts1, and the resulting plasmid was designated as pOK. The growth of 20SO cells harboring pOK was investigated at 32 and 42.5° C. FIG. 11 shows the results of the replication studies of pOK for temperature sensitive instability wherein E. coli strain 20SO harboring pOK was grown in drug-free M9 minimal medium at 32° C. (circle) and 42° C. (triangle). A) Samples were analyzed for the total number of viable cells (open symbols) and plasmid-containing cells (closed symbols). B) The time course of the ratio of plasmid containing cells to the total viable cells at 32° C. (open circle) and 42.5° C. (closed circle). As shown in FIG. 11a, the viable cell number increased at both temperatures. It is important to point out that the cell number of E. coli harboring pOK (kanamycin resistant cells) increased almost with the same rate both at 32 and 42.5° C. up to 4 h, indicating that the replication of plasmid was not blocked at this temperature. On the other hand, FIG. 11b shows that the fraction of plasmid-containing cells in the whole population decreased from the beginning of the temperature shift to 42.5° C. without lag time.

Nucleotide sequence of the replication region of Rts1. The replication of a plasmid pTW601, containing the replication region of pTW20 which was derived from a mutagen treated Rts1, has been reported to be temperature sensitive (14). As described in the preceding section, the replication of pOK at 42.5° C. was not very much different from that at 32° C. The replication region of pTW601 (derived from pTW20) has been sequenced (19). To understand the discrepancy between pTW601 and pOK, the nucleotide sequence of the replication region of pOK was determined for comparison. FIG. 12 shows the complete nucleotide sequence of the replication region of pOK (EcoRI/HindIII fragment). The sequences are arranged so that the nucleotide number 1 is the recognition sequence for HindIII. The strand shown is in the 5' to 3' direction. The open reading frame for the repA protein is underlined. The sequence is compared with the reported corresponding sequence of mutagenized Rts1 derivative (19); bases and an amino acid in the parenthesis indicate the reported nucleotide base and amino acid and a line in the parenthesis represents the deletion in the replicon of mutagenized Rts1. Sequences of interest such as GATC repeats, DnaA box, and the promoter sequence of repA are boxed. The wavy line represents the sequence found in the par region of pSC101. [] indicates the region where the par resides. The vertical arrow draws the base which different from that of mutagenized Rts1 replication in which results in a different amino acid within the repA region. The half arrows with broken line mark inverted repeats. The direct repeats are indicated by lines above the sequence. Comparison of this sequence with that of pTW601 revealed that there are several different nucleotides (marked with stars) at the incI region downstream from the repA coding region. In addition, there are three nucleotides in this region missing in the pTW601 but present in Rts1 [indicated as (–)]. However, the most important difference is the one-base alteration at the repA region (at nucleotide 1502), which resulted in the replacement of asparagine (AAT) (at amino acid 260) with tyrosine (TAT). It should be noted that perfect 20 bp inverted repeat (nucleotides from 353 to 403), several direct repeats, and small 8 bp inverted repeat (nucleotides from 665 to 688) are observed at both sides of the repA coding region as previously reported (19). To ascertain that the sequenced replication region of pOK is identical to that of the original Rts1 replication region, we determined the nucleotide sequence of the corresponding region of Rts1 using the polymerase chain reaction (16). The nucleotide sequence was completely identical with the replication region of pOK as shown in FIG. 12.

Figure 13:
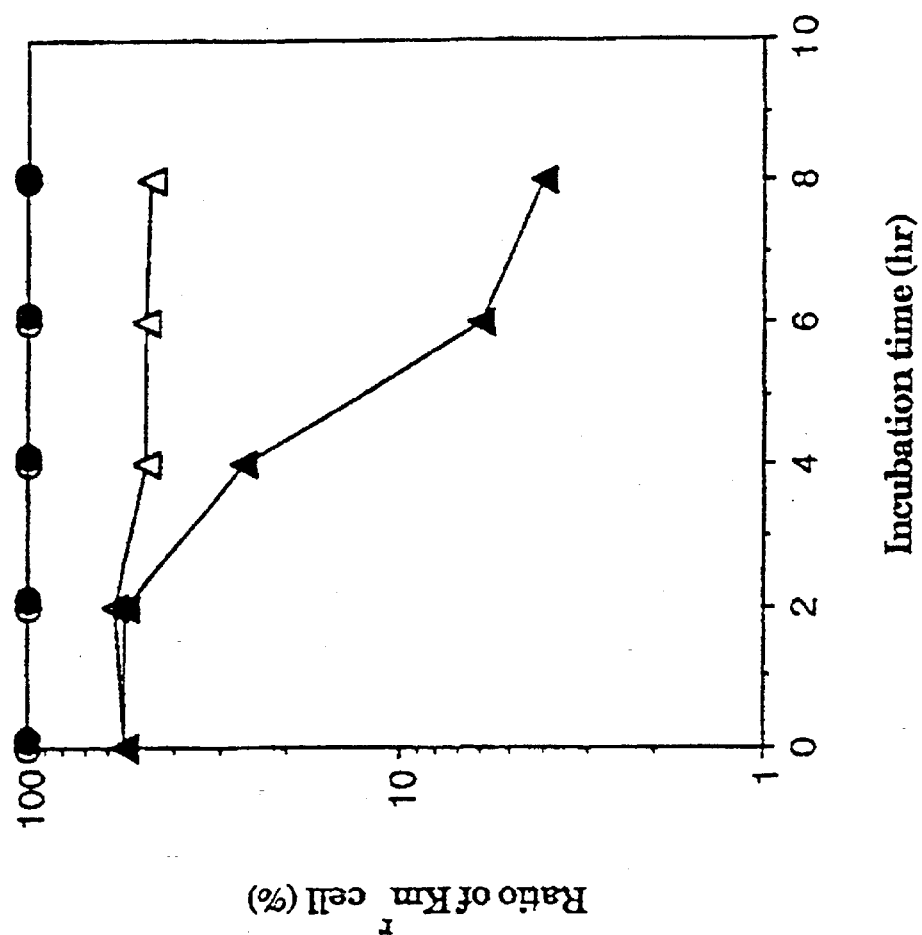
FIG. 13 shows the results of studies on the stability of deletion derivatives of pOK.

Deletion derivatives of pOK. In an attempt to localize the par region in the above sequence of the replication unit of pOK, deletion derivatives of pOK (pOK (DE+H) lacking nucleotides from 1640 to 1854 and pOK (DB+D) lacking nucleotides from 240 to 448) were constructed. FIG. 13 shows the results of the stability studies of pOK deletion derivatives, in particular E. coli strain 20SO harboring pOK(○,●pOK(ΔE+H); Δ,▲pOK(ΔB+D). As shown in FIG. 13 the deletion of approximately 200 bp upstream of the incII region did not change the stability of pOK. This plasmid was still stable at 32° C. and rapidly lost at 42.5° C. On the other hand pOK (DE+H) was very stable and did not lose the plasmid at all at both temperatures. The copy number of this plasmid was increased 4–5 fold, in confirmation of the previous report (20). From this experiment we concluded that without this region the partitioning can take place normally. The apparent loss of temperature sensitivity of this plasmid is understandable because the copy number increased 4–5 fold. The expected loss of plasmid after 8 h incubation calculated on the assumption that 10 copies of plasmid per cell are randomly lost, was only 2%. It should be noted that replication of this plasmid goes on at 42.5° C. perfectly well further confirming our notion that the replicon of this plasmid is not temperature sensitive. These experiments established that the par region must be within nucleotides from 450 to 1650, or in the Kanamycin fragment (HincII-L, 25).

A HindIII fragment derived from Rts1 stabilized pOK at 42.5° C. It has previously been shown that pFY603 consisting of D and E fragments of Rts1 DNA was unstable at 42.5° C. to some extent (42). On the other hand, another smaller derivative of Rts1 plasmid, pFY556 consisting of D, E, and G fragments was stable at 42.5° C. as shown in Table 2. This suggests that G fragment has stabilizing function on a plasmid derived from the Rts1 replicon. It was therefore of interest to examine if the G fragment (10.5 kb, seventh largest BamHI fragment of Rts1) has the stabilizing effect at 42.5° C. on pOK. As shown in Table 2, pOK-G containing the G fragment was completely stabilized by the G fragment. To find out which portion of the G fragment functions as a stabilizer, six Hind III fragments of G fragment with BamHI linker were separately inserted into pOK at the BamHI sites. It was then found that the third largest fragment (named GH$_3$) was the most effective stabilizer of pOK (data not shown).

Figure 14:
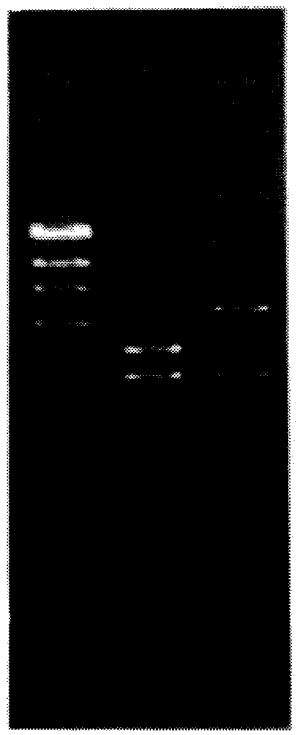
FIG. 14 shows results of studies on the estimation of relative copy number of Rts1 derivatives in E. coli 20SO cells. The plasmid DNA was prepared, digested with EcoRI and electrophoresed in a 0.7% agarose gel as described in Materials and Methods. pUC19 was used as an internal standard (indicated by the arrow). Lanes: 1, 100 ng of λDNA digested with HindIII as a molecular size marker; 2, pOK; 3, pOK-1G3.

FIG. 14 shows results of studies on the estimation of relative copy number of Rts1 derivatives in E. coli 20SO cells. The plasmid DNA was prepared, digested with EcoRI and electrophoresed in a 0.7% agarose gel as described in Materials and Methods. pUC19 was used as an internal standard (indicated by the arrow). Lanes: 1, 100 ng of λDNA digested with HindIII as a molecular size marker; 2, pOK; 3, pOK-1G3. As shown in Table 2 and FIG. 14, the GH$_3$ fragment, inserted at the BamHI site in either direction, stabilized pOK completely at 42.5° C. In addition, GH$_3$ inserted at another BamHI site exerted its effect indicating that the regardless of direction of GH$_3$ and the insertion site it can exert its stabilization effect.

As shown in Table 2, this fragment completely stabilized pOK without increasing its copy number. The copy number of pOK was estimated 1–2 copies/cell from this figure and that of pOK-1G3 was almost equal to this. This suggests that the 1.6 kb Hind III fragment aids partitioning of pOK at 42.5° C.

The nucleotide sequence of this stabilizing fragment was then determined. The entire 1590 bp sequence is shown in FIG. 15. The sequence is arranged so that the strand shown is in the 5' to 3' direction. The sense strands of 3 ORFs are underlined. The possible –35, –10, and Shine-Dalgarno sequences are boxed. The half arrows mark a perfect inverted repeat. The imperfect inverted repeats are indicated by broken lines. The direct repeats are indicated by lines above the sequence. Computer analysis of this sequence revealed three possible open reading frames (ORF-1, ORF-2, ORF-3) which have the Shine-Dalgarno sequences and encode peptides of reasonable length (more than 20 amino acids). However, a possible consensus promoter sequence was found only for ORF-2 at nucleotides 822 to 827 (TATACC) followed by a –35 sequence at nucleotides 800 to 805 (TATCAA). The most notable feature of the GH$_3$ fragment is several inverted repeats, though most of them are imperfect repeats. Similar inverted repeat structures have been reported in the partition sites of Esherishia coli plasmids (21, 22, 24) and Bacillus subtilis plasmid (4). In addition, several direct repeats (GTTTT) were observed in this fragment.

GH$_3$ fragment is active only in the cis configuration. The genetic elements which control plasmid partitioning, are either trans-acting which encode proteins (1, 26) or cis-acting small segments which do not encode any proteins (4, 22, 23, 26). To test whether the GH$_3$ fragment functions in trans, we constructed the doubly transformed strain 20SO(pOK, pMW119-G3). FIG. 16 shows the results of the GH$_3$ stabilizing studies. *E. coli* strain 20SO harboring pOK or pOK-1G3 plasmids and pMW119 derivatives were examined for the kanamycin resistant cells during the growth in drug-free M9 minimal medium at 32° C. (open symbol) and 42.5° C. (closed symbol) as described in Materials and Methods. a) Stability of pOK at 32° C. and 42.5° C. is not influenced by GH$_3$ in the compatible plasmids. ○●, 20SO(pOK, pMW119; △▲, 20SO (pOK, pMW119-1G3); □■, 20SO (pOK, pMW119-2G3). b) Stabilized pOK (pOK-1G3) becomes unstable at 42.5° C. by pMW119-1G3. △▲, 20SO(pOK-1G3, pMW119); △▲, 20SO(pOK-1G3, pMW119-1G3).

As shown in FIG. 16(a), simultaneous presence of pMW119 containing GH$_3$ fragment in either direction could not stabilize pOK in trans suggesting that GH$_3$ functions in cis configuration. If the GH$_3$ fragment functions as a stabilizer through a cis-acting partition segment, one would expect that the GH$_3$ segments in compatible plasmids which coexist within the same cell should compete with pOK-G3 for the cellular components involved in the even distribution of the plasmid. This could result in the loss of the plasmid with smaller copy number. FIG. 16(b) indicates that while pOK-1G3 was very stable in 20SO host cells when existed alone, it became rather unstable when it coexisted with GH$_3$ located in another compatible plasmid (pMW119). All viable cells in this study were resistant to ampicillin, indicating that pMW119 derivative plasmids were very stable. This suggests that GH$_3$ contains a par-like region which interacts with cellular components necessary for partition. This portion functions only in cis, and the presence of this region in the compatible plasmid gives incompatibility due to competitive binding to this component.

TABLE 2

Effect of G and GH3 fragment on plasmid stability

| Plasmid | Incubation conditions | % Loss of plasmid[a] |
|---|---|---|
| pOK | 42.5° C., 8 hr | 92% |
| pOK-1G3 | 42.5° C., 8 hr | 0% |
| pOK-2G3 | 42.5° C., 8 hr | 0% |
| pOK-3G3 | 42.5° C., 8 hr | 0% |
| pOK-G | 42.5° C., 8 hr | 0% |
| pFY556 | 42.5° C., 8 hr | 0% |

[a] The fraction of plasmid-containing cells among viable cells was determined as described in Materials and Methods after the incubation at the nonpermissive temperature. Values represent the mean of at least 2 determinations.

Figure 17:
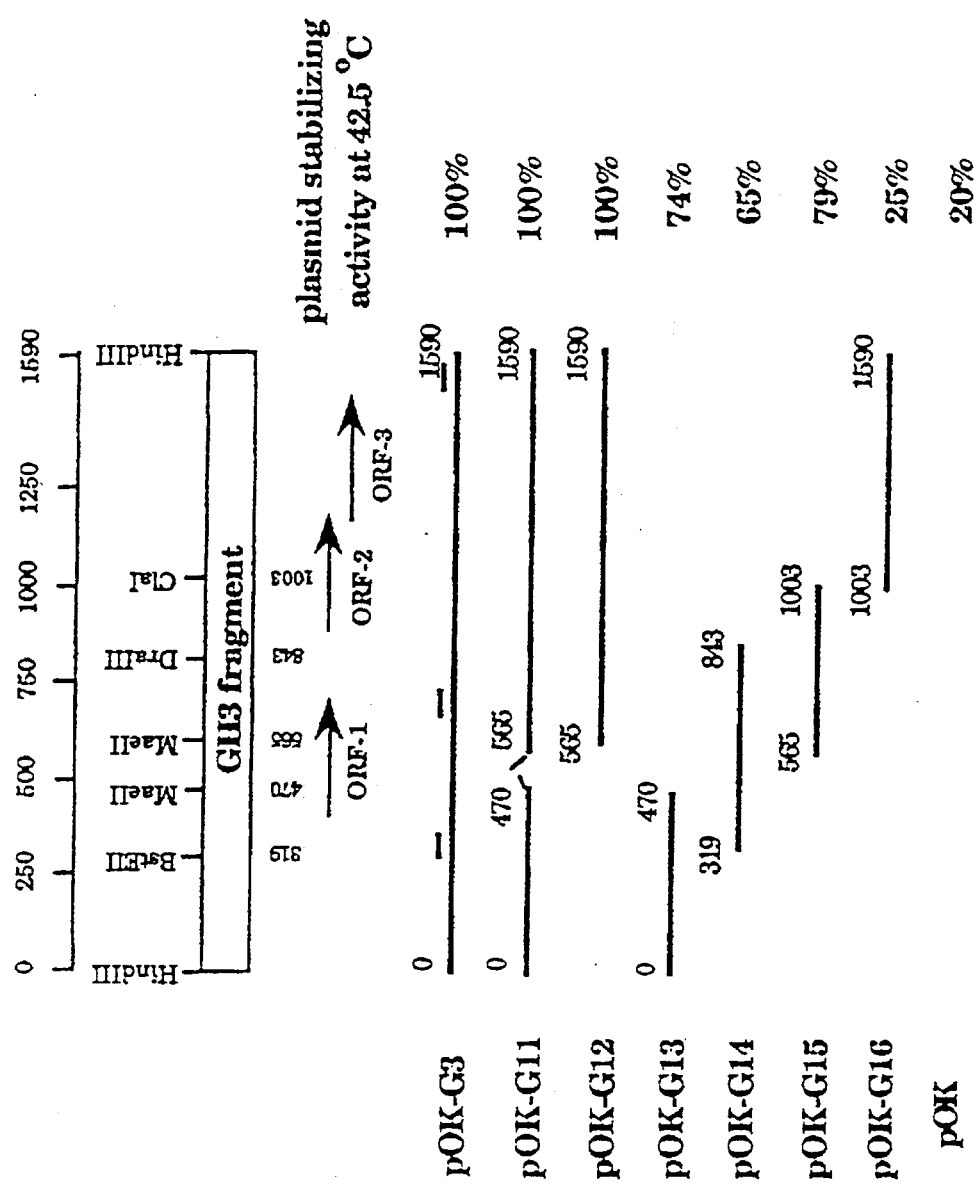
FIG. 17 shows results of studies on the stabilizing activities of plasmids containing various portions of the $GH_3$ fragment.

Attempt to identify the region responsible for the stabilizing function within the GH$_3$ fragment. As described above, the possible stabilizing gene in the GH$_3$ fragment seemed to be a cis-acting small segment rather than a trans-acting protein coding segment. However, GH$_3$ contains three ORFs. Further localization of the par activity within GH$_3$ would determine whether or not these ORFs are necessary for the par activity. For this purpose, various deletions were made in the GH$_3$ fragment and examined. The effect of these fragments is shown in FIG. 17. These fragments were inserted into pOK using BamHI linkers. The fraction of plasmid-containing cells was determined as described in Materials and Methods after the 8 h-incubation period at 42.5° C. Values represent means of 2 or more determinations. Plasmid pOK-G11 which has deletion in the midst of ORF-1, was stable, indicating that ORF-1 is not necessary for the GH$_3$ function. Plasmid pOK-G12 has only bases 1 to 470 and does not contain any ORF but this had as much as 74% stability compared with the complete GH$_3$ confirming the notion that no protein is involved in this stabilizing activity. On the other hand, plasmid pOK-G13 which covers entire ORF-2 and ORF-3 without the above 470 bp retained 100% stability. Plasmids pOK-G14 and pOK-G15 which include only bases 319 to 843 and 565 to 1003 respectively, and contain small fragments which overlap 300 bp of each other, had as much as 65 and 79% stability, respectively. In contrast, plasmid pOK-G16 (bases 1003 to 1590) which covers only ORF-3 only was as unstable as pOK, indicating that ORF-3 alone does not function as a stabilizing element. These results indicate that it is difficult to pinpoint the localized sequence of GH$_3$ fragment which is 100% responsible for the stable maintenance of pOK. It is noted however that all the active fragment contained at least one inverted repeat. All fragments with inverted repeats were active except for pOK-G16.

DISCUSSION

Stable maintenance of bacterial plasmids depends on synthesis of a sufficient copy number of the plasmid (at least 2 copies) in the dividing cell and proper distribution of the replicated plasmids to daughter cells (at least one copy per cell). Dysfunction of either system results in plasmid loss. This is phenotypically manifested as an unstable plasmid. The temperature sensitive instability of pOK, a derivative of Rts1 having its replicon and the kanamycin resistant gene, is apparently due to temperature sensitive functioning of the partition mechanism. The major reason for this conclusion is that plasmid pOK replicates 30 fold in 8 h at the nonpermissive temperature (FIG. 11). During the initial 4 h at 42.5° C. the rate of replication was identical to that at 32° C. In addition, during 8 h of exponential growth of *E. coli* harboring pOK(ΔE+H) the cells multiplied 21 times without producing detectable plasmidless cells. This means that plasmid must have multiplied at least 21 times. This establishes the fact that replication of original Rts1 replicon is not temperature sensitive. The temperature sensitive instability of Rts1 (36) was originally believed to be largely due to temperature sensitive replication of Rts1 derivatives, pTW20 and pTW601 (14, 15, 18, 35). However, we have shown in previous studies that Rts1 does replicate, though a bit slower at 42° C. (8, 9, 42).

Our sequencing data of the replication region of pOK and intact Rts1 revealed that some nucleotides in this region are not identical with those which have been reported previously (19) with the replication region of pTW20 (and therefore pTW601). This is understandable on the basis that pTW20 was derived from Rts1 by mutagen treatment (34). However, the sequence obtained in the present application is in agreement with what has been reported by Terawaki et al. in the following points. It consists of an origin sequence (ori), a repA gene encoding a protein essential for plasmid replication (repA protein), and direct repeat sequences which regulate replication, thereby expressing incompatibility (inc) (15, 19, 20). On the other hand, the sequence data reported herein indicates an important difference in the repA protein at 260th amino acid. It is asparagine (AAT) with pTW20 (19) while it is tyrosine (TAT) with Rts1. The repA protein of pTW20 has been reported to bind to the ori region less efficiently at the nonpermissive temperature than at the permissive temperature (18, 35). Therefore, the amino acid difference observed in the repA region may explain observed apparent difference between Rts1 replicon and pTW20 replicon regarding replication at the nonpermissive temperature. It should be recalled that repA of P1 plasmid is very similar to that of Rts1. The corresponding amino acid at the 259th position of P1 is tyrosine, the same as found with Rts1. This further supports the notion that the change was brought about by the mutagen treatment used to obtain pTW20 from Rts1.

There are several known DNA sequences which perform proper partitioning of plasmids between dividing daughter cells. Two protein coding regions and a centromere-like cis-acting region are involved in the par function of P1 and F plasmids(1, 5, 22, 26). Two gene products, one inhibiting the growth of host cells which have lost the plasmid and the other inhibiting the action of this protein, are involved in partitioning of R1, R100, and F plasmids (29, 37, 38 ref). A cis-acting short DNA segment without involving proteins has been reported to partition pSC101, ColE1 and pSL11 plasmids (4, 21, 23, 24, 31, 39). The par regions involving the par proteins are in general of large size, while those cis-acting DNA are of small size. The pOK DNA sequence is consistent with the latter which does not involve proteins. The par locus of other plasmids have been reported to map often in close proximity to the replication origin (23, 26). Studies leading to the present invention have not exactly localized the par of the Rts1 replicon, but it is assumed that it is between nucleotide 450 and 1650 from the deletion experiments involving the rep region. Thus, deletion of upstream (nucleotides from 240 to 488) or downstream (nucleotides from 1640 to 1854) did not eliminate partition function of this plasmid at 32° C.

This preliminary localization of the temperature sensitive par region of pOK was made on the assumption that the par of Rts1 is also close to the origin of replication. This region corresponds to the incII region. The preliminary localization of the par in this region is further supported by the fact that within this region a sequence TGCAATAAAAGCCCTTC SEQ. ID. NO:15 (nucleotides from 1318 to 1334) is found. The identical sequence except for two bases to this is present in the par region of pSC101 (nucleotides from 210 to 194, 24). In addition, there is an 8 bp imperfect inverted repeat (nucleotides from 665 to 688) in this region. This is consistent with the fact that a common feature of the par region, not dependent on protein, is the presence of inverted repeats (21, 24).

Regarding the molecular mechanism of the temperature sensitive partition at this hypothetical par region, it has been postulated that this region functions through DNA configuration changes catalyzed by the gyrase, as proposed with the par region of pSC101 (39). As a matter of fact, the common nucleotide sequence present both in pSC101 par region and this region, as described above, is included in the binding site of the gyrase to the pSC101 par region. For the possible mechanism of temperature sensitivity, the inverted repeat (within nucleotides from 665 to 688) is important. Half (4 out of 8) of this inverted region is consecutive a A sequence and one is mismatch pair. The AT pair has been shown to undergo partial denaturation at high temperature (42° C.) (Mochida et al. to be published). It is conceivable that this short inverted repeat lose its stem loop structure at 42.5° C. resulting in the loss of the par function. Presence of inverted repeat in the par region of pSC101, ColE1, and pSL11 further supports this notion. The fact that every small stabilizing fragment of $GH_3$ contains at least one inverted repeat is consistent with this postulation. As discussed below, none of these inverted repeats in the stabilizing fragment contains consecutive AT pairs suggesting that their stem loop structure will not be changed 42.5° C.

The above hypothesis for the temperature sensitive partition must accommodate the observation that a DNA fragment ($GH_3$) from Rts1 has a remarkable stabilizing effect on pOK at 42.5° C. In other words, inclusion of this fragment restored the par function at 42.5° C. One can postulate that $GH_3$ can function as a par itself. This was supported by the fact that $GH_3$ functions only with cis configuration (FIG. 17a). Furthermore existence of the $GH_3$ sequence in the compatible plasmid inhibited the partitioning of the stabilized pOK containing $GH_3$ (FIG. 17b). This suggests that $GH_3$ may occupy the celluar par site during cell division. What DNA sequence of $GH_3$ is responsible for this? The experiments reported herein ruled out the possible involvement of three ORFs. It is postulated that $GH_3$s four inverted repeats play a role in this stabilization. The fact that smaller fragments of $GH_3$ are totally or partially functional can also be explained because all active fragments contained at least one inverted repeats. Conversely, except for pOK-G16, all of the fragments with inverted repeats were active. The reason why pOK-G16 was not stable remains obscure. One can imagine the possibility that depending on the site of the insertion of this fragment (there are two BamHI sites of pOK) and direction of the inserted fragment, the inverted repeat may not function.

It should be noted that the relationship between the stabilizing activity of $GH_3$ and the temperature dependent instability of the parent plasmid Rts1 (28) is not clear at the moment. Since the original Rts1 is unstable at 42° C. the complete stabilization of pOK by $GH_3$ suggests the presence of additional elements which modify this activity of $GH_3$ in the original Rts1. In fact previous publications have described a DNA fragment from Rts1 which makes plasmid pUC19 very unstable (32). Since $GH_3$ is situated at least 15 kb away from the Rts1 replicon, and many of the par regions so far described are localized near the replicon, the actual role of $GH_3$ in Rts1 may not be for partition.

The plasmids described herein, pOKcop and the mutant P1, with or without the additional insertion of $GH_3$, are useful because of their ability to coexist, in a high copy number, in a host cell with other available vectors. As a result, the mutant plasmids described herein can be ligated or recombinantly combined with known or available vectors (with or without the use of any additional linking nucleotide sequences), wherein the available vectors comprise nucleotide sequences which code for genetic information of interest. In a particular embodiment, the mutant plasmids of the invention are ligated to known and available vectors containing an expressible gene of interest, and then utilized to transform a host cell, such as a gram negative bacterial like *E. coli*. The transformed host cell can then be cultured and the high copy numbers of the plasmid results in the ability to express the gene of interest so as to provide significantly increased high yields of the expression product, such as a protein.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

REFERENCES

1. Abeles, A. L., S. A. Friedman, and S. J. Austin. 1985. Partition of unit-copy miniplasmids to daughter cells III. The DNA sequence and functional organization of the P1 partition region. J. Mol. Biol. 185: 261–272.

2. Bernardi, A., and F. Bernardi. 1984. Complete sequence of pSC101. Nucleic Acid Res. 12: 9415–9426.
3. Birnboim, H. C., and J. Doly. 1979. A rapid alkaline extraction procedure for screening recombinant plasmid DNA. Nucleic Acid Res. 7:1513–1523.
4. Chang, S., S. Y. Chang, and Gray. 1987. Structural and genetic analyses of a par locus that regulates plasmid partition in *Bacillus subtilis*. J. Bacteriol. 169:3952–3962.
5. Coetzee, J. N., N. Datta, and R. W. Hedges. 1972. R factors from Proteus rettgeri. J. Gen. Microbiol. 72:543–552.
6. Davis, M. A., K. A. Martin, and S. J. Austin. 1990. Specificity switching of the P1 plasmid centromere-like site. The EMBO Journal. 9:991–998.
7. DiJoseph, C. G., M. S. Bayer, and A. Kaji. 1973. Host cell growth in the presence of the thermosensitive drug resistance factor Rts1. J. Bacteriol. 115: 399–410.
8. DiJoseph, C. G., and A. Kaji. 1974. The thermosensitive lesion in the replication of the drug resistance factor, Rts1. Proc. Natl. Acad. Sci. USA. 71:2515–2519.
9. DiJoseph, C. G., and A. Kaji. 1974. Molecular nature of the deoxyribonucleic acid of a thermosensitive R factor, Rts1. J. Bacteriol. 120:1364–1369.
10. Franklin, N. C., and S. E. Luria. 1961. Transduction by bacteriophage P1 and the properties of the lac genetic region in *E. coli* and *S. dysenteriae*. Virology. 15:299–311.
11. Hanahan, D. 1985. Techniques for transformation of *E. coli*. In "DNA cloning: a practical approach" (D. M. Glover, ed.), pp 109–135. IRL Press, Oxford.
12. Iida, S., J. Mayer, P. Linder, N. Goto, R. Nakaya, H. 35. Reif, and W. Arber. 1982. The kanamycin resistance transposon Tn2680 derived from the R plasmid Rts1 and carried by phage P1Km has flanking 0.8-Kb-long direct repeats. Plasmid. 8:187–198.
13. Ishaq, M., and A. Kaji. 1980. Mechanism of T4 phage restriction by plasmid Rts1. J. Biol. Chem. 255: 4040–4047.
14. Itoh, Y., Y. Kamio, Y. Furuta, and Y. Terawaki. 1982. Cloning of the replication and incompatibility regions of a plasmid derived from Rts1. Plasmid. 8:232–243.
15. Itoh, Y., Y. Kamio, and Y. Terawaki. 1987. Essential DNA sequence for the replication of Rts1. J. Bacteriol. 169:1153–1160.
16. Joshi, A. K., B. Varsha, and G. Ames. 1991. Rapid polymerase chain reaction amplification using intact bacterial cells. BioTechniques. 10:42–45.
17. Kaji, A., H. Yoshimoto, T. Yamamoto, and S. Finver. 1982. Studies on various phenotypes of drug resistance factor, Rts1. In "Drug Resistance in Bacteria" (S. Mitsuhashi, ed.), pp59–69. Japan. Sci. Soc. Tokyo/Thieme Stratton, N.Y.
18. Kamio, Y., Y. Itoh, and Y. Terawaki. 1988. Purification of Rts1 repA protein and binding of the protein to mini-Rts1 DNA. J. Bacteriol. 170:4411–4414.
19. Kamio, Y., A. Tabuchi, Y. Itoh, H. Katagiri, and Y. Terawaki. 1984. Complete nucleotide sequence of mini-Rts1 and its copy mutant. J. Bacteriol. 158:307–312.
20. Kamio, Y., and Y. Terawaki. 1983. Nucleotide sequence of an incompatibility region of mini-Rts1 that contains five direct repeats. J. Bacteriol. 155:1185–1191.
21. Leung, D. W., E. Chen, G. Cachianes, and D. V. Goeddle. 1985. Nucleotide sequence of the partition function of *Esherishia coli* plasmid ColE1. DNA. 4: 351–335.
22. Martin, K. A., S. A. Friedman, and S. J. Austin. 1987. Partition site of the P1 plasmid. Proc. Natl. Acad. Sci. USA. 84:8544–8547.
23. Meacock, P., and S. N. Cohen. 1980. Partitioning of bacterial plasmids during cell division: a cis-acting locus that accomplishes stable plasmid inheritance. Cell. 20:529–542.
24. Miller, C. A., W. T. Tucker, P. A. Meacock, P. Gustafsson, and S. N. Cohen. 1983. Nucleotide sequence of the partition locus of *Esherishia coli* plasmid pSC101. Gene. 24:309–315.
25. Mochida, S., H. Tsuchiya, K. Mori, and A. Kaji. 1991. Three short fragments of Rts1 DNA are responsible for the temperature-sensitive growth phenotype (Tsg) of host bacteria. J. Bacteriol. 173:2600–2607.
26. Ogura, T., and S. Hiraga. 1983. Partition mechanism of F plasmid: two plasmid gene-encoded products and a cis-acting region are involved in partition. Cell. 32:351–360.
27. Okawa, N., M. Tanaka, So Finver, and A. Kaji. 1987. Identification of the Rts1 DNA fragment responsible for temperature sensitive growth of host cells harboring a drug resistance factor Rts1. Biochem. Biophys. Res. Commun. 142: 1084–1088.
28. Okawa, N., H. Yoshimoto, and A. Kaji. 1985. Identification of an Rts1 DNA fragment conferring temperature-dependent instability to vector plasmids. Plasmid. 13:88–98.
29. Rasmussen, P. B., K. Gerdes, and S. Molin. 1987. Genetic analysis of the parB$^+$locus of plasmid R1. Mol. Gen. Genet. 209:122–128.
30. Sanger, F., S. Nicklen, and A. R. Coulson. 1977. DNA sequencing with chain-terminating inhibitors. Proc. Natl. Acad. Sci. USA. 74:5463–5467.
31. Summers, D. K., and D. J. Sherratt. 1984. Multimerization of high copy number plasmids causes instability: ColE1 encodes a determinant essential for plasmid monomerization and stability. Cell. 36: 1097–1103.
32. Tanaka, M., N. Okawa, K. Mori, Y. Suyama, and A. Kaji. 1988. Nucleotide sequence of an Rts1 fragment causing temperature-dependent instability. J. Bacteriol. 170: 1175–1182.
33. Terawaki, Y., Y. Kakizawa, H. Takayasu, and M. Yoshikawa. 1968. Temperature sensitivity of cell growth in *Esherichia coli* associated with temperature sensitive R(KM) factor. Nature (London). 219:284–285.
34. Terawaki, Y., Y. Kobayashi, H. Matsumoto, and Y. Kamio. 1980. An Rts1-derived plasmid conferring UV sensitivity on *Esherichia coli* host. Biochem. Biophys. Res. Commun. 97:694–699.
35. Terawaki, Y., H. Nozue, T. Hayashi, Y. Kamio, and Y. Itoh. 1990. Effects of mutations in the repA gene of plasmid Rts1 on plasmid replication and autorepressor function. J. Bacteriol. 172:786–792.
36. Terawaki, Y., H. Takayasu, and T. Akiba. 1967. Thermosensitive replication of a kanamycin resistance factor. J. Bacteriol. 94:687–690.
37. Tsuchimoto, S., Y. Nishimura, and E. Ohtsubo. 1992. The stable maintenance system pem of plasmid R100: Degradation of PemI protein may allow PemK protein to inhibit cell growth. J. Bacteriol. 174: 4205–4211.
38. Tsuchimoto, S., H. Ohtsubo, and E. Ohtsubo. 1988. Two genes, pemK and pemI, responsible for stable maintenance plasmid R100. J. Bacteriol. 170:1461–1466.
39. Wahle, E., and A. Kornberg. 1988. The partition locus of plasmid pSC101 is a specific binding site for DNA gyrase. The EMBO Journal. 7:1889–1895.
40. Williams, D. R., and C. M. Thomas. 1992. Active partitioning of bacterial plasmids. J. Gen. Microbiol. 138:1–16

41. Yamamoto, T., S. Finver, T. Yokota, J. Bricker, and A. Kaji. 1981. The region controlling the thermosensitive effect of plasmid Rts1 on host growth is separate from the Rts1 replication region. J. Bacteriol. 146:85–92.

42. Yamamoto, T., and A. Kaji. 1977. Replication of thermosensitive Rts1 plasmid deoxyribonucleic acid at the nonpermissive temperature. J. Bacteriol. 132: 90–99. Abeles, A. L., Snyder, K. M., and Chattoraj, D. K. 1984. P1 plasmid replication:Replicon structure. J. Mol. Biol. 173: 307–324.

43. Kaji, A., Okawa, N., Tanaka, M., Mori, K., and Finver, S., 1988. Rts1: A Multiphenotypic, Unusual Temperature Sensitive Drug Resistance Factor, Roots of Mol. Biochem. 397–406.

44. Maniatis, T., E. F. Fritsch, and J. Sambrook. 1982. Molecular cloning: a laboratory manual. Cold Spring Harbor Laboratory, Cold Spring Harbor, N.Y.

45. Abeles, A. L., Snyder, K. M., and Chattoraj, D. K. 1984. P1 plasmid replication:Replicon structure. J. Mol. Biol. 173: 307–324.

46. Chattoraj, D., Abeles, A. L., and Yarmolinsky, M. B. 1985. P1 Plasmid Maintenance: A Paradigon of Precise Control. In D. R. Helsinki, S. N. Cohen, D. B. Clewell, D. A. Jackson and A. Holbender (ed.) *Plasmids in Bacteria*, Plenum Pub. Co., New York, N.Y.

I claim:

1. The plasmid pOKcop which is a mutant of the plasmid Rts1 and has the sequence of SEQ ID NO:4.

2. A DNA molecule comprising the repA portion of the plasmid pOKcop according to claim 1, wherein the repA portion has the sequence of SEQ ID NO:5.

3. A DNA molecule comprising a mutant repA portion of the plasmid P1 wherein the mutant repA portion has the sequence of SEQ ID NO:10.

4. A plasmid comprising the nucleotide sequence of the plasmid of claim 1 (SEQ ID NO:4), and the nucleotide sequence of the GH₃ fragment (SEQ ID NO:14).

5. A plasmid comprising the DNA molecule of claim 2, further including the nucleotide sequence of the GH₃ fragment (SEQ ID NO:14).

6. A plasmid comprising the DNA molecule of claim 3, further including the nucleotide sequence of the GH₃ fragment (SEQ ID NO:14).

7. A transformed host cell harboring a plasmid of any one of claims 1 or 4–6.

8. A transformed host cell harboring a plasmid, the plasmid comprising the nucleotide sequence of the plasmid of claim 1 or 4, and additional nucleotide sequences which code for genetic information of interest.

9. A transformed host cell according to claim 8, wherein said additional nucleotide sequences comprise a gene of interest being expressible in said host cell.

10. A transformed host cell according to claim 8, wherein said cell is a bacterium.

11. A transformed host cell according to claim 10, wherein said bacterium is *E. coli*.

12. A transformed host cell according to claim 9, wherein said gene of interest is heterologous to said host cell.

13. A transformed host cell according to claim 12, wherein said gene of interest codes for a protein.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 3356 base pairs
( B ) TYPE: nucleic acid
( C ) STRANDEDNESS: both
( D ) TOPOLOGY: linear ( i i ) MOLECULE TYPE: DNA (genomic)

( i i i ) HYPOTHETICAL: NO ( i x ) FEATURE:
( A ) NAME/KEY: -
( B ) LOCATION: 1..3356
( D ) OTHER INFORMATION: /note="Insert in plasmid pOK, see Fig 4."

( x i ) SEQUENCE DESCRIPTION: SEQ ID NO:1:

```
GATCCCGAGC  TTATCAGATG  TATTCTGATG  CGGTTCGATA  AACCTGTCTT  ACCAGAAAGG    60
GAACAAACTC  AGATGAAAAT  CATCAAAATC  TATACACCTC  ATGAACTGGC  TCTGTTGAGA   120
GATCCTGCTT  TCAGATTGAT  AGTGATAGAG  GCTATTGGTA  CAGATGGATT  CGTTGAGCAA   180
TATAATCTAC  TAAATAATGT  CTCACTTAAT  CAGCCTAAGA  ACGGTCTGGA  GGTATTAATC   240
GATCAGGCTA  CAGGGGCAGC  AGATAAGCAT  CAACGCGTAT  ACTTCAACGG  ACTTCTTAAA   300
TTTATCTATG  AAACTGTATA  CTTACGGTTA  GAACCGATGG  CTTTGGGGTA  GTTCCGGGAA   360
CCGTTGTCGG  GTAATGAATG  GGTTTACCTT  TCATTGCCCG  GCAGCGGTTG  GACAAGCGTA   420
GCGCGTCAGA  TATTCCTCCA  CATTACCATC  ATTTAAAGTT  ATCCACATAT  CCACCGTGTA   480
GATCCAATAA  TAGATCCATA  GAGAGATCCA  GATAAAACCA  AAAAGATCCC  CGTGGTCTGT   540
AGCCTTACTG  CCACAAGGCT  TACAACGTTT  TTCGGTGTGT  GCTGAGGGGA  AAAAGGTGTG   600
TGCTGAGGGG  AAGAAAGTGT  GTGTTACGGG  GATTGGGGTG  TGTGCTGAGG  GGAAAAAAGG   660
TGGGCGTCAC  GGGGAAAATG  TGATACTTTT  CCACAATCGT  AGCATTTACG  TGGGGGGGAA   720
TTATTTTATT  ATGGAAACTC  AACTAGTTAT  ATCTGATGTG  TTATTTGGTA  ACACGGAAGA   780
AAAACAAAAA  CCATTAACAG  TTAATGAACT  GAATACAATT  CAACCAGTGG  CCTTTATGCG   840
CCTTGGCCTG  TTTGTGCCTA  AACCATCAAG  GTCATCTGAC  TACAGCCCGA  TGATTGATGT   900
CAGTGAATTA  AGTTCTACCT  TTGAATTTGC  AAGACTTGAG  GGGTTACTG   ACATAAAAAT   960
CACTGGTGAA  CGTCTTGATA  TGGATACTGA  TTTCAAGGTG  TGGATCGGCA  TAGTCAAAGC  1020
```

```
GTTCAGCAAG  TACGGGATTT  CGTCAAACCG  CATCAAACTA  AAGTTTTCTG  AGTTCGCAAA       1080
AGATTGTGGT  TTCCCCGGTA  AAAAACTGGA  CAAGAAACTG  AGAGCGCATA  TAGATGAATC       1140
GCTTCGTAAA  ATCAGGGGGA  AATCGATCTC  ATTTAAGCGA  GGCAAAGATT  CACAATCTGC       1200
ATATCATACC  GGCCTCATAA  AGATAGCCTA  TTTCAATGCC  GATACAGACG  TTGTGGAACT       1260
GGAAGCAGAC  GAGCGATTAT  GGGAGTTATA  CTACTTTGAT  TATCGTGTTG  TTCTTCAACT       1320
ACATGCAATA  AAAGCCCTTC  CACGTCTAGA  AGTTGCACAA  GCCCTGTATA  CCTTCCTTGC       1380
AAGCCTTCCA  AGTAACCCGG  CTCCTATCTC  TTTTAAACGC  CTACGTGAAA  GGTTGTCTCT       1440
GATCAGTCAG  GTTAAAGAAC  AGAATCGAAT  AATCAAAAAA  GCGATTACTA  AGCTGATAGA       1500
TATCGGCTAT  TTGGACGCTT  CTATGGTGAA  AAAAGGACAA  GAGAATTACC  TCATCATTCA       1560
CAAGCGAAGT  CCAAAGCTAA  GTGTAATCAA  CGAATAAGTG  TGCCTGTGGT  TTGGCTGTCA       1620
ATGAAAAGTG  TGTGTCAGGG  GGGTTAACAG  TCATTGCAAA  GGTGTGTGTC  AGGGGAACT        1680
GATCGCCTCT  CTGGCAAGGT  GTGTGTCAGG  GGGAATGCC   ACTGGCAAGG  TGTGCGTCAG       1740
GGGGAAAATT  GGTGGTTTTC  CCTCCGAGTG  AGTATCACGG  GGCGTAATTA  TCACCGGTAA       1800
AGTGTGTGTC  AGGGGGAAGG  AATTGGCTTT  CGTTCGGTGT  GTGCCAAGGG  GTTTGACGGG       1860
AATTCGGGAT  CCCGAACGGC  CAGATGCAAC  TTTCGCCATA  TACGACGGCG  TTCCTGGCCA       1920
TGCTTTTTGA  CTTTCCACTC  GCCTTCACCG  AAGACCTTCA  GCCCGGTGGA  ATCAATTACC       1980
AGGTGTGCGA  TTTCACCCCG  GGTGGGCGTT  TTGAAACTGA  CATTAACCGA  CTTTGCCCGC       2040
CTGCTGACAC  AGCTGTAATC  CGGGCAGCGT  AGCGGAACGT  TCATCAGAGA  AAAAATGGAA       2100
TCAATAAAGC  CCTGCGCAGC  GCGCAGGGTC  AGCCTGAATA  CGCGTTTAAT  GACCAGCACA       2160
GTCGTGATGG  CAAGGTCAGA  ATAGCGCTGA  GGTCTGCCTC  GTGAAGAAGG  TGTTGCTGAC       2220
TCATACCAGG  CCTGAATAGC  TTCATCATCC  AGCCAGAAAG  TTATGGAGCC  ACGGTTGATG       2280
AGGGCTTTAT  TGTAGGTGGG  CCAGTTGGTG  ATTTTGAACT  TTTGCTTTGC  CACGGAACGG       2340
TCTGCGTTGT  CGGGAAGATG  CGTGATCTGA  TCCTTCAACT  CAGCAAAAGT  TCGATTTATT       2400
CAACAAAGCC  CGTTGTGTCT  CAAAATCTCT  GATGTTACAT  TGAACAAGAT  AAAAGTATAT       2460
CATCATGAAC  AATAAAACTG  TCTGCTTACA  TAAACAGTAA  TACAAGGAGC  GTTATGAGCC       2520
ATATTCAACG  GGAGACGTCT  TGCTCGAGGC  CGCGATTAAA  TTCCAACCTG  GATGCTGATT       2580
TATATGGGTA  TAGATGGGCT  CGCGATAATG  TCGGGCAATC  AGGTGCGACA  ATCTATCGAT       2640
TGTATGGGAA  GCCCGATGCG  CCAGAGTTGT  TTCTGAAACA  TGGCAAAGGT  AGCGTTGCCA       2700
ATGATGTTAC  AGATGAGATG  GTCAGACTAA  ACTGGCTGAC  GGCATTTATG  CCTCTTCCGA       2760
CCATCAAGCA  TTTTATCCGT  ACTCCTGATG  ATGCATGGTT  ACTCACCACT  GCGATCCCCG       2820
GGAAAACAGC  ATTCCAGGTA  TTAGAAGAAT  ATCCTGATTC  AGGTGAAAAT  ATTGTTGATG       2880
CGCTGGCAGC  GTTCCTGCGC  CGGTTGCATT  CGATTCCTGT  TTGTAATTGT  CCTTTTAACA       2940
GCGATCGCGT  ATTTCGTCTC  ACTCAGGCGC  AATCACGAAT  GAATAACGGT  TTGGTTGATG       3000
CGAGTGATTT  TGATGACGAG  CGTAATGGCT  GGCCTGTTGA  ACAAGTCTGG  AAAGAAATGC       3060
ATAAGCTTTT  GCCATTCTCA  CCGGATTCAG  TCGTCACTCA  TGGTGATTTC  TCACTTGATA       3120
ACCTTATTTT  TGACGAGGGG  AAATTAATAG  GTTGTATTGA  TGTTGGACGA  GTCGGAATCG       3180
CAGACCGATA  CCAGGATCTT  GCCATCCTAT  GGAACTGCCT  CGGTGAATTT  TCACCTTCAT       3240
TACAGAAACG  GTTTTTTTAT  AAATATGGCA  TTGATAATCC  TGATATGAAT  AAATTGCAGT       3300
TTCATTTGAT  GCTCGATGAG  TTTTTCTGAT  AGCTAGTCTT  TGGTTTCCCT  GTCCGG           3356
```

( 2 ) INFORMATION FOR SEQ ID NO:2:

( i ) SEQUENCE CHARACTERISTICS:
    ( A ) LENGTH: 867 base pairs
    ( B ) TYPE: nucleic acid
    ( C ) STRANDEDNESS: both
    ( D ) TOPOLOGY: linear ( i i ) MOLECULE TYPE: DNA (genomic)

( i i i ) HYPOTHETICAL: NO ( i x ) FEATURE:
    ( A ) NAME/KEY: CDS
    ( B ) LOCATION: 1..864
    ( D ) OTHER INFORMATION: /product="RepA from plasmid pOK, see Fig. 5"

( x i ) SEQUENCE DESCRIPTION: SEQ ID NO:2:

```
ATG GAA ACT CAA CTA GTT ATA TCT GAT GTG TTA TTT GGT AAC ACG GAA      48
Met Glu Thr Gln Leu Val Ile Ser Asp Val Leu Phe Gly Asn Thr Glu
 1               5                  10                  15

GAA AAA CAA AAA CCA TTA ACA GTT AAT GAA CTG AAT ACA ATT CAA CCA      96
Glu Lys Gln Lys Pro Leu Thr Val Asn Glu Leu Asn Thr Ile Gln Pro
             20                  25                  30

GTG GCC TTT ATG CGC CTT GGC CTG TTT GTG CCT AAA CCA TCA AGG TCA     144
Val Ala Phe Met Arg Leu Gly Leu Phe Val Pro Lys Pro Ser Arg Ser
         35                  40                  45

TCT GAC TAC AGC CCG ATG ATT GAT GTC AGT GAA TTA AGT TCT ACC TTT     192
Ser Asp Tyr Ser Pro Met Ile Asp Val Ser Glu Leu Ser Ser Thr Phe
     50                  55                  60

GAA TTT GCA AGA CTT GAG GGG TTT ACT GAC ATA AAA ATC ACT GGT GAA     240
Glu Phe Ala Arg Leu Glu Gly Phe Thr Asp Ile Lys Ile Thr Gly Glu
 65                  70                  75                  80

CGT CTT GAT ATG GAT ACT GAT TTC AAG GTG TGG ATC GGC ATA GTC AAA     288
Arg Leu Asp Met Asp Thr Asp Phe Lys Val Trp Ile Gly Ile Val Lys
                 85                  90                  95

GCG TTC AGC AAG TAC GGG ATT TCG TCA AAC CGC ATC AAA CTA AAG TTT     336
Ala Phe Ser Lys Tyr Gly Ile Ser Ser Asn Arg Ile Lys Leu Lys Phe
            100                 105                 110

TCT GAG TTC GCA AAA GAT TGT GGT TTC CCC GGT AAA AAA CTG GAC AAG     384
Ser Glu Phe Ala Lys Asp Cys Gly Phe Pro Gly Lys Lys Leu Asp Lys
        115                 120                 125

AAA CTG AGA GCG CAT ATA GAT GAA TCG CTT CGT AAA ATC AGG GGG AAA     432
Lys Leu Arg Ala His Ile Asp Glu Ser Leu Arg Lys Ile Arg Gly Lys
    130                 135                 140

TCG ATC TCA TTT AAG CGA GGC AAA GAT TCA CAA TCT GCA TAT CAT ACC     480
Ser Ile Ser Phe Lys Arg Gly Lys Asp Ser Gln Ser Ala Tyr His Thr
145                 150                 155                 160

GGC CTC ATA AAG ATA GCC TAT TTC AAT GCC GAT ACA GAC GTT GTG GAA     528
Gly Leu Ile Lys Ile Ala Tyr Phe Asn Ala Asp Thr Asp Val Val Glu
                165                 170                 175

CTG GAA GCA GAC GAG CGA TTA TGG GAG TTA TAC TAC TTT GAT TAT CGT     576
Leu Glu Ala Asp Glu Arg Leu Trp Glu Leu Tyr Tyr Phe Asp Tyr Arg
            180                 185                 190

GTT GTT CTT CAA CTA CAT GCA ATA AAA GCC CTT CCA CGT CTA GAA GTT     624
Val Val Leu Gln Leu His Ala Ile Lys Ala Leu Pro Arg Leu Glu Val
        195                 200                 205

GCA CAA GCC CTG TAT ACC TTC CTT GCA AGC CTT CCA AGT AAC CCG GCT     672
Ala Gln Ala Leu Tyr Thr Phe Leu Ala Ser Leu Pro Ser Asn Pro Ala
    210                 215                 220

CCT ATC TCT TTT AAA CGC CTA CGT GAA AGG TTG TCT CTG ATC AGT CAG     720
Pro Ile Ser Phe Lys Arg Leu Arg Glu Arg Leu Ser Leu Ile Ser Gln
225                 230                 235                 240

GTT AAA GAA CAG AAT CGA ATA ATC AAA AAA GCG ATT ACT AAG CTG ATA     768
```

```
Val Lys Glu Gln Asn Arg Ile Ile Lys Lys Ala Ile Thr Lys Leu Ile
            245                 250                 255

GAT ATC GGC TAT TTG GAC GCT TCT ATG GTG AAA AAA GGA CAA GAG AAT    816
Asp Ile Gly Tyr Leu Asp Ala Ser Met Val Lys Lys Gly Gln Glu Asn
            260                 265                 270

TAC CTC ATC ATT CAC AAG CGA AGT CCA AAG CTA AGT GTA ATC AAC GAA    864
Tyr Leu Ile Ile His Lys Arg Ser Pro Lys Leu Ser Val Ile Asn Glu
            275                 280                 285

TAA                                                                867
```

( 2 ) INFORMATION FOR SEQ ID NO:3:

( i ) SEQUENCE CHARACTERISTICS:
        ( A ) LENGTH: 288 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Glu Thr Gln Leu Val Ile Ser Asp Val Leu Phe Gly Asn Thr Glu
 1               5                  10                  15

Glu Lys Gln Lys Pro Leu Thr Val Asn Glu Leu Asn Thr Ile Gln Pro
            20                  25                  30

Val Ala Phe Met Arg Leu Gly Leu Phe Val Pro Lys Pro Ser Arg Ser
            35                  40                  45

Ser Asp Tyr Ser Pro Met Ile Asp Val Ser Glu Leu Ser Ser Thr Phe
    50                  55                  60

Glu Phe Ala Arg Leu Glu Gly Phe Thr Asp Ile Lys Ile Thr Gly Glu
65                  70                  75                  80

Arg Leu Asp Met Asp Thr Asp Phe Lys Val Trp Ile Gly Ile Val Lys
                85                  90                  95

Ala Phe Ser Lys Tyr Gly Ile Ser Ser Asn Arg Ile Lys Leu Lys Phe
            100                 105                 110

Ser Glu Phe Ala Lys Asp Cys Gly Phe Pro Gly Lys Lys Leu Asp Lys
            115                 120                 125

Lys Leu Arg Ala His Ile Asp Glu Ser Leu Arg Lys Ile Arg Gly Lys
        130                 135                 140

Ser Ile Ser Phe Lys Arg Gly Lys Asp Ser Gln Ser Ala Tyr His Thr
145                 150                 155                 160

Gly Leu Ile Lys Ile Ala Tyr Phe Asn Ala Asp Thr Asp Val Val Glu
                165                 170                 175

Leu Glu Ala Asp Glu Arg Leu Trp Glu Leu Tyr Tyr Phe Asp Tyr Arg
            180                 185                 190

Val Val Leu Gln Leu His Ala Ile Lys Ala Leu Pro Arg Leu Glu Val
            195                 200                 205

Ala Gln Ala Leu Tyr Thr Phe Leu Ala Ser Leu Pro Ser Asn Pro Ala
        210                 215                 220

Pro Ile Ser Phe Lys Arg Leu Arg Glu Arg Leu Ser Leu Ile Ser Gln
225                 230                 235                 240

Val Lys Glu Gln Asn Arg Ile Ile Lys Lys Ala Ile Thr Lys Leu Ile
                245                 250                 255

Asp Ile Gly Tyr Leu Asp Ala Ser Met Val Lys Lys Gly Gln Glu Asn
            260                 265                 270

Tyr Leu Ile Ile His Lys Arg Ser Pro Lys Leu Ser Val Ile Asn Glu
            275                 280                 285
```

( 2 ) INFORMATION FOR SEQ ID NO:4:

( i ) SEQUENCE CHARACTERISTICS:
        ( A ) LENGTH: 3356 base pairs
        ( B ) TYPE: nucleic acid
        ( C ) STRANDEDNESS: both
        ( D ) TOPOLOGY: linear ( i i ) MOLECULE TYPE: DNA (genomic)

( i i i ) HYPOTHETICAL: NO ( i x ) FEATURE:
        ( A ) NAME/KEY: -
        ( B ) LOCATION: 1..3356
        ( D ) OTHER INFORMATION: /note="mutant plasmid pOKcop, see Fig. 6"

( x i ) SEQUENCE DESCRIPTION: SEQ ID NO:4:

```
GATCCCGAGC TTATCAGATG TATTCTGATG CGGTTCGATA AACCTGTCTT ACCAGAAAGG      60
GAACAAACTC AGATGAAAAT CATCAAAATC TATACACCTC ATGAACTGGC TCTGTTGAGA     120
GATCCTGCTT TCAGATTGAT AGTGATAGAG CTATTGGTA  CAGATGGATT CGTTGAGCAA     180
TATAATCTAC TAAATAATGT CTCACTTAAT CAGCCTAAGA ACGGTCTGGA GGTATTAATC     240
GATCAGGCTA CAGGGGCAGC AGATAAGCAT CAACGCGTAT ACTTCAACGG ACTTCTTAAA     300
TTTATCTATG AAACTGTATA CTTACGGTTA GAACCGATGG CTTTGGGGTA GTTCCGGGAA     360
CCGTTGTCGG GTAATGAATG GGTTTACCTT TCATTGCCCG CAGCGGTTG  GACAAGCGTA     420
GCGCGTCAGA TATTCCTCCA CATTACCATC ATTTAAAGTT ATCCACATAT CCACCGTGTA     480
GATCCAATAA TAGATCCATA GAGAGATCCA GATAAAACCA AAAAGATCCC CGTGGTCTGT     540
AGCCTTACTG CCACAAGGCT TACAACGTTT TTCGGTGTGT GCTGAGGGGA AAAGGTGTG     600
TGCTGAGGGG AAGAAAGTGT GTGTTACGGG GATTTGGGTG TGTGCTGAGG GGAAAAAAGG    660
TGGGCGTCAC GGGGAAAATG TGATACTTTT CCACAATCGT AGCATTTACG TGGGGGGAA    720
TTATTTTATT ATGGAAACTC AACTAGTTAT ATCTGATGTG TTATTTGGTA ACACGGAAGA    780
AAAACAAAAA CCATTAACAG TTAATGAACT GAATACAATT CAACCAGTGG CCTTTATGCG    840
CCTTGGCCTG TTTGTGCCTA AACCATCAAG GTCATCTGAC TACAGCCCGA TGATTGATGT    900
CAGTGAATTA AGTTCTACCT TTGAATTTGC AAGACTTGAG GGGTTACTG  ACATAAAAAT    960
CACTGGTGAA CGTCTTGATA TGGATACTGA TTTCAAGGTG TGGATCGGCA TAGTCAAAGC   1020
GTTCAGCAAG TACGGGATTT CGTCAAACCG CATCAAACTA AAGTTTCTG  AGTTCGCAAA   1080
AGATTGTGGT TTCCCCGGTA AAAACTGGA  CAAGAAACTG AGAGCGCATA TAGATGAATC   1140
GCTTCGTAAA ATCAGGGGGA AATCGATCTC ATTTAAGCGA GGCAAAGATT CACAATCTGC   1200
ATATAATACC GGCCTCATAA AGATAGCCTA TTTCAATGCC GATACAGACG TTGTGGAACT   1260
GGAAGCAGAC GAGCGATTAT GGGAGTTATA CTACTTTGAT TATCGTGTTG TTCTTCAACT   1320
ACATGCAATA AAAGCCCTTC CACGTCTAGA AGTTGCACAA GCCCTGTATA CCTTCCTTGC   1380
AAGCCTTCCA AGTAACCCGG CTCCTATCTC TTTTAAACGC CTACGTGAAA GGTTGTCTCT   1440
GATCAGTCAG GTTAAAGAAC AGAATCGAAT AATCAAAAAA GCGATTACTA AGCTGATAGA   1500
TATCGGCTAT TTGGACGCTT CTATGGTGAA AAAAGGACAA GAGAATTACC TCATCATTCA   1560
CAAGCGAAGT CCAAAGCTAA GTGTAATCAA CGAATAAGTG TGCCTGTGGT TTGGCTGTCA   1620
ATGAAAAGTG TGTGTCAGGG GGGTTAACAG TCATTGCAAA GGTGTGTGTC AGGGGAACT    1680
GATCGCCTCT CTGGCAAGGT GTGTGTCAGG GGGAATGCC  ACTGGCAAGG TGTGCGTCAG   1740
GGGGAAAATT GGTGGTTTTC CCTCCGAGTG AGTATCACGG GGCGTAATTA TCACCGGTAA   1800
```

-continued

| | | | | | | |
|---|---|---|---|---|---|---|
| AGTGTGTGTC | AGGGGGAAGG | AATTGGCTTT | CGTTCGGTGT | GTGCCAAGGG | GTTTGACGGG | 1860 |
| AATTCGGGAT | CCCGAACGGC | CAGATGCAAC | TTTCGCCATA | TACGACGGCG | TTCCTGGCCA | 1920 |
| TGCTTTTTGA | CTTTCCACTC | GCCTTCACCG | AAGACCTTCA | GCCCGGTGGA | ATCAATTACC | 1980 |
| AGGTGTGCGA | TTTCACCCCG | GGTGGGCGTT | TTGAAACTGA | CATTAACCGA | CTTTGCCCGC | 2040 |
| CTGCTGACAC | AGCTGTAATC | CGGGCAGCGT | AGCGGAACGT | TCATCAGAGA | AAAAATGGAA | 2100 |
| TCAATAAAGC | CCTGCGCAGC | GCGCAGGGTC | AGCCTGAATA | CGCGTTTAAT | GACCAGCACA | 2160 |
| GTCGTGATGG | CAAGGTCAGA | ATAGCGCTGA | GGTCTGCCTC | GTGAAGAAGG | TGTTGCTGAC | 2220 |
| TCATACCAGG | CCTGAATAGC | TTCATCATCC | AGCCAGAAAG | TTATGGAGCC | ACGGTTGATG | 2280 |
| AGGGCTTTAT | TGTAGGTGGG | CCAGTTGGTG | ATTTTGAACT | TTTGCTTTGC | CACGGAACGG | 2340 |
| TCTGCGTTGT | CGGGAAGATG | CGTGATCTGA | TCCTTCAACT | CAGCAAAAGT | TCGATTTATT | 2400 |
| CAACAAAGCC | CGTTGTGTCT | CAAAATCTCT | GATGTTACAT | TGAACAAGAT | AAAAGTATAT | 2460 |
| CATCATGAAC | AATAAAACTG | TCTGCTTACA | TAAACAGTAA | TACAAGGAGC | GTTATGAGCC | 2520 |
| ATATTCAACG | GGAGACGTCT | TGCTCGAGGC | CGCGATTAAA | TTCCAACCTG | GATGCTGATT | 2580 |
| TATATGGGTA | TAGATGGGCT | CGCGATAATG | TCGGGCAATC | AGGTGCGACA | ATCTATCGAT | 2640 |
| TGTATGGGAA | GCCCGATGCG | CCAGAGTTGT | TTCTGAAACA | TGGCAAAGGT | AGCGTTGCCA | 2700 |
| ATGATGTTAC | AGATGAGATG | GTCAGACTAA | ACTGGCTGAC | GGCATTTATG | CCTCTTCCGA | 2760 |
| CCATCAAGCA | TTTTATCCGT | ACTCCTGATG | ATGCATGGTT | ACTCACCACT | GCGATCCCCG | 2820 |
| GGAAAACAGC | ATTCCAGGTA | TTAGAAGAAT | ATCCTGATTC | AGGTGAAAAT | ATTGTTGATG | 2880 |
| CGCTGGCAGC | GTTCCTGCGC | CGGTTGCATT | CGATTCCTGT | TTGTAATTGT | CCTTTTAACA | 2940 |
| GCGATCGCGT | ATTTCGTCTC | ACTCAGGCGC | AATCACGAAT | GAATAACGGT | TTGGTTGATG | 3000 |
| CGAGTGATTT | TGATGACGAG | CGTAATGGCT | GGCCTGTTGA | ACAAGTCTGG | AAAGAAATGC | 3060 |
| ATAAGCTTTT | GCCATTCTCA | CCGGATTCAG | TCGTCACTCA | TGGTGATTTC | TCACTTGATA | 3120 |
| ACCTTATTTT | TGACGAGGGG | AAATTAATAG | GTTGTATTGA | TGTTGGACGA | GTCGGAATCG | 3180 |
| CAGACCGATA | CCAGGATCTT | GCCATCCTAT | GGAACTGCCT | CGGTGAATTT | TCACCTTCAT | 3240 |
| TACAGAAACG | GTTTTTTTAT | AAATATGGCA | TTGATAATCC | TGATATGAAT | AAATTGCAGT | 3300 |
| TTCATTTGAT | GCTCGATGAG | TTTTTCTGAT | AGCTAGTCTT | TGGTTTCCCT | GTCCGG | 3356 |

( 2 ) INFORMATION FOR SEQ ID NO:5:

( i ) SEQUENCE CHARACTERISTICS:
        ( A ) LENGTH: 867 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 1..864
        ( D ) OTHER INFORMATION: /product="RepA from pOKcop, see Fig. 7"

( x i ) SEQUENCE DESCRIPTION: SEQ ID NO:5:

| ATG | GAA | ACT | CAA | CTA | GTT | ATA | TCT | GAT | GTG | TTA | TTT | GGT | AAC | ACG | GAA | 48 |
|---|---|---|---|---|---|---|---|---|---|---|---|---|---|---|---|---|
| Met | Glu | Thr | Gln | Leu | Val | Ile | Ser | Asp | Val | Leu | Phe | Gly | Asn | Thr | Glu | |
| 1 | | | | 5 | | | | | 10 | | | | | 15 | | |

| GAA | AAA | CAA | AAA | CCA | TTA | ACA | GTT | AAT | GAA | CTG | AAT | ACA | ATT | CAA | CCA | 96 |
|---|---|---|---|---|---|---|---|---|---|---|---|---|---|---|---|---|
| Glu | Lys | Gln | Lys | Pro | Leu | Thr | Val | Asn | Glu | Leu | Asn | Thr | Ile | Gln | Pro | |
| | | | 20 | | | | | 25 | | | | | 30 | | | |

| GTG | GCC | TTT | ATG | CGC | CTT | GGC | CTG | TTT | GTG | CCT | AAA | CCA | TCA | AGG | TCA | 144 |
|---|---|---|---|---|---|---|---|---|---|---|---|---|---|---|---|---|

|  |  |  |  |  |  |  |  |  |  |  |  |  |  |  |  |  |
|---|---|---|---|---|---|---|---|---|---|---|---|---|---|---|---|---|
| Val | Ala | Phe | Met | Arg | Leu | Gly | Leu | Phe | Val | Pro | Lys | Pro | Ser | Arg | Ser | |
|  |  | 35 |  |  |  |  | 40 |  |  |  |  | 45 |  |  |  |  |
| TCT | GAC | TAC | AGC | CCG | ATG | ATT | GAT | GTC | AGT | GAA | TTA | AGT | TCT | ACC | TTT | 192 |
| Ser | Asp | Tyr | Ser | Pro | Met | Ile | Asp | Val | Ser | Glu | Leu | Ser | Ser | Thr | Phe | |
|  | 50 |  |  |  | 55 |  |  |  |  | 60 |  |  |  |  |  | |
| GAA | TTT | GCA | AGA | CTT | GAG | GGG | TTT | ACT | GAC | ATA | AAA | ATC | ACT | GGT | GAA | 240 |
| Glu | Phe | Ala | Arg | Leu | Glu | Gly | Phe | Thr | Asp | Ile | Lys | Ile | Thr | Gly | Glu | |
| 65 |  |  |  |  | 70 |  |  |  |  | 75 |  |  |  |  | 80 | |
| CGT | CTT | GAT | ATG | GAT | ACT | GAT | TTC | AAG | GTG | TGG | ATC | GGC | ATA | GTC | AAA | 288 |
| Arg | Leu | Asp | Met | Asp | Thr | Asp | Phe | Lys | Val | Trp | Ile | Gly | Ile | Val | Lys | |
|  |  |  |  | 85 |  |  |  |  | 90 |  |  |  |  | 95 |  | |
| GCG | TTC | AGC | AAG | TAC | GGG | ATT | TCG | TCA | AAC | CGC | ATC | AAA | CTA | AAG | TTT | 336 |
| Ala | Phe | Ser | Lys | Tyr | Gly | Ile | Ser | Ser | Asn | Arg | Ile | Lys | Leu | Lys | Phe | |
|  |  |  | 100 |  |  |  |  | 105 |  |  |  |  | 110 |  |  | |
| TCT | GAG | TTC | GCA | AAA | GAT | TGT | GGT | TTC | CCC | GGT | AAA | AAA | CTG | GAC | AAG | 384 |
| Ser | Glu | Phe | Ala | Lys | Asp | Cys | Gly | Phe | Pro | Gly | Lys | Lys | Leu | Asp | Lys | |
|  |  | 115 |  |  |  |  | 120 |  |  |  |  | 125 |  |  |  | |
| AAA | CTG | AGA | GCG | CAT | ATA | GAT | GAA | TCG | CTT | CGT | AAA | ATC | AGG | GGG | AAA | 432 |
| Lys | Leu | Arg | Ala | His | Ile | Asp | Glu | Ser | Leu | Arg | Lys | Ile | Arg | Gly | Lys | |
|  | 130 |  |  |  |  | 135 |  |  |  |  | 140 |  |  |  |  | |
| TCG | ATC | TCA | TTT | AAG | CGA | GGC | AAA | GAT | TCA | CAA | TCT | GCA | TAT | AAT | ACC | 480 |
| Ser | Ile | Ser | Phe | Lys | Arg | Gly | Lys | Asp | Ser | Gln | Ser | Ala | Tyr | Asn | Thr | |
| 145 |  |  |  |  | 150 |  |  |  |  | 155 |  |  |  |  | 160 | |
| GGC | CTC | ATA | AAG | ATA | GCC | TAT | TTC | AAT | GCC | GAT | ACA | GAC | GTT | GTG | GAA | 528 |
| Gly | Leu | Ile | Lys | Ile | Ala | Tyr | Phe | Asn | Ala | Asp | Thr | Asp | Val | Val | Glu | |
|  |  |  |  | 165 |  |  |  |  | 170 |  |  |  |  | 175 |  | |
| CTG | GAA | GCA | GAC | GAG | CGA | TTA | TGG | GAG | TTA | TAC | TAC | TTT | GAT | TAT | CGT | 576 |
| Leu | Glu | Ala | Asp | Glu | Arg | Leu | Trp | Glu | Leu | Tyr | Tyr | Phe | Asp | Tyr | Arg | |
|  |  |  | 180 |  |  |  |  | 185 |  |  |  |  | 190 |  |  | |
| GTT | GTT | CTT | CAA | CTA | CAT | GCA | ATA | AAA | GCC | CTT | CCA | CGT | CTA | GAA | GTT | 624 |
| Val | Val | Leu | Gln | Leu | His | Ala | Ile | Lys | Ala | Leu | Pro | Arg | Leu | Glu | Val | |
|  |  | 195 |  |  |  |  | 200 |  |  |  |  | 205 |  |  |  | |
| GCA | CAA | GCC | CTG | TAT | ACC | TTC | CTT | GCA | AGC | CTT | CCA | AGT | AAC | CCG | GCT | 672 |
| Ala | Gln | Ala | Leu | Tyr | Thr | Phe | Leu | Ala | Ser | Leu | Pro | Ser | Asn | Pro | Ala | |
|  | 210 |  |  |  |  | 215 |  |  |  |  | 220 |  |  |  |  | |
| CCT | ATC | TCT | TTT | AAA | CGC | CTA | CGT | GAA | AGG | TTG | TCT | CTG | ATC | AGT | CAG | 720 |
| Pro | Ile | Ser | Phe | Lys | Arg | Leu | Arg | Glu | Arg | Leu | Ser | Leu | Ile | Ser | Gln | |
| 225 |  |  |  |  | 230 |  |  |  |  | 235 |  |  |  |  | 240 | |
| GTT | AAA | GAA | CAG | AAT | CGA | ATA | ATC | AAA | AAA | GCG | ATT | ACT | AAG | CTG | ATA | 768 |
| Val | Lys | Glu | Gln | Asn | Arg | Ile | Ile | Lys | Lys | Ala | Ile | Thr | Lys | Leu | Ile | |
|  |  |  |  | 245 |  |  |  |  | 250 |  |  |  |  | 255 |  | |
| GAT | ATC | GGC | TAT | TTG | GAC | GCT | TCT | ATG | GTG | AAA | AAA | GGA | CAA | GAG | AAT | 816 |
| Asp | Ile | Gly | Tyr | Leu | Asp | Ala | Ser | Met | Val | Lys | Lys | Gly | Gln | Glu | Asn | |
|  |  |  | 260 |  |  |  |  | 265 |  |  |  |  | 270 |  |  | |
| TAC | CTC | ATC | ATT | CAC | AAG | CGA | AGT | CCA | AAG | CTA | AGT | GTA | ATC | AAC | GAA | 864 |
| Tyr | Leu | Ile | Ile | His | Lys | Arg | Ser | Pro | Lys | Leu | Ser | Val | Ile | Asn | Glu | |
|  |  | 275 |  |  |  |  | 280 |  |  |  |  | 285 |  |  |  | |
| TAA |  |  |  |  |  |  |  |  |  |  |  |  |  |  |  | 867 |

( 2 ) INFORMATION FOR SEQ ID NO:6:

( i ) SEQUENCE CHARACTERISTICS:
        ( A ) LENGTH: 288 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|  |  |  |  |  |  |  |  |  |  |  |  |  |  |  |
|---|---|---|---|---|---|---|---|---|---|---|---|---|---|---|
| Met | Glu | Thr | Gln | Leu | Val | Ile | Ser | Asp | Val | Leu | Phe | Gly | Asn | Thr | Glu |
| 1 |  |  |  | 5 |  |  |  |  | 10 |  |  |  |  | 15 |

| | | | | | | | | | | | | | | |
|---|---|---|---|---|---|---|---|---|---|---|---|---|---|---|
| Glu | Lys | Gln | Lys 20 | Pro | Leu | Thr | Val | Asn 25 | Glu | Leu | Asn | Thr | Ile 30 | Gln | Pro |
| Val | Ala | Phe 35 | Met | Arg | Leu | Gly | Leu 40 | Phe | Val | Pro | Lys | Pro 45 | Ser | Arg | Ser |
| Ser | Asp 50 | Tyr | Ser | Pro | Met | Ile 55 | Asp | Val | Ser | Glu | Leu 60 | Ser | Ser | Thr | Phe |
| Glu 65 | Phe | Ala | Arg | Leu | Glu 70 | Gly | Phe | Thr | Asp | Ile 75 | Lys | Ile | Thr | Gly | Glu 80 |
| Arg | Leu | Asp | Met | Asp 85 | Thr | Asp | Phe | Lys | Val 90 | Trp | Ile | Gly | Ile | Val 95 | Lys |
| Ala | Phe | Ser | Lys 100 | Tyr | Gly | Ile | Ser | Ser 105 | Asn | Arg | Ile | Lys | Leu 110 | Lys | Phe |
| Ser | Glu | Phe 115 | Ala | Lys | Asp | Cys | Gly 120 | Phe | Pro | Gly | Lys | Lys 125 | Leu | Asp | Lys |
| Lys | Leu 130 | Arg | Ala | His | Ile | Asp 135 | Glu | Ser | Leu | Arg | Lys 140 | Ile | Arg | Gly | Lys |
| Ser 145 | Ile | Ser | Phe | Lys | Arg 150 | Gly | Lys | Asp | Ser | Gln 155 | Ser | Ala | Tyr | Asn | Thr 160 |
| Gly | Leu | Ile | Lys | Ile 165 | Ala | Tyr | Phe | Asn | Ala 170 | Asp | Thr | Asp | Val | Val 175 | Glu |
| Leu | Glu | Ala | Asp 180 | Glu | Arg | Leu | Trp | Glu 185 | Leu | Tyr | Tyr | Phe | Asp 190 | Tyr | Arg |
| Val | Val | Leu 195 | Gln | Leu | His | Ala | Ile 200 | Lys | Ala | Leu | Pro | Arg 205 | Leu | Glu | Val |
| Ala | Gln 210 | Ala | Leu | Tyr | Thr | Phe 215 | Leu | Ala | Ser | Leu | Pro 220 | Ser | Asn | Pro | Ala |
| Pro 225 | Ile | Ser | Phe | Lys | Arg 230 | Leu | Arg | Glu | Arg | Leu 235 | Ser | Leu | Ile | Ser | Gln 240 |
| Val | Lys | Glu | Gln | Asn 245 | Arg | Ile | Ile | Lys | Lys 250 | Ala | Ile | Thr | Lys | Leu 255 | Ile |
| Asp | Ile | Gly | Tyr 260 | Leu | Asp | Ala | Ser | Met 265 | Val | Lys | Lys | Gly | Gln 270 | Glu | Asn |
| Tyr | Leu | Ile 275 | Ile | His | Lys | Arg | Ser 280 | Pro | Lys | Leu | Ser | Val 285 | Ile | Asn | Glu |

( 2 ) INFORMATION FOR SEQ ID NO:7:

( i ) SEQUENCE CHARACTERISTICS:
        ( A ) LENGTH: 2316 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 182..571
        ( D ) OTHER INFORMATION: /product="RepA from P1, see Fig. 9"

( i x ) FEATURE:
        ( A ) NAME/KEY: CDS
        ( B ) LOCATION: 891..1748
        ( D ) OTHER INFORMATION: /product="IncC from P1, see Fig. 9"

( x i ) SEQUENCE DESCRIPTION: SEQ ID NO:7:

TAACCACCCT GCCCCCAAAG TGCATTTATG TGTAGGACTG CCAGAGTTTA GCAGTGAATA 60

TTTTGACTGA TCTGCCAGCG TATATCCTCG ATACAGAAAC GATGCTGATG GGATTAACA 120

```
GGAAGAATCG CAACGTTAAT GATTACAACC GAGCTATTAG CGGTAACTAA AAGGGATTTT        180

T ATG TCT GAT AAA GTA ACA GTA AAG CAA ACT ATC AAC AAA GCG ACT           226
  Met Ser Asp Lys Val Thr Val Lys Gln Thr Ile Asn Lys Ala Thr
  1           5                   10                  15

TCA ATC TAC AAA ATT GAG CAA ATC ACT GTT GGC AGG CCA GGA TCT GAA         274
Ser Ile Tyr Lys Ile Glu Gln Ile Thr Val Gly Arg Pro Gly Ser Glu
                20                  25                  30

CAA TAC CGT CGT GCT TTC GAG CTT GCC GAT CAG CTT GGT TTA AAA CAC         322
Gln Tyr Arg Arg Ala Phe Glu Leu Ala Asp Gln Leu Gly Leu Lys His
            35                  40                  45

CCG GAT TGC ATT GAG CAT GTA TTT CCG ACC TAT GCT GAT GAG CAA TGT         370
Pro Asp Cys Ile Glu His Val Phe Pro Thr Tyr Ala Asp Glu Gln Cys
        50                  55                  60

ACT CAT GTT CTT ACC GAA GAG GAT TTT TTC AGC ACT GAA GAA CGA GAA         418
Thr His Val Leu Thr Glu Glu Asp Phe Phe Ser Thr Glu Glu Arg Glu
    65                  70                  75

GGC GTT GAT CGC TGC ATT GGT GTG ATT TGT TCT TCG GTA AGT GAT GAG         466
Gly Val Asp Arg Cys Ile Gly Val Ile Cys Ser Ser Val Ser Asp Glu
80                  85                  90                  95

TTA TTC CCT AAT GTG CCT GAA TAT GGT GGT ATT GGA TAC CAA TTC CTG         514
Leu Phe Pro Asn Val Pro Glu Tyr Gly Gly Ile Gly Tyr Gln Phe Leu
                100                 105                 110

TAC GAG GGC GAT GAG CTT AAA TGC TAT GAA CAT GGT CTT CTC ATC GAA         562
Tyr Glu Gly Asp Glu Leu Lys Cys Tyr Glu His Gly Leu Leu Ile Glu
            115                 120                 125

AGC GTA GAA TAATACGACT CCCTCCAACC GGCTACGTTG CCGGTTTTT                  611
Ser Val Glu
        130

CACTTATCCA CATTATCCAC TGGATAGATC CAATAATCAG GTCCATACAG ATCCCAATTA       671

GATCCATATA GATCCCTGAT CGTTGCAGGC CGCGCCACGT CTGGCTTAGA AGTGTATCGC       731

GATGTGTGCT GGAGGGAAAA CGATGTGTGC TGGAGGGATA AAAATGTGTG CTGACGGGTT       791

GCTAATGTGT GCTGGCGGGA TATAGGATGT GTGTTGACGG GAAAGCTTGG GTAGTTATCA       851

CCACTTATAA AAACTATCCA CACAATTCGG AAAAGTAAT ATG AAT CAA TCA TTT          905
                                            Met Asn Gln Ser Phe
                                            1               5

ATC TCC GAT ATT CTT TAC GCA GAC ATT GAA AGT AAG GCA AAA GAA CTA         953
Ile Ser Asp Ile Leu Tyr Ala Asp Ile Glu Ser Lys Ala Lys Glu Leu
            10                  15                  20

ACA GTT AAT TCA AAC AAC ACT GTG CAG CCT GTA GCG TTG ATG CGC TTG         1001
Thr Val Asn Ser Asn Asn Thr Val Gln Pro Val Ala Leu Met Arg Leu
        25                  30                  35

GGG GTA TTC GTG CCC AAG CCA TCA AAG AGC AAA GGA GAA AGT AAA GAG         1049
Gly Val Phe Val Pro Lys Pro Ser Lys Ser Lys Gly Glu Ser Lys Glu
    40                  45                  50

ATT GAT GCC ACC AAA GCG TTT TCC CAG CTG GAG ATA GCT AAA GCC GAG         1097
Ile Asp Ala Thr Lys Ala Phe Ser Gln Leu Glu Ile Ala Lys Ala Glu
55                  60                  65

GGT TAC GAT GAT ATT AAA ATC ACC GGT CCT CGA CTC GAT ATG GAT ACT         1145
Gly Tyr Asp Asp Ile Lys Ile Thr Gly Pro Arg Leu Asp Met Asp Thr
70                  75                  80                  85

GAT TTC AAA ACG TGG ATC GGT GTC ATC TAC GCG TTC AGC AAA TAC GGC         1193
Asp Phe Lys Thr Trp Ile Gly Val Ile Tyr Ala Phe Ser Lys Tyr Gly
                90                  95                  100

TTG TCC TCA AAC ACC ATC CAG TTA TCG TTT CAG GAA TTC GCT AAA GCC         1241
Leu Ser Ser Asn Thr Ile Gln Leu Ser Phe Gln Glu Phe Ala Lys Ala
            105                 110                 115

TGT GGT TTC CCC TCA AAA CGT CTG GAT GCG AAA CTG CGT TTA ACC ATT         1289
Cys Gly Phe Pro Ser Lys Arg Leu Asp Ala Lys Leu Arg Leu Thr Ile
```

|  |  |  |  |  | 120 |  |  |  |  | 125 |  |  |  |  | 130 |  |  |
|---|---|---|---|---|---|---|---|---|---|---|---|---|---|---|---|---|---|

```
CAT GAA TCA CTT GGA CGC TTG CGT AAC AAG GGT ATC GCT TTT AAG CGC       1337
His Glu Ser Leu Gly Arg Leu Arg Asn Lys Gly Ile Ala Phe Lys Arg
    135                 140                 145

GGA AAA GAT GCT AAA GGC GGC TAT CAG ACT GGT CTG CTG AAG GTC GGG       1385
Gly Lys Asp Ala Lys Gly Gly Tyr Gln Thr Gly Leu Leu Lys Val Gly
150                 155                 160                 165

CGT TTT GAT GCT GAC CTT GAT CTG ATA GAG CTG GAG GCT GAT TCG AAG       1433
Arg Phe Asp Ala Asp Leu Asp Leu Ile Glu Leu Glu Ala Asp Ser Lys
                170                 175                 180

TTG TGG GAG CTG TTC CAG CTT GAT TAT CGC GTT CTG TTG CAA CAC CAC       1481
Leu Trp Glu Leu Phe Gln Leu Asp Tyr Arg Val Leu Leu Gln His His
                185                 190                 195

GCC TTG CGT GCC CTT CCG AAG AAA GAA GCT GCA CAA GCC ATT TAC ACT       1529
Ala Leu Arg Ala Leu Pro Lys Lys Glu Ala Ala Gln Ala Ile Tyr Thr
    200                 205                 210

TTC ATC GAA AGC CTT CCG CAG AAC CCG TTG CCG CTA TCG TTC GCG CGA       1577
Phe Ile Glu Ser Leu Pro Gln Asn Pro Leu Pro Leu Ser Phe Ala Arg
    215                 220                 225

ATC CGT GAG CGC CTG GCT TTG CAG TCA GCT GTT GGC GAG CAA AAC CGT       1625
Ile Arg Glu Arg Leu Ala Leu Gln Ser Ala Val Gly Glu Gln Asn Arg
230                 235                 240                 245

ATC ATT AAG AAA GCG ATA GAA CAG CTT AAA ACA ATC GGC TAT CTC GAC       1673
Ile Ile Lys Lys Ala Ile Glu Gln Leu Lys Thr Ile Gly Tyr Leu Asp
                250                 255                 260

TGT TCT ATT GAG AAG AAA GGC CGG GAA AGT TTT GTA ATC GTC CAT TCT       1721
Cys Ser Ile Glu Lys Lys Gly Arg Glu Ser Phe Val Ile Val His Ser
                265                 270                 275

CGC AAT CCA AAG CTG AAA CTC CCC GAA  TAAGTGTGTG CTGGAGGGAA           1768
Arg Asn Pro Lys Leu Lys Leu Pro Glu
                280                 285

ACCGCATTAA AAAGATGTGT GCTGCCGGGA AGGCTTGTCC AATTTCCTGT TTTTGATGTG    1828

TGCGCTGGAG GGGGACGCCC CTCAGTTTGC CCAGACTTTC CCTCCAGCAC ACATCTGTCC    1888

ATCCGCTTTT CCCTCCAGTG CACATGTAAT TCTCTGCCTT TCCCTCCAGC ACACATATTT    1948

GATACCAGCG ATCCCTCCAC AGCACATAAT TCAATGCGAC TTCCCTCTAT CGCACATCTT    2008

AGACTTTTAT TCTCCCTCCA GCACACATCG AAGCTGCCGG GCAAGCCGTT CTCACCAGTT    2068

GATAGAGAGT GAAGCTTGGC TGCCCATTGA AGCAGGAATC ACCAAAATGA TTCAGGCTAC    2128

AACCTGAACG TAGAAGAAAT CCGCGTCCTT TATGCGTGGA GGATGCCAAA GCATGTTGTG    2188

ACACACTTGG CAAAGGAGTA ACCATGCAGA GAATGCTATG TACAAGCATC TACGCATACA    2248

TTATTATTTT ATGCAGCATT TTTAATTAAA TTCAAAAATA CAGCATAAAG GATGACTTTC    2308

GATGAGTG                                                             2316
```

( 2 ) INFORMATION FOR SEQ ID NO:8:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ser Asp Lys Val Thr Val Lys Gln Thr Ile Asn Lys Ala Thr Ser
 1               5                  10                  15

Ile Tyr Lys Ile Glu Gln Ile Thr Val Gly Arg Pro Gly Ser Glu Gln
            20                  25                  30
```

-continued

```
Tyr Arg Arg Ala Phe Glu Leu Ala Asp Gln Leu Gly Leu Lys His Pro
         35                  40                  45
Asp Cys Ile Glu His Val Phe Pro Thr Tyr Ala Asp Glu Gln Cys Thr
         50                  55                  60
His Val Leu Thr Glu Glu Asp Phe Phe Ser Thr Glu Glu Arg Glu Gly
 65                  70                  75                  80
Val Asp Arg Cys Ile Gly Val Ile Cys Ser Ser Val Ser Asp Glu Leu
                 85                  90                  95
Phe Pro Asn Val Pro Glu Tyr Gly Gly Ile Gly Tyr Gln Phe Leu Tyr
             100                 105                 110
Glu Gly Asp Glu Leu Lys Cys Tyr Glu His Gly Leu Leu Ile Glu Ser
         115                 120                 125
Val Glu
    130
```

( 2 ) INFORMATION FOR SEQ ID NO:9:

( i ) SEQUENCE CHARACTERISTICS:
        ( A ) LENGTH: 286 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Asn Gln Ser Phe Ile Ser Asp Ile Leu Tyr Ala Asp Ile Glu Ser
  1               5                  10                  15
Lys Ala Lys Glu Leu Thr Val Asn Ser Asn Asn Thr Val Gln Pro Val
             20                  25                  30
Ala Leu Met Arg Leu Gly Val Phe Val Pro Lys Pro Ser Lys Ser Lys
         35                  40                  45
Gly Glu Ser Lys Glu Ile Asp Ala Thr Lys Ala Phe Ser Gln Leu Glu
     50                  55                  60
Ile Ala Lys Ala Glu Gly Tyr Asp Asp Ile Lys Ile Thr Gly Pro Arg
 65                  70                  75                  80
Leu Asp Met Asp Thr Asp Phe Lys Thr Trp Ile Gly Val Ile Tyr Ala
                 85                  90                  95
Phe Ser Lys Tyr Gly Leu Ser Ser Asn Thr Ile Gln Leu Ser Phe Gln
             100                 105                 110
Glu Phe Ala Lys Ala Cys Gly Phe Pro Ser Lys Arg Leu Asp Ala Lys
         115                 120                 125
Leu Arg Leu Thr Ile His Glu Ser Leu Gly Arg Leu Arg Asn Lys Gly
     130                 135                 140
Ile Ala Phe Lys Arg Gly Lys Asp Ala Lys Gly Gly Tyr Gln Thr Gly
145                 150                 155                 160
Leu Leu Lys Val Gly Arg Phe Asp Ala Asp Leu Asp Leu Ile Glu Leu
                 165                 170                 175
Glu Ala Asp Ser Lys Leu Trp Glu Leu Phe Gln Leu Asp Tyr Arg Val
             180                 185                 190
Leu Leu Gln His His Ala Leu Arg Ala Leu Pro Lys Lys Glu Ala Ala
         195                 200                 205
Gln Ala Ile Tyr Thr Phe Ile Glu Ser Leu Pro Gln Asn Pro Leu Pro
     210                 215                 220
Leu Ser Phe Ala Arg Ile Arg Glu Arg Leu Ala Leu Gln Ser Ala Val
225                 230                 235                 240
Gly Glu Gln Asn Arg Ile Ile Lys Lys Ala Ile Glu Gln Leu Lys Thr
                 245                 250                 255
```

```
Ile Gly Tyr Leu Asp Cys Ser Ile Glu Lys Lys Gly Arg Glu Ser Phe
            260             265             270

Val Ile Val His Ser Arg Asn Pro Lys Leu Lys Leu Pro Glu
        275             280             285
```

( 2 ) INFORMATION FOR SEQ ID NO:10:

( i ) SEQUENCE CHARACTERISTICS:
        ( A ) LENGTH: 2316 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: CDS
        ( B ) LOCATION: 182..571
        ( D ) OTHER INFORMATION: /product="RepA from mutant P1, see
           Fig. 10"

( i x ) FEATURE:
        ( A ) NAME/KEY: CDS
        ( B ) LOCATION: 891..1748
        ( D ) OTHER INFORMATION: /product="IncC from mutant P1, see
           Fig. 10".

( x i ) SEQUENCE DESCRIPTION: SEQ ID NO:10:

```
TAACCACCCT GCCCCCAAAG TGCATTTATG TGTAGGACTG CCAGAGTTTA GCAGTGAATA      60

TTTTGACTGA TCTGCCAGCG TATATCCTCG ATACAGAAAC GATGCTGATG GGATTAACA      120

GGAAGAATCG CAACGTTAAT GATTACAACC GAGCTATTAG CGGTAACTAA AAGGGATTTT     180

T ATG TCT GAT AAA GTA ACA GTA AAG CAA ACT ATC AAC AAA GCG ACT         226
  Met Ser Asp Lys Val Thr Val Lys Gln Thr Ile Asn Lys Ala Thr
   1               5                  10                  15

TCA ATC TAC AAA ATT GAG CAA ATC ACT GTT GGC AGG CCA GGA TCT GAA       274
Ser Ile Tyr Lys Ile Glu Gln Ile Thr Val Gly Arg Pro Gly Ser Glu
                20                  25                  30

CAA TAC CGT CGT GCT TTC GAG CTT GCC GAT CAG CTT GGT TTA AAA CAC       322
Gln Tyr Arg Arg Ala Phe Glu Leu Ala Asp Gln Leu Gly Leu Lys His
             35                  40                  45

CCG GAT TGC ATT GAG CAT GTA TTT CCG ACC TAT GCT GAT GAG CAA TGT       370
Pro Asp Cys Ile Glu His Val Phe Pro Thr Tyr Ala Asp Glu Gln Cys
         50                  55                  60

ACT CAT GTT CTT ACC GAA GAG GAT TTT TTC AGC ACT GAA GAA CGA GAA       418
Thr His Val Leu Thr Glu Glu Asp Phe Phe Ser Thr Glu Glu Arg Glu
His
     65                  70                  75

GGC GTT GAT CGC TGC ATT GGT GTG ATT TGT TCT TCG GTA AGT GAT GAG       466
Gly Val Asp Arg Cys Ile Gly Val Ile Cys Ser Ser Val Ser Asp Glu
 80                  85                  90                  95

TTA TTC CCT AAT GTG CCT GAA TAT GGT GGT ATT GGA TAC CAA TTC CTG       514
Leu Phe Pro Asn Val Pro Glu Tyr Gly Gly Ile Gly Tyr Gln Phe Leu
                100                 105                 110

TAC GAG GGC GAT GAG CTT AAA TGC TAT GAA CAT GGT CTT CTC ATC GAA       562
Tyr Glu Gly Asp Glu Leu Lys Cys Tyr Glu His Gly Leu Leu Ile Glu
             115                 120                 125

AGC GTA GAA TAATACGACT CCCTCCAACC GGCTACGTTG GCCGGTTTTT               611
Ser Val Glu
         130

CACTTATCCA CATTATCCAC TGGATAGATC CAATAATCAG GTCCATACAG ATCCCAATTA     671

GATCCATATA GATCCCTGAT CGTTGCAGGC CGCGCCACGT CTGGCTTAGA AGTGTATCGC     731

GATGTGTGCT GGAGGGAAAA CGATGTGTGC TGGAGGGATA AAAATGTGTG CTGACGGGTT     791
```

-continued

```
GCTAATGTGT GCTGGCGGGA TATAGGATGT GTGTTGACGG GAAAGCTTGG GTAGTTATCA        851

CCACTTATAA AAACTATCCA CACAATTCGG AAAAGTAAT ATG AAT CAA TCA TTT           905
                                           Met Asn Gln Ser Phe
                                           1               5

ATC TCC GAT ATT CTT TAC GCA GAC ATT GAA AGT AAG GCA AAA GAA CTA          953
Ile Ser Asp Ile Leu Tyr Ala Asp Ile Glu Ser Lys Ala Lys Glu Leu
                10              15                  20

ACA GTT AAT TCA AAC AAC ACT GTG CAG CCT GTA GCG TTG ATG CGC TTG         1001
Thr Val Asn Ser Asn Asn Thr Val Gln Pro Val Ala Leu Met Arg Leu
            25              30                  35

GGG GTA TTC GTG CCC AAG CCA TCA AAG AGC AAA GGA GAA AGT AAA GAG         1049
Gly Val Phe Val Pro Lys Pro Ser Lys Ser Lys Gly Glu Ser Lys Glu
        40              45                  50

ATT GAT GCC ACC AAA GCG TTT TCC CAG CTG GAG ATA GCT AAA GCC GAG         1097
Ile Asp Ala Thr Lys Ala Phe Ser Gln Leu Glu Ile Ala Lys Ala Glu
55              60                  65

GGT TAC GAT GAT ATT AAA ATC ACC GGT CCT CGA CTC GAT ATG GAT ACT         1145
Gly Tyr Asp Asp Ile Lys Ile Thr Gly Pro Arg Leu Asp Met Asp Thr
70              75                  80                  85

GAT TTC AAA ACG TGG ATC GGT GTC ATC TAC GCG TTC AGC AAA TAC GGC         1193
Asp Phe Lys Thr Trp Ile Gly Val Ile Tyr Ala Phe Ser Lys Tyr Gly
                90                  95                  100

TTG TCC TCA AAC ACC ATC CAG TTA TCG TTT CAG GAA TTC GCT AAA GCC         1241
Leu Ser Ser Asn Thr Ile Gln Leu Ser Phe Gln Glu Phe Ala Lys Ala
                105                 110                 115

TGT GGT TTC CCC TCA AAA CGT CTG GAT GCG AAA CTG CGT TTA ACC ATT         1289
Cys Gly Phe Pro Ser Lys Arg Leu Asp Ala Lys Leu Arg Leu Thr Ile
        120                 125                 130

CAT GAA TCA CTT GGA CGC TTG CGT AAC AAG GGT ATC GCT TTT AAG CGC         1337
His Glu Ser Leu Gly Arg Leu Arg Asn Lys Gly Ile Ala Phe Lys Arg
135                 140                 145

GGA AAA GAT GCT AAA GGC GGC TAT AAC ACT GGT CTG CTG AAG GTC GGG         1385
Gly Lys Asp Ala Lys Gly Gly Tyr Asn Thr Gly Leu Leu Lys Val Gly
150                 155                 160                 165

CGT TTT GAT GCT GAC CTT GAT CTG ATA GAG CTG GAG GCT GAT TCG AAG         1433
Arg Phe Asp Ala Asp Leu Asp Leu Ile Glu Leu Glu Ala Asp Ser Lys
                170                 175                 180

TTG TGG GAG CTG TTC CAG CTT GAT TAT CGC GTT CTG TTG CAA CAC CAC         1481
Leu Trp Glu Leu Phe Gln Leu Asp Tyr Arg Val Leu Leu Gln His His
                185                 190                 195

GCC TTG CGT GCC CTT CCG AAG AAA GAA GCT GCA CAA GCC ATT TAC ACT         1529
Ala Leu Arg Ala Leu Pro Lys Lys Glu Ala Ala Gln Ala Ile Tyr Thr
        200                 205                 210

TTC ATC GAA AGC CTT CCG CAG AAC CCG TTG CCG CTA TCG TTC GCG CGA         1577
Phe Ile Glu Ser Leu Pro Gln Asn Pro Leu Pro Leu Ser Phe Ala Arg
215                 220                 225

ATC CGT GAG CGC CTG GCT TTG CAG TCA GCT GTT GGC GAG CAA AAC CGT         1625
Ile Arg Glu Arg Leu Ala Leu Gln Ser Ala Val Gly Glu Gln Asn Arg
230                 235                 240                 245

ATC ATT AAG AAA GCG ATA GAA CAG CTT AAA ACA ATC GGC TAT CTC GAC         1673
Ile Ile Lys Lys Ala Ile Glu Gln Leu Lys Thr Ile Gly Tyr Leu Asp
                250                 255                 260

TGT TCT ATT GAG AAG AAA GGC CGG GAA AGT TTT GTA ATC GTC CAT TCT         1721
Cys Ser Ile Glu Lys Lys Gly Arg Glu Ser Phe Val Ile Val His Ser
            265                 270                 275

CGC AAT CCA AAG CTG AAA CTC CCC GAA TAAGTGTGTG CTGGAGGGAA               1768
Arg Asn Pro Lys Leu Lys Leu Pro Glu
            280                 285

ACCGCATTAA AAAGATGTGT GCTGCCGGGA AGGCTTGTCC AATTTCCTGT TTTTGATGTG       1828
```

|            |            |            |            |            |      |
|------------|------------|------------|------------|------------|------|
| TGCGCTGGAG | GGGGACGCCC | CTCAGTTTGC | CCAGACTTTC | CCTCCAGCAC | ACATCTGTCC | 1888 |
| ATCCGCTTTT | CCCTCCAGTG | CACATGTAAT | TCTCTGCCTT | TCCCTCCAGC | ACACATATTT | 1948 |
| GATACCAGCG | ATCCCTCCAC | AGCACATAAT | TCAATGCGAC | TTCCCTCTAT | CGCACATCTT | 2008 |
| AGACTTTTAT | TCTCCCTCCA | GCACACATCG | AAGCTGCCGG | GCAAGCCGTT | CTCACCAGTT | 2068 |
| GATAGAGAGT | GAAGCTTGGC | TGCCCATTGA | AGCAGGAATC | ACCAAAATGA | TTCAGGCTAC | 2128 |
| AACCTGAACG | TAGAAGAAAT | CCGCGTCCTT | TATGCGTGGA | GGATGCCAAA | GCATGTTGTG | 2188 |
| ACACACTTGG | CAAAGGAGTA | ACCATGCAGA | GAATGCTATG | TACAAGCATC | TACGCATACA | 2248 |
| TTATTATTTT | ATGCAGCATT | TTTAATTAAA | TTCAAAAATA | CAGCATAAAG | GATGACTTTC | 2308 |
| GATGAGTG   |            |            |            |            |            | 2316 |

( 2 ) INFORMATION FOR SEQ ID NO:11:

( i ) SEQUENCE CHARACTERISTICS:
        ( A ) LENGTH: 130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Ser Asp Lys Val Thr Val Lys Gln Thr Ile Asn Lys Ala Thr Ser
 1               5                  10                  15
Ile Tyr Lys Ile Glu Gln Ile Thr Val Gly Arg Pro Gly Ser Glu Gln
            20                  25                  30
Tyr Arg Arg Ala Phe Glu Leu Ala Asp Gln Leu Gly Leu Lys His Pro
        35                  40                  45
Asp Cys Ile Glu His Val Phe Pro Thr Tyr Ala Asp Glu Gln Cys Thr
    50                  55                  60
His Val Leu Thr Glu Glu Asp Phe Phe Ser Thr Glu Glu Arg Glu Gly
65                  70                  75                  80
Val Asp Arg Cys Ile Gly Val Ile Cys Ser Ser Val Ser Asp Glu Leu
                85                  90                  95
Phe Pro Asn Val Pro Glu Tyr Gly Gly Ile Gly Tyr Gln Phe Leu Tyr
            100                 105                 110
Glu Gly Asp Glu Leu Lys Cys Tyr Glu His Gly Leu Leu Ile Glu Ser
        115                 120                 125
Val Glu
    130
```

( 2 ) INFORMATION FOR SEQ ID NO:12:

( i ) SEQUENCE CHARACTERISTICS:
        ( A ) LENGTH: 286 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Asn Gln Ser Phe Ile Ser Asp Ile Leu Tyr Ala Asp Ile Glu Ser
 1               5                  10                  15
Lys Ala Lys Glu Leu Thr Val Asn Ser Asn Asn Thr Val Gln Pro Val
            20                  25                  30
Ala Leu Met Arg Leu Gly Val Phe Val Pro Lys Pro Lys Ser Lys Lys
        35                  40                  45
Gly Glu Ser Lys Glu Ile Asp Ala Thr Lys Ala Phe Ser Gln Leu Glu
    50                  55                  60
```

|  |  |  |  |  |  |  |  |  |  |  |  |  |  |  |
|---|---|---|---|---|---|---|---|---|---|---|---|---|---|---|
| Ile 65 | Ala | Lys | Ala | Glu | Gly 70 | Tyr | Asp | Asp | Ile | Lys 75 | Ile | Thr | Gly | Pro | Arg 80 |
| Leu | Asp | Met | Asp | Thr 85 | Asp | Phe | Lys | Thr | Trp 90 | Ile | Gly | Val | Ile | Tyr 95 | Ala |
| Phe | Ser | Lys | Tyr 100 | Gly | Leu | Ser | Ser | Asn 105 | Thr | Ile | Gln | Leu | Ser 110 | Phe | Gln |
| Glu | Phe | Ala 115 | Lys | Ala | Cys | Gly | Phe 120 | Pro | Ser | Lys | Arg | Leu 125 | Asp | Ala | Lys |
| Leu | Arg 130 | Leu | Thr | Ile | His | Glu 135 | Ser | Leu | Gly | Arg | Leu 140 | Arg | Asn | Lys | Gly |
| Ile 145 | Ala | Phe | Lys | Arg | Gly 150 | Lys | Asp | Ala | Lys | Gly 155 | Gly | Tyr | Asn | Thr | Gly 160 |
| Leu | Leu | Lys | Val | Gly 165 | Arg | Phe | Asp | Ala | Asp 170 | Leu | Asp | Leu | Ile | Glu 175 | Leu |
| Glu | Ala | Asp | Ser 180 | Lys | Leu | Trp | Glu | Leu 185 | Phe | Gln | Leu | Asp | Tyr 190 | Arg | Val |
| Leu | Leu | Gln 195 | His | His | Ala | Leu | Arg 200 | Ala | Leu | Pro | Lys | Lys 205 | Glu | Ala | Ala |
| Gln | Ala 210 | Ile | Tyr | Thr | Phe | Ile 215 | Glu | Ser | Leu | Pro | Gln 220 | Asn | Pro | Leu | Pro |
| Leu 225 | Ser | Phe | Ala | Arg | Ile 230 | Arg | Glu | Arg | Leu | Ala 235 | Leu | Gln | Ser | Ala | Val 240 |
| Gly | Glu | Gln | Asn | Arg 245 | Ile | Ile | Lys | Lys | Ala 250 | Ile | Glu | Gln | Leu | Lys 255 | Thr |
| Ile | Gly | Tyr | Leu 260 | Asp | Cys | Ser | Ile | Glu 265 | Lys | Lys | Gly | Arg | Glu 270 | Ser | Phe |
| Val | Ile | Val 275 | His | Ser | Arg | Asn | Pro 280 | Lys | Leu | Lys | Leu | Pro 285 | Glu |

( 2 ) INFORMATION FOR SEQ ID NO:13:

( i ) SEQUENCE CHARACTERISTICS:
        ( A ) LENGTH: 1861 base pairs
        ( B ) TYPE: nucleic acid
        ( C ) STRANDEDNESS: both
        ( D ) TOPOLOGY: linear ( i i ) MOLECULE TYPE: DNA (genomic)

( i x ) FEATURE:
        ( A ) NAME/KEY: -
        ( B ) LOCATION: 1..1861
        ( D ) OTHER INFORMATION: /note="replication portion of Rts1, see Fig. 12"

( x i ) SEQUENCE DESCRIPTION: SEQ ID NO:13:

| | | | | | |
|---|---|---|---|---|---|
| AAGCTTATCA | GATGTATTCT | GATGCGGTTC | GATAAACCTG | TCTTACCAGA | AAGGGAACAA | 60 |
| ACTCAGATGA | AAATCATCAA | AATCTATACA | CCTCATGAAC | TGGCTCTGTT | GAGAGATCCT | 120 |
| GCTTTCAGAT | TGATAGTGAT | AGAGGCTATT | GGTACAGATG | GATTCGTTGA | GCAATATAAT | 180 |
| CTACTAAATA | ATGTCTCACT | TAATCAGCCT | AAGAACGGTC | TGGAGGTATT | AATCGATCAG | 240 |
| GCTACAGGGG | CAGCAGATAA | GCATCAACGC | GTATACTTCA | ACGGACTTCT | TAAATTTATC | 300 |
| TATGAAACTG | TATACTTACG | GTTAGAACCG | ATGGCTTTGG | GGTAGTTCCG | GGAACCGTTG | 360 |
| TCGGGTAATG | AATGGGTTTA | CCTTTCATTG | CCCGGCAGCG | GTTGGACAAG | CGTAGCGCGT | 420 |
| CAGATATTCC | TCCACATTAC | CATCATTTAA | AGTTATCCAC | ATATCCACCG | TGTAGATCCA | 480 |
| ATAATAGATC | CATAGAGAGA | TCCAGATAAA | ACCAAAAAGA | TCCCCGTGGT | CTGTAGCCTT | 540 |

| | | | | | |
|---|---|---|---|---|---|
| ACTGCCACAA | GGCTTACAAC | GTTTTTCGGT | GTGTGCTGAG | GGGAAAAAGG | TGTGTGCTGA | 600 |
| GGGGAAGAAA | GTGTGTGTTA | CGGGGATTTG | GGTGTGTGCT | GAGGGGAAAA | AAGGTGGGCG | 660 |
| TCACCGGGAA | AATGTGATAC | TTTTCCACAA | TCGTAGCATT | TACGTGGGGG | GAATTATTTT | 720 |
| ATTATGGAAA | CTCAACTAGT | TATATCTGAT | GTGTTATTTG | GTAACACGGA | AGAAAAACAA | 780 |
| AAACCATTAA | CAGTTAATGA | ACTGAATACA | ATTCAACCAG | TGGCCTTTAT | GCGCCTTGGC | 840 |
| CTGTTTGTGC | CTAAACCATC | AAGGTCATCT | GACTACAGCC | CGATGATTGA | TGTCAGTGAA | 900 |
| TTAAGTTCTA | CCTTTGAATT | TGCAAGACTT | GAGGGGTTTA | CTGACATAAA | AATCACTGGT | 960 |
| GAACGTCTTG | ATATGGATAC | TGATTTCAAG | GTGTGGATCG | GCATAGTCAA | AGCGTTCAGC | 1020 |
| AAGTACGGGA | TTTCGTCAAA | CCGCATCAAA | CTAAAGTTTT | CTGAGTTCGC | AAAAGATTGT | 1080 |
| GGTTTCCCCG | GTAAAAAACT | GGACAACAAA | CTGAGAGCGC | ATATAGATGA | ATCGCTTCGT | 1140 |
| AAAATCAGGG | GGAAATCGAT | CTCATTTAAG | CGACGCAAAG | ATTCACAATC | TGCATATCAT | 1200 |
| ACCGGCCTCA | TAAAGATAGC | CTATTTCAAT | GCCGATACAG | ACGTTGTGGA | ACTGGAAGCA | 1260 |
| GACGAGCGAT | TATGGGAGTT | ATACTACTAC | TTTGATTATC | GTGTTGTTCT | TCAACTACAT | 1320 |
| GCAATAAAAG | CCCTTCCACG | TCTAGAAGTT | GCACAAGCCC | TGTATACCTT | CCTTGCAAGC | 1380 |
| CTTCCAAGTA | ACCCGGCTCC | TATCTCTTTT | AAACGCCTAC | GTGAAAGGTT | GTCTCTGATC | 1440 |
| AGTCAGGTTA | AGAACAGAA | TCGAATAATC | AAAAAGCGA | TTACTAAGCT | GATAGATATC | 1500 |
| GGCTATTTGG | ACGCTTCTAT | GGTGAAAAAA | GGACAAGAGA | ATTACCTCAT | CATTCACAAG | 1560 |
| CGAAGTCCAA | AGCTAAGTGT | AATCAACGAA | TAAGTGTGTC | CTGTGGTTTG | GCTGTCAATG | 1620 |
| AAAAGTGTGT | GTCAGGGGGG | TAACAGTCAT | TGCAAAGGTG | TGTGTCAGGG | GGAACTGATC | 1680 |
| GCCTCTCTGG | CAAGGTGTGT | GTCACGGGGG | AATGCCACTG | GCAAGGTGTG | CGTCAGGGGG | 1740 |
| AAAATTGGTG | GTTTTCCCTC | CGAGTGAGTA | TCAGCGGGCG | TAATTATCAC | CGGTAAAGTG | 1800 |
| TGTGTCAGGG | GGAAGGAATT | GGCTTCGTT | CGGTGTGTGC | CAAGGGGTTT | GACGGGAATT | 1860 |
| C | | | | | | 1861 |

( 2 ) INFORMATION FOR SEQ ID NO:14:

( i ) SEQUENCE CHARACTERISTICS:
  ( A ) LENGTH: 1590 base pairs
  ( B ) TYPE: nucleic acid
  ( C ) STRANDEDNESS: both
  ( D ) TOPOLOGY: linear ( i i ) MOLECULE TYPE: DNA (genomic)

( i x ) FEATURE:
  ( A ) NAME/KEY: -
  ( B ) LOCATION: 1..1590
  ( D ) OTHER INFORMATION: /note="GH3 fragment which
   stabilizes pOK at 42.5 degrees, see Fig. 15"

( x i ) SEQUENCE DESCRIPTION: SEQ ID NO:14:

| | | | | | |
|---|---|---|---|---|---|
| AAGCTTCAAC | GAAAAAAATA | AATGAAAAGA | TGTTCCGAGT | TACTGGCCTT | AGTGCTGGTT | 60 |
| TTTTTGTGTA | GTGATCTGGG | GTTTACTGCG | CCCTCCCCAG | CCACCAGCAG | CACGGTTGCC | 120 |
| TATCTATATC | ATACCCGCCT | TGCGCGGGTT | TTTCTTTTCT | GAGGAACCGG | TAGTACCGGT | 180 |
| AACGGCTTCG | GCTGATGCCC | CTATGCAGTT | TCGCATTCAG | GATCAAGGTA | CAGGACTGAA | 240 |
| AAGGGATTCA | GTGTAAGGGA | TCTTGATGGG | CTGGCAGGAC | ACCAGTGTAA | AACAGTTTTT | 300 |
| CGTTTCGGCG | GCTCTTGGT | GACCGTTCTT | GTTCATGATA | CCTTATTCAT | ATAGTGTATG | 360 |
| AATAAGGTGT | TTTAGCCGAA | CTTAACAGGA | GCATGAACAT | GACCACTCAT | CAGGAAACAC | 420 |
| TGGCCGCTTT | GATCGACGCA | CTGGAATGGA | TTGACGCAGT | ACCTTCCGAC | GTTCCGTTGC | 480 |

```
CATCTATGCC  GGGTTTTGAC  CGTGATAGCG  TGAATGAGCT  GGTGGAGAGA  GCTCGGCAAG    540
AGATTAAGCA  AGGTGTTGAA  GTGACGTTCT  ACCTGCCGGG  AACCTACCAG  ACATCCTGTG    600
AAGAAGGTGA  GAAATATCTT  TGCCCTCAAG  AGGTGGAAGA  AGCAATTATG  ACTGCGGGCA    660
GTAATGTCGG  GCAGCAATGT  CGAGCATCTT  GGACTGAGAT  TTTAGGTGGA  AAGTGCCGCT    720
GAGTAAGATC  ACCATAGAGC  CCGGCTAAGC  CGGGTTTTTC  TTTTGCAGGC  TACGATCTAC    780
CCTGACCCCT  CAAGTTTCTT  ATCAACTCCC  CCCACTATCC  ATATACCTCT  GTATTGCACA    840
TCGTGTAATA  TCGCGGTATA  GTATTACACA  CCATGTAATA  CAGAGATGGC  CGATGATAAA    900
ATCTTTCAAA  GCACAAAGGA  TTGAAACTGC  TTTTTGAAAA  GGGTGTTACT  TCTGGTGTGC    960
CTGCGCAAGA  TGTGACAGAA  TCAATGACCG  TTTGCAGGCC  ATCGATACAG  CGACAGAGAT   1020
TGGTGAACTA  AACCGCCAGA  TTTACAAATT  ACATCCATTA  AAGGGGATC   GGGAAGGTTA   1080
CTGGTCTATC  ACTGTCCGGG  CGAATTGGCG  CATTACTTTT  CAGTTCATTA  ACGGTGATGC   1140
TTACATTTTA  AATTATGAGG  ATTATCACTA  ATGAGACAAT  TCAAGGTTTC  ACATCCGGGT   1200
GAGATGATAG  CCCGCGATTT  AGAGGATATG  GGAGTGAGTG  GCGTCGTTTT  GCTCACAATA   1260
TTGGTGTTAC  ACCAGCAACC  GTATCCCGTC  TACTTGCGCG  GAAAACTGCG  TTGACCCCTT   1320
CTCTCTTTCG  ATTCGTATTG  CTGCGCACTG  GGGAGTACGC  CTGAGTTTTG  GTTACGGCTA   1380
CAGAGCAATT  ATGATCTGCC  CCAGTTGGAA  AACCAAATCG  ATACATCCGG  GATCGTCTTG   1440
TACGGTGAGT  CGAACGAACA  GCAGCAGAAC  GCGCAAGAGC  ATTAATTAAT  TTCTGATGCG   1500
AGGCCACCAG  CCTTGCATCA  GCTACCCTGA  GCCCTAATAG  CTTTATCCTG  CCAACTTTCT   1560
CTTACCCTCC  GGGTGATTTC  TTACAAGCTT                                      1590
```

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

```
TGCAATAAAA  GCCCTTC                                                       17
```